US010987417B2

(12) United States Patent
Strong et al.

(10) Patent No.: US 10,987,417 B2
(45) **Date of Patent: *Apr. 27, 2021**

(54) ENGINEERED AND MULTIMERIZED HUMAN IMMUNODEFICIENCY VIRUS ENVELOPE GLYCOPROTEINS AND USES THEREOF

(71) Applicant: Fred Hutchinson Cancer Research Center, Seattle, WA (US)

(72) Inventors: Roland K. Strong, Seattle, WA (US); Colin Correnti, Seattle, WA (US); Leonidas Stamatatos, Seattle, WA (US); Andrew McGuire, Seattle, WA (US)

(73) Assignee: Fred Hutchinson Cancer Research Center, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/430,172

(22) Filed: Jun. 3, 2019

(65) Prior Publication Data

US 2019/0321461 A1 Oct. 24, 2019

Related U.S. Application Data

(62) Division of application No. 15/561,438, filed as application No. PCT/US2016/023985 on Mar. 24, 2016, now Pat. No. 10,342,863.

(Continued)

(51) Int. Cl.

*C12N 7/00* (2006.01)
*A61K 39/21* (2006.01)

(Continued)

(52) U.S. Cl.

CPC .............. *A61K 39/21* (2013.01); *A61K 39/12* (2013.01); *A61P 31/18* (2018.01); *C07K 14/005* (2013.01);

(Continued)

(58) Field of Classification Search

None

See application file for complete search history.

(56) References Cited

U.S. PATENT DOCUMENTS

| | | | |
|---|---|---|---|
| 7,537,769 | B2 | 5/2009 | Hone et al. |
| 8,865,876 | B2 | 10/2014 | Mayo et al. |

(Continued)

FOREIGN PATENT DOCUMENTS

| | | | |
|---|---|---|---|
| WO | WO1991011461 | A1 | 8/1991 |
| WO | WO2009147196 | A1 | 12/2009 |
| WO | WO2013056122 | A1 | 4/2013 |

OTHER PUBLICATIONS

Dervillez, et al., "Stable Expression of Soluble Therapeutic Peptides in Eukaryotic Cells by Multimerisation: Application to the HIV-1 Fusion Inhibitory Peptide C46," ChemMedChem, vol. 1, 2006, pp. 330-339.

(Continued)

*Primary Examiner* — M Franco G Salvoza

(74) *Attorney, Agent, or Firm* — Lee & Hayes PC; C. Rachal Winger

(57) ABSTRACT

Engineered and multimerized human immunodeficiency virus (HIV) envelope glycoproteins are described. The envelope glycoproteins can be multimerized using a heptamerization domain such as a C4b binding protein multimerization domain or a ferritin fusion. The engineered and multimerized envelope glycoproteins can derived from glycoprotein 120 (gp120) and can used as an HIV vaccine.

11 Claims, 33 Drawing Sheets

Specification includes a Sequence Listing.

VWKEAKTTLFCASDAKAYEKECHNVWATHACVPTDPNPQEVVLENVTENFNMWKNDMVD
QMQEDVISIWDQCLKPCVKLTNTSTLTQACPKVTFDPIPIHYCAPAGYAILKCNNKTFNGKGP
CNNVSTVQCTHGIKPVVSTQLLLNGSLAEEEIVIRSKNLRDNAKIIIVQLNKSVEIVCTRPNNG
GSGSGGDIRQAYCNISGRNWSEAVNQVKKKLKEHFPHKNISFQSSSGGDLEITTHSFNCGG
EFFYCNTSGLFNDTISNATIMLPCRIKQIINMWQEVGKAIYAPPIKGNITCKSDITGLLLLRDGG
DTTDNTEIFRPSGGDMRDNWRSELYKYKVVEIKPLSGRAHAGWETPEGCEQVLTGKRLMQ
CLPNPEDVKMALEVYKLSLEIEQLELQRDSARQSTLDKELVPRGSHHHHHH*

Underlined amino acids represent the multimerization domain.

Related U.S. Application Data

(60) Provisional application No. 62/266,532, filed on Dec. 11, 2015, provisional application No. 62/137,764, filed on Mar. 24, 2015.

(51) Int. Cl.
  *A61K 39/12* (2006.01)
  *C07K 14/005* (2006.01)
  *A61P 31/18* (2006.01)
  *C07K 14/16* (2006.01)

(52) U.S. Cl.
  CPC .... *C07K 14/16* (2013.01); *C12N 2740/16034* (2013.01); *C12N 2740/16122* (2013.01); *C12N 2740/16134* (2013.01)

(56) References Cited

U.S. PATENT DOCUMENTS

| | | |
|---|---|---|
| 2008/0311106 A1 | 12/2008 | Hill |
| 2012/0282290 A1 | 11/2012 | Spencer |
| 2014/0227311 A1 | 8/2014 | Bahrami et al. |
| 2014/0322269 A1 | 10/2014 | Huang |
| 2018/0117140 A1 | 5/2018 | Strong et al. |

OTHER PUBLICATIONS

Dosenovic, et al., "Anti-HIV-1 B cell responses are dependent on B cell precursor frequency and antigen-binding affinity," PNAS, vol. 115, No. 18, 2018, 19 pages.

Dosenovic, et al., "Immunization for HIV-1 Broadly Neutralizing Antibodies in Human Ig Knockin Mice," Cell, vol. 161, No. 7, 2015, pp. 1505-1515.

Extended European Search Report dated Oct. 15, 2018, for European Application No. 16769681.4, 17 pages.

Forbes, et al., "T Cell Responses Induced by Adenoviral Vectored Vaccines Can Be Adjuvanted by Fusion of Antigen to the Oligomerization Domain of C4b-Binding Protein", PLoS One, vol. 7, No. 9, 2012, 12 pages.

Jardine, et al., "Rational HIV immunogen design to target specific germline B cell receptors," Science, vol. 340, No. 6133, 2013, pp. 711-716.

Jardine, et al., "Supplementary Materials for Rational HIV Immunogen Design to Target Specific Germline B Cell Receptors," Science, vol. 340, No. 6133, 2013, 77 pages.

McGuire, et al., "Antigen modification regulates competition of broad and narrow neutralizing HIV antibodies," Science, vol. 346, No. 6215, 2014, pp. 1380-1383.

McGuire, et al., "Diverse Recombinant HIV-1 Envs Fail to Activate B Cells Expressing the Germline B Cell Receptors of the Broadly Neutralizing Anti-HIV-1 Antibodies PG9 and 447-52D," J. Virol., vol. 88, No. 5, 2013, pp. 2645-2657.

McGuire, et al., "Engineering HIV envelope protein to activate germline B cell receptors of broadly neutralizing anti-CD4 binding site antibodies," J. Exp. Med., vol. 210, No. 4, 2013, pp. 655-663.

McGuire, et al., "Specifically modified Env immunogens activate B-cell precursors of broadly neutralizing HIV-1 antibodies in transgenic mice," Nat. Commun., vol. 7, 2016, 10 pages.

Office Action dated Oct. 18, 2018 for U.S. Appl. No. 15/561,438, 7 pages.

Ogun, et al., "The oligomerization domain of C4-binding protein (C4bp) acts as an adjuvant, and the fusion protein comprised of the 19-kilodalton merozoite surface protein 1 fused with the murine C4bp domain protects mice against malaria," Infect. Immun., vol. 76, No. 8, 2008, pp. 3817-3823.

Invitation to Pay Additional Fees dated Jun. 7, 2016 for PCT Application No. PCT/US2016/023985.

Search Report and Written Opinion dated Aug. 19, 2016 for International Application No. PCT/US2016/023985.

Tian, et al., "Induction of HIV Neutralizing Antibody Lineages in Mice with Diverse Precursor Repertoires," Cell, vol. 166, No. 6, 2016, pp. 1471-1484.

Wang, et al., "A systematic study of the N-glycosylation sites of HIV-1 envelope protein on infectivity and antibody-mediated neutralization," Retrovirology, vol. 10, 2013, 14 pages.

Yacoob, et al., "Differences in Allelic Frequency and CDRH3 Region Limit the Engagement of HIV Env Immunogens by Putative VRCOI Neutralizing Antibody Precursors," Cell, vol. 17, No. 6, 2016, pp. 1560-1570.

Office Action dated Jul. 27, 2020 for European Patent Application No. 16769681.4, 6 pages.

FIG. 1

VWKEAKTTLFCASDAKAYEKECHNVWATHACVPTDPNPQEVVLENVTENFNMWKNDMVD
QMQEDVISIWDQCLKPCVKLTNTSTLTQACPKVTFDPIPIHYCAPAGYAILKCNNKTFNGKGP
CNNVSTVQCTHGIKPVVSTQLLLNGSLAEEEIVIRSKNLRDNAKIIIVQLNKSVEIVCTRPNNG
GSGSGGDIRQAYCNISGRNWSEAVNQVKKKLKEHFPHKNISFQSSSGGDLEITTHSFNCGG
EFFYCNTSGLFNDTISNATIMLPCRIKQIINMWQEVGKAIYAPPIKGNITCKSDITGLLLLRDGG
DTTDNTEIFRPSGGDMRDNWRSELYKYKVVEIKPL<u>SGRAHAGWETPEGCEQVLTGKRLMQ
CLPNPEDVKMALEVYKLSLEIEQLELQRDSARQSTLDKELVPR</u>GSHHHHHH*

Underlined amino acids represent the multimerization domain.

FIG. 2

<u>        Signal Peptide    </u>
<u>MDAMKRGLCCVLLLCGAVFVSPSAS</u>VWKEAKTTLFCASDAKAYEKECH
VWATHACVPTDPNPQEVVLENVTENFNMWKNDMVDQMQEDVISIWDQ
CLKPCVKLTNTSTLTQACPKVTFDPIPIHYCAPAGYAILKCNNKTFNG
KGPCNNVSTVQCTHGIKPVVSTQLLLNGSLAEEEIVIRSKNLRDNAKI
IIVQLNKSVEIVCTRPNNGGSGSGGDIRQAYCNISGRNWSEAVNQVKK
KLKEHFPHKNISFQSSSGGDLEITTHSFNCGGEFFYCNTSGLFNDTIS
NATIMLPCRIKQIINMWQEVGKAIYAPPIKGNITCKSDITGLLLLRDG
GDTTDNTEIFRPSGGDMRDNWRSELYKYKVVEIKPLSGR*AHAGWETPE*
*GCEQVLTGKRLMQCLPNPEDVKMALEVYKLSLEIEQLELQRDSARQST*
*LDKELV*PRGS HHHHHH    (SEQ ID NO: 134)

Underlined is DMRS core gp120
*Italics is C4b heptamerization domain*
His tag is boxed
Plain text is linker region
Signal peptide indicated.

FIG. 6B

| Envelope | WT | N460D N463D | TM1 | TM2 | TM3 | TM4 |
|---|---|---|---|---|---|---|
| Mutations | None | N460D N463D | N276D N460D N463D | S278A N460D N463D | S278R N460D N463D | S278R N460D N463D G471S |

| Envelope | TM5 | TM1ΔV1-3 | TM4ΔV1-3 | TM5ΔV1-3 |
|---|---|---|---|---|
| Mutations | N276D S278R N460D N463D G471S | N276D N460D N463D ΔV1 V2 V3 | S278R N460D N463D G471S ΔV1 V2 V3 | N276D S278R N460D N463D G471S ΔV1 V2 V3 |

FIG. 7

|  | | CDRL1 | | CDRL2 |
|---|---|---|---|---|
| gIVRC/NIH | EIVLTQSPAT | LSLSPGERATLSCRASQSVS SYLAWYQQKP | GQAPRLLIYDASNRATGIPA |
| gII2A21 | DIQMTQSPSS | LSASVGDRVTITCQASQDIS NYLNWYQQKP | GKAPKLLIYDASNLETGVPS |
| g13BNC60 | DIQMTQSPSS | LSASVGDRVTITCQASQDIS NYLNWYQQKP | GKAPKLLIYDASNLETGVPS |
| g1VRC-CH31 | DIQMTQSPSS | LSASVGDRVTITCQASQDIS NYLNWYQQKP | GKAPKLLIYDASNLETGVPS |
| g1PGV04 | EIVLTQSPGT | LSLSPGERATLSCRASQSVS SSYLAWYQQK | PGQAPRLLIYGASSRATGIP |
| gIPGV19/20 | QSALTQPASV | SGSPGQSITI SCTGTSSDVG GYNYVSWYQQ | HPGKAPKLMIYEVSNRPSGV |

CDRL3

| gIVRC/NIH | RFSGSGSGTD | FTLTISSLEP | EDFAVYYCQQYEFFGQGTKL EIK | (SEQ ID NO: 135) |
|---|---|---|---|---|
| gII2A21 | RFSGSGSGTD | FTFTISSLQP | EDIATYYCAVLEFFGPGTKV DIK | (SEQ ID NO: 136) |
| g13BNC60 | RFSGSGSGTD | FTFTISSLQP | EDIATYYCQQYEFIGPGTKV DIK | (SEQ ID NO: 137) |
| g1VRC-CH31 | RFSGSGSGTD | FTFTISSLQP | EDIATYYCQQYETFGQGTKL EIK-- | (SEQ ID NO: 138) |
| g1PGV04 | DRFSGSGSGT | DFTLTISRLE | PEDFAVYYCQQLEFFGQGTR LEIK | (SEQ ID NO: 139) |
| gIPGV19/20 | SNRFSGSKSG | NTASLTISGL | QAEDEADYYCSSYEFFGGGT KVFVL | (SEQ ID NO: 140) |

FIG. 10A
FIG. 10B
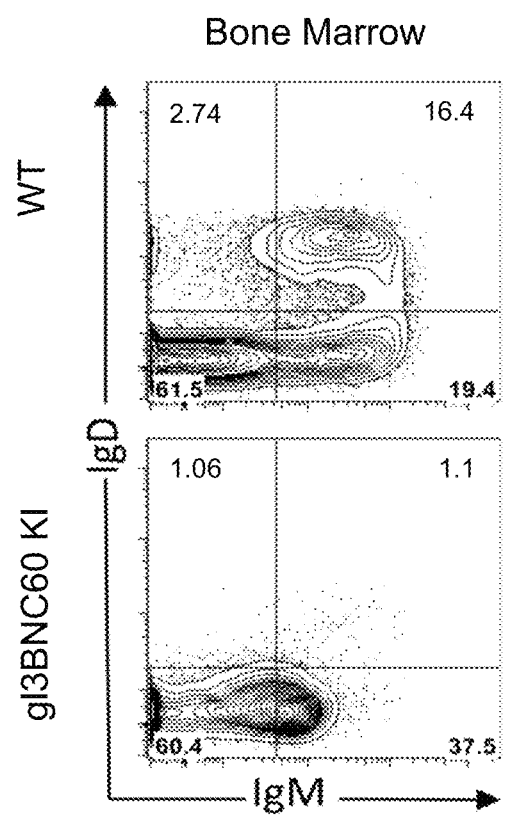
Bone Marrow
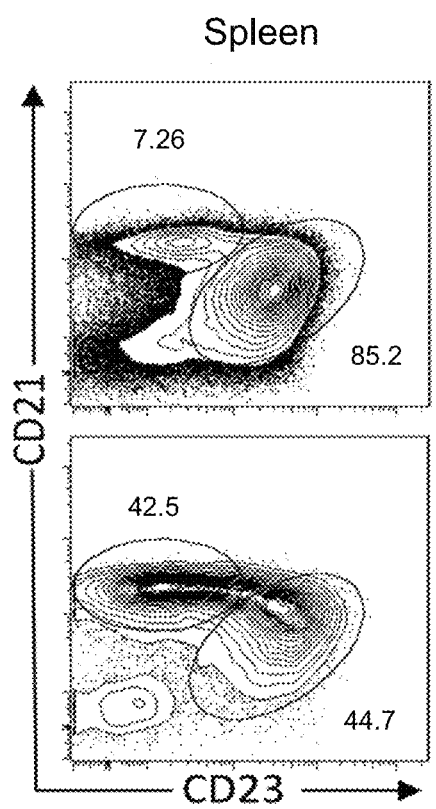
Spleen

FIG. 10D

TM4ΔV1-3 gp140-dex

FIG. 10E

TM4ΔV1-3 gp120-dex

OD at Dil 1/300

OD at Dil 1/270

OD at Dil 1/270

FIG. 10G

TM4ΔV1-3 gp120-ferritin

OD at Dil 1/270

● TM4ΔV1-3
○ TM4ΔV1-3 KO

FIG. 11C
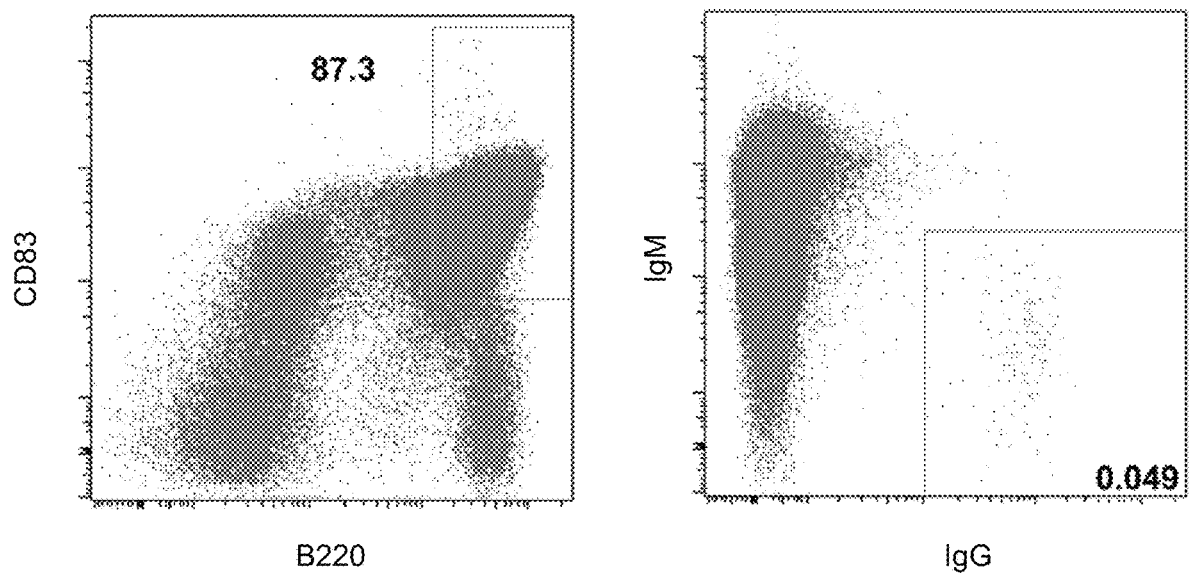
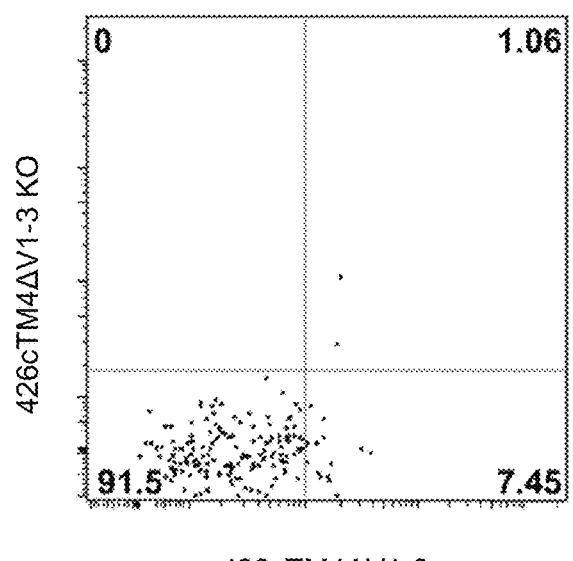

FIG. 11D

| Antibody chain | Heavy | Light |
|---|---|---|
| # of Sorted Cells | 96 | 96 |
| # of recovered gl3BNC60 sequences | 13 | 61 |
| Frequency of gl3BNC60 sequences | 14% | 63% |

FIG. 14

```
Heavy Chain
                                CDRH1                         CDRH2
g13BNC60   QVQLVQSGAEVKKPGASVKVSCKASGYTFTGYYMHWVRQAPGQGLEWMGWINPNSGGTNYAQKFQG
HC Seq1    ..........................H.................................
HC Seq2    ...............................Q............................

CDRH3
g13BNC60   RVTMTRDTSISTAYMELSRLRSDDTAVYYCARERSDFWDFDLWGRGTLVTVSS   (SEQ ID NO: 141)
HC Seq1    .....................................................   (SEQ ID NO: 142)
HC Seq2    .....................................................   (SEQ ID NO: 143)

Light Chain
                                CDRL1                   CDRL2
g13BNC60   DIQMTQSPSSLSASVGDRVTITCQASQDISNYLNWYQQKPGKAPKLLIYDASNLET
LC Seq1    ........................................................
LC Seq2    ..................................F........L...........
LC Seq3    ...........................CF.H.S......................

CDRL3
g13BNC60   GVPSRFSGSGSGTDFTFTISSLQPEDIATYYCQQYEFIGPGTKVDIKR   (SEQ ID NO: 147)
LC Seq1    ......................N.........................  (SEQ ID NO: 144)
LC Seq2    .............G...................................  (SEQ ID NO: 145)
LC Seq3    ............A.SS........F........................ (SEQ ID NO: 146)
```

FIG. 15

| Env Name | $K_a(M^{-1})$ | $k_{on}(M^{-1}s^{-1})$ | $k_{on}$ error | $k_{off}(s^{-1})$ | $k_{off}$ error |
|---|---|---|---|---|---|
| gIVRC01 | | | | | |
| TM1 | 1.31E+06 | 1.48E+04 | 7.22E+02 | 1.13E-02 | 1.83E-04 |
| TM2 | 6.28E+05 | 3.63E+04 | 3.10E+03 | 5.79E-02 | 1.66E-03 |
| TM3 | 5.62E+05 | 3.60E+04 | 2.12E+03 | 6.40E-02 | 1.16E-03 |
| TM4 | 1.08E+06 | 2.87E+04 | 1.07E+03 | 2.64E-02 | 3.21E-04 |
| TM5 | 1.14E+07 | 2.56E+04 | 2.26E+02 | 2.25E-03 | 7.24E-06 |
| TM1ΔV1-3 | 3.09E+06 | 4.84E+03 | 3.34E+01 | 1.57E-03 | 5.29E-06 |
| TM4ΔV1-3 | 1.47E+06 | 6.25E+03 | 7.05E+01 | 4.26E-03 | 1.42E-05 |
| TM5ΔV1-3 | 1.06E+07 | 6.86E+03 | 4.74E+01 | 6.50E-04 | 4.84E-06 |
| gl NIH45-46 | | | | | |
| TM1 | 6.29E+05 | 9.63E+03 | 4.56E+02 | 1.53E-02 | 2.10E-04 |
| TM2 | 1.45E+05 | 1.84E+04 | 5.15E+03 | 1.27E-01 | 1.02E-02 |
| TM3 | 2.17E+05 | 2.90E+04 | 8.23E+03 | 1.34E-01 | 9.20E-03 |
| TM4 | 3.41E+05 | 1.86E+04 | 2.00E+03 | 5.46E-02 | 1.86E-03 |
| TM5 | 4.74E+06 | 1.53E+04 | 1.83E+02 | 3.23E-03 | 1.27E-05 |
| TM1ΔV1-3 | 6.82E+05 | 4.05E+03 | 4.15E+01 | 5.94E-03 | 1.41E-05 |
| TM4ΔV1-3 | 2.11E+05 | 4.78E+03 | 2.34E+02 | 2.26E-02 | 2.84E-04 |
| TM5ΔV1-3 | 4.59E+06 | 6.23E+03 | 3.81E+01 | 1.36E-03 | 4.70E-06 |
| gl 12A21 | | | | | |
| TM1 | - | - | - | - | - |
| TM2 | 2.01E+05 | 5.52E+04 | 1.15E+04 | 2.74E-01 | 2.12E-02 |
| TM3 | 1.74E+05 | 4.85E+04 | 9.76E+03 | 2.79E-01 | 1.67E-02 |
| TM4 | 3.34E+05 | 5.62E+04 | 5.35E+03 | 1.68E-01 | 5.24E-03 |
| TM5 | 3.85E+04 | 1.55E+04 | 6.15E+03 | 4.03E-01 | 2.34E-02 |
| TM1ΔV1-3 | - | - | - | - | - |
| TM4ΔV1-3 | 3.11E+05 | 9.47E+03 | 8.13E+02 | 3.05E-02 | 6.14E-04 |
| TM5ΔV1-3 | 3.08E+04 | 1.59E+03 | 9.83E+02 | 5.15E-02 | 1.72E-03 |

FIG. 15 (cont'd)

| | gl VRC-PG19 | | | | |
|---|---|---|---|---|---|
| TM1 | 2.87E+05 | 4.00E+04 | 4.20E+03 | 1.40E-01 | 4.93E-03 |
| TM2 | 4.16E+05 | 7.15E+04 | 1.17E+04 | 1.72E-01 | 7.03E-03 |
| TM3 | 2.24E+06 | 9.89E+04 | 3.99E+03 | 4.42E-02 | 5.63E-04 |
| TM4 | 5.45E+06 | 9.80E+04 | 4.21E+03 | 1.80E-02 | 1.65E-04 |
| TM5 | 5.22E+06 | 8.38E+04 | 3.36E+03 | 1.60E-02 | 1.48E-04 |
| TM1ΔV1-3 | 3.53E+05 | 1.11E+04 | 3.29E+02 | 3.15E-02 | 2.48E-04 |
| TM4ΔV1-3 | 8.90E+06 | 2.41E+04 | 1.54E+02 | 2.70E-03 | 4.92E-06 |
| TM5ΔV1-3 | 8.93E+06 | 1.93E+04 | 1.09E+02 | 2.16E-03 | 4.04E-06 |

FIG. 15 (cont'd)

| | giVRC-PG20 | | | | |
|---|---|---|---|---|---|
| TM1 | 1.40E+07 | 4.97E+04 | 9.74E+02 | 3.43E-03 | 1.39E-05 |
| TM2 | 3.88E+06 | 5.09E+04 | 1.54E+03 | 1.29E-02 | 9.98E-05 |
| TM3 | 1.20E+07 | 6.05E+04 | 1.28E+03 | 4.87E-03 | 1.92E-05 |
| TM4 | 2.28E+07 | 6.11E+04 | 1.27E+03 | 2.57E-03 | 1.11E-05 |
| TM5 | 1.78E+08 | 1.12E+05 | 1.13E+03 | 5.53E-04 | 5.05E-06 |
| TM1ΔV1-3 | 1.24E+07 | 1.35E+04 | 1.99E+02 | 1.04E-03 | 9.40E-06 |
| TM4ΔV1-3 | 3.84E+07 | 2.45E+04 | 1.11E+02 | 5.11E-04 | 3.11E-06 |
| TM5ΔV1-3 | 2.45E+08 | 4.12E+04 | 1.46E+02 | 1.49E-04 | 2.35E-06 |
| | gi3BNC60 | | | | |
| TM1 | - | - | - | - | - |
| TM2 | - | - | - | - | - |
| TM3 | - | - | - | - | - |
| TM4 | - | - | - | - | - |
| TM5 | - | - | - | - | - |
| TM1ΔV1-3 | - | - | - | - | - |
| TM4ΔV1-3 | 3.49E+03 | 1.41E+03 | 2.31E+03 | 3.98E-01 | 3.12E-02 |
| TM5ΔV1-3 | 2.18E+03 | 1.04E+03 | 3.31E+03 | 4.77E-01 | 4.79E-02 |
| | giVRC-CH31 | | | | |
| TM1 | - | - | - | - | - |
| TM2 | - | - | - | - | - |
| TM3 | - | - | - | - | - |
| TM4 | - | - | - | - | - |
| TM5 | - | - | - | - | - |
| TM1ΔV1-3 | - | - | - | - | - |
| TM4ΔV1-3 | - | - | - | - | - |
| TM5ΔV1-3 | 8.95E+03 | 2.40E+03 | 4.17E+03 | 2.40E-01 | 1.65E-02 |

FIG. 16

| Sample ID | ID50 Titer in TZM.bl cells (1:x) | | | | | | | 426c.TM4 ΔV1-3 immunogen |
|---|---|---|---|---|---|---|---|---|
| | MuLV | 426C WT | 426C.TM1 | 426C.TM4 | 426C.S278A, T462A, T465A | T247-23* | 63357.14* | |
| ES15 | <10 | <10 | <10 | <10 | <10 | <10 | <10 | Heptamer |
| HR18 | <10 | <10 | <10 | <10 | <10 | <10 | <10 | Heptamer |
| HR19 | <10 | <10 | <10 | 24 | <10 | <10 | <10 | Heptamer |
| ES3D | <10 | <10 | <10 | <10 | <10 | <10 | <10 | gp120-Dex |
| ES4D | <10 | <10 | <10 | <10 | <10 | <10 | <10 | gp120-Dex |
| ES5D | <10 | <10 | <10 | <10 | <10 | <10 | <10 | gp120-Dex |
| HS18 | <10 | <10 | <10 | <10 | <10 | <10 | <10 | Ferritin |
| HS19 | <10 | <10 | <10 | <10 | <10 | <10 | <10 | Ferritin |
| ES26 | <10 | <10 | <10 | <10 | <10 | <10 | <10 | Ferritin |
| ES27 | <10 | <10 | <10 | <10 | <10 | <10 | <10 | Ferritin |
| WT Pool | <10 | <10 | <10 | 18 | <10 | <10 | <10 | Ferritin |
| Naive g3BNC60 KI | <10 | <10 | <10 | <10 | <10 | <10 | <10 | None |

*Viruses naturally lack an NLGS at position 276

FIG. 17

| Heavy Chain Sequences | | |
|---|---|---|
| # of sequences | nt substitutions | AA substitutions |
| 11 | 0 | 0 |
| 1 | 3 | 1 |
| 1 | 1 | 1 |
| Light Chain Sequences | | |
| 57 | 0 | 0 |
| 1 | 2 | 0 |
| 1 | 1 | 1 |
| 1 | 3 | 3 |
| 1 | 11 | 8 |

ENGINEERED AND MULTIMERIZED HUMAN IMMUNODEFICIENCY VIRUS ENVELOPE GLYCOPROTEINS AND USES THEREOF

CROSS REFERENCE TO RELATED APPLICATIONS

This application is a divisional of U.S. patent application Ser. No. 15/561,438, filed Sep. 25, 2017, which is a U.S. national stage entry of International Application No. PCT/US2016/023985, filed Mar. 24, 2016, which application claims the benefit of U.S. Provisional Application No. 62/266,532 filed Dec. 11, 2015 and U.S. Provisional Application No. 62/137,764 filed Mar. 24, 2015, the entire contents of each of which are incorporated by reference herein.

STATEMENT OF GOVERNMENT INTEREST

This invention was made with government support under AI094419 and AI109632 awarded by the National Institutes of Health. The government has certain rights in the invention.

STATEMENT REGARDING SEQUENCE LISTING

The Sequence Listing associated with this application is provided in text format in lieu of a paper copy, and is hereby incorporated by reference into the specification. The name of the text file containing the Sequence Listing is DN23X2854_ST25.txt. The text file is about 182 KB, was created on Mar. 22, 2018, and is being submitted electronically via EFS-Web.

FIELD OF THE DISCLOSURE

Engineered and multimerized human immunodeficiency virus (HIV) envelope glycoproteins are described. The engineered envelope glycoproteins can be provided as multimerized heptamers. The engineered and multimerized envelope glycoproteins can be derived from glycoprotein 120 (gp120) and can used as an HIV vaccine.

BACKGROUND OF THE DISCLOSURE

Acquired Immunodeficiency Syndrome (AIDS) is characterized by immunosuppression that results in opportunistic infections and malignancies; wasting syndromes; and central nervous system degeneration. Destruction of CD4+ T-cells, which are critical to immune defense, is a major cause of the progressive immune dysfunction that is the hallmark of AIDS disease progression. The loss of CD4+ T cells seriously impairs the body's ability to fight most pathogens, but it has a particularly severe impact on the defenses against viruses, fungi, parasites and certain bacteria, including mycobacteria.

AIDS is caused by infection with human immunodeficiency virus (HIV). An infectious HIV particle includes two strands of RNA packaged within a viral protein core. The core is surrounded by a phospholipid bilayer envelope derived from a host cell membrane that also includes virally-encoded membrane proteins.

The HIV genome encodes several structural proteins and has the characteristic 5'-LTR-Gag-Pol-Env-LTR-3' organization of the retrovirus family. The env gene encodes the viral envelope glycoprotein (Env) that is translated as a 160-kilodalton (kDa) precursor (gp160) and cleaved by a cellular protease to yield an external 120-kDa envelope glycoprotein (gp120) and a transmembrane 41-kDa envelope glycoprotein (gp41). These glycoproteins are required for HIV to infect cells.

HIV infection begins when gp120 on the viral particle binds to CD4 and chemokine receptors on the cell membrane of a subject's target immune system cells (e.g., CD4+ T-cells, macrophages and dendritic cells). The bound virus then fuses with the target cell and reverse transcribes its RNA genome. The resulting viral DNA integrates into the subject cell's genome and begins to produce new viral RNA, resulting in new viral proteins and virions. The virions leave the originally infected cell to then infect new cells. This process kills the originally infected cell.

HIV-1 broadly neutralizing antibodies (bNAbs) are antibodies capable of neutralizing HIV. HIV bNAbs target four major areas of the Env: (i) the membrane proximal external region of the gp41 subunit; (ii) the CD4 receptor-binding site (CD4-BS); (iii) two sites including both carbohydrate and amino acid moieties, one at the base of the "V3" and another on the "V1/V2" loops of the gp120 subunit; and (iv) regions spanning elements of both gp120 and gp41.

Based on their ontogenies and mode of recognition, the CD4-BS bNAbs are grouped into two major types: (i) heavy chain complementary determining region three (CDRH3)-dominated; and (ii) variable heavy (VH)-gene-restricted. Antibodies that make contact primarily through their CDRH3 regions are further subdivided into the CH103, HJ16, VRC13 and VRC16 classes while the VH-gene-restricted Abs include the VRC01- and the 8ANC131-class antibodies.

VRC01-class bNAbs protect non-human primates from experimental simian/human HIV (SHIV)-infection and humanized mice from HIV-1 infection. It was therefore thought that vaccine-elicited VRC01-class bNAbs would protect humans from HIV-1 infection. With the exception of llamas however, all efforts to elicit such antibodies by immunization in humans or wild type animals with recombinant Env (rEnv) have been unsuccessful.

One of the many important reasons for the lack of success is thought to be the inability of the Env proteins used as immunogens to engage B cell receptors (BCRs) that encode the germline (gl) of VRC01-class antibodies (e.g., "immature" or not fully developed Abs). Indeed maturation of these antibodies to full neutralizing Abs requires that they circumvent steric constraints on Env through extensive somatic hypermutation. For example, HIV-1 has evolved to avoid detection by gl B cells that give rise to VRC01-class bNAbs through development of specific N-linked glycosylation sites (NLGS) (for example, in Loop D and V5 of the gp120 subunit). As a consequence, recombinant Env proteins derived from diverse HIV-1 isolates are ineffective in binding to and stimulating B cells engineered to express the glBCR forms of VRC01-class bNAbs in vitro. Targeted disruption of conserved NLGS at position 276 in Loop D, and at positions 460 and 463 in V5 of the 426c clade C Env, however, permits binding and activation gl B cell lines expressing BCRS of two clonally-related VRC01-class bNAbs, VRC01 and NIH45-46 in vitro. These two BCRs represent a small subset of potential VRC01-class antibody progenitors. Thus, designing immunogens capable of recognizing a larger group of glVRC01-class BCRs should increase the chances of activating rare, naïve glVRC01-class B cells during human immunization.

Previous reports describe preparation of artificial gp120 proteins (in some instances called "engineered outer domain" or "eOD" proteins) for use as HIV vaccines. The previous reports also describe multimerizing the artificial gp120 proteins to enhance immunogenicity of the proteins, and more particularly, the VRC01 epitope of the proteins. It was envisioned that multimerized artificial gp120 proteins would stimulate gl B cells using multivalent avidity, and, further, that the addition of the larger particulate forms would mimic a virus-like symmetric presentation of epitopes, reduce immune responses to regions buried in the multimer, and enhance in vivo trafficking of the artificial gp120 proteins to lymph nodes.

These previous reports described eOD proteins that lack normally occurring loops. The eOD proteins were also multimerized as trimers, tetramers, and octamers using coiled-coil multimerization domains. From the trimers and tetramers, octamers, 24mers, 60mers, and 180mers were formed.

SUMMARY OF THE DISCLOSURE

The present disclosure provides engineered and multimerized (e/m) human immunodeficiency virus (HIV) envelope glycoproteins (Env). The engineered Env can be provided as multimerized heptamers, dextramers or larger order-mers. The e/m Env can be derived from glycoprotein 120 (gp120) and can used as an HIV vaccine.

More particularly, the present disclosure provides specific gp120 modifications and multimerization strategies that expand the germline (gl) VRC01-class antibody-recognition potential of the Env. Importantly, B cells were inefficiently activated by soluble trimeric multimerization forms of disclosed engineered Env. Higher order multimeric forms, however, based on heptamers were effective, indicating usefulness as an HIV-1 vaccination. Of note, heptameric multimerized forms were produced using the C4b multimerization domain.

Particular embodiments of the e/m Env include the following mutations: N460D; N463D; S278R; G471S; V65C; S115C; removal of V1 and V2; V3 replacement with a flexible linker; and an N-terminal truncation. In particular embodiments, the e/m Env does not include a mutation at position 276. In particular embodiments, the e/m Env is multimerized with a C4b multimerization domain derived from chicken. In particular embodiments, the e/m Env is multimerized with a modified chicken heptamerization domain. In particular embodiments, the e/m Env includes all characteristics described in this paragraph.

BRIEF DESCRIPTION OF THE FIGURES

FIG. 1 shows the sequence of an engineered and multimerized Envelope (e/m Env, SEQ ID NO: 148) disclosed herein.

FIG. 2 shows the sequence of FIG. 1 with additional supporting sequences (SEQ ID NO: 134).

(FIG. 5A) ELISA was used to evaluate the binding of mature (left panel) or gl (right panel) VRC01 and NIH45-46 to the indicated Envs lacking NLGS in Loop D and V5. The clade of each Env is shown in parentheses. Error bars represent the s.d. from three technical replicates. (FIG. 5B) His-tagged gp120 variants of 426c were immobilized on a Ni-NTA biosensor and binding to 20 µg/ml solution of the indicated gl VRC01 class antibodies was measured by BLI. The mutations tested are indicated on the top of each panel (nomenclature in parentheses corresponds to FIG. 6B). BLI traces are representative of at least 3 independent experimental replicates. Dotted line demarcates the association and dissociation phases.

FIGS. 6A and 6B. Binding affinities of the indicated gl VRC01-class antibodies to selected 426c variants. (FIG. 6A) Soluble trimeric 426c gp140 variants were biotinylated and immobilized on a streptavidin biosensor. The association constant of the various gl VRC01-class antibodies was determined by BLI, as described in the Methods section. Undetectable antibody-Env binding is shown on the X-axis. Full kinetic parameters are shown in FIG. 15. (FIG. 6B) Key describing the various mutations on the 426c Env tested in 6A.

FIG. 7. Amino acid alignment of the light chain variable regions of gl VRC01-class antibodies (SEQ ID NOs: 135-140). Gray areas indicate (Kabat) CDRL regions. Bold letters indicate negatively charged amino acids and underlined letters indicate positively charged amino acids.

FIGS. 10A-10H. Antibody responses elicited in wild-type (WT) and knock-in gl3BNC60 mice after immunization. (FIG. 10A) Bone marrow cells (gated on; live cells, CD4-, CD8-, GR-1-and B220+) of naïve WT (top) and naïve gl3BNC60 knock-in mice (bottom) were stained for IgD and IgM as indicated to identify immature (IgM-/low, IgD-), and mature B cell populations. (FIG. 10B) Splenocytes from naïve WT and gl3BNC60 knock-in mice (gated on; live cells, CD4-, CD8-, GR-1-, B220+ and CD93-) were stained with CD21 and CD23 as indicated to identify follicular (CD21low/CD23high) and marginal zone (CD21high/CD23low) B cells. (FIG. 10A) and (FIG. 10B) show representative FACS diagrams from one individual mouse of five. (FIG. 10C) Serum IgG collected prior to (naïve) and following one or two immunizations (post 1, 2) with 426cTM4ΔV1-V3 gp140 in Alum Imject were tested for binding to 426cTM4ΔV1-V3 gp140 (closed circles) or 426cTM4ΔV1-V3.gp140.D368R.E370A protein (KO) (open circles) in WT (left panel, n=3) and knock-in gl3BNC60 mice (right panel, n=3) by ELISA. Lines connecting the black and white circles indicate OD values for 426cTM4ΔV1-V3 gp140 or 426cTM4ΔV1-V3.gp140.D368R.E370A proteins from the same mouse at the indicated concentrations. (FIG. 10D). Same as in (FIG. 10C) but WT mice (n=5) or knock-in gl3BNC60 (n=5) mice were immunized once with 426cTM4ΔV1-V3 gp140 dextramer in Alum Imject. (FIG. 10E) Same as in FIG. 10C, but WT (n=5) or knock-in gl3BNC60 mice (n=5) were immunized once with 426cTM4ΔV1-V3 gp120-dextramers in Alum Imject (left panel), or in Ribi adjuvant (n=5) (right panel). (FIG. 10F) Same as in FIG. 10C, but knock-in gl3BNC60 mice (n=5) were immunized once with 426c.TM4ΔV1-V3 gp120-C4b in Ribi adjuvant. (FIG. 10G) Same as in FIG. 10C but WT mice (n=3) or knock-in gl3BNC60 mice (n=5) were immunized once with 426cTM4ΔV1-V3 gp120-ferritin in Alum Imject. (FIG. 10H) Serum IgG from WT (n=4) and knock-in 3BNC60 mice (n=5) after one (left panel) or two (right panel) immunizations with WT 426c gp140-dextramer in Alum Imject were tested for binding to WT 426c gp140 (closed squares) or 426c.D368R.E370A (426c-KO, open squares) by ELISA. Lines between black and white squares indicate OD values for WT 426c gp140 or 426c-KO proteins from the same mouse at the indicated concentrations.

FIGS. 11A-11D. Sequencing of antibody and light chain transcripts from gl3BNC60 KI mice. (FIG. 11A) CD4-CD8-, Ly-6G- and Ly-6C- B220+CD19+ splenocytes from WT (left panel) and gl3BNC60 KI (right panel) mice were stained with anti-mouse kappa, or lambda antibodies. (FIG. 11B) Summary of kappa and lambda frequencies in WT (n=1) and gl3BNC60 KI mice (n=6) as determined in FIG. 11A. (FIG. 11C) Representative FACS plots of splenocytes from gl3BNC60 KI mice. In brief, CD4-, CD8-, Gr1- splenocytes were stained with the B cell markers B220 and CD38 (left panel), B220+, CD38+ cells were stained for IgG and IgM (middle panel). Class switched IgM-IgG+ cells were stained with 426c.TM4ΔV1-V3 and 426c.TM4ΔV1-V3-KO (right panel). 426c.TM4ΔV1-V3+, 426c.TM4ΔV1-V3-KO-(lower right hand quadrant) single cells were sorted into individual wells on a 96 well plate. (FIG. 11D) Summary of gl3BNC60 heavy and light chain sequences recovered from expressed transcripts.

(FIG. 12A) Serum IgG collected prior to (naïve) and following one or two immunizations (post 1, 2) with 426cTM4ΔV1-V3 gp140 in Alum Imject were tested for binding to 426cTM4ΔV1-V3 gp140 (solid lines) or 426cTM4ΔV1-V3.gp140.D368R.E370A protein (KO) (dotted lines) in WT (left three panels, n=3) and knock-in gl3BNC60 mice (right three panels, n=3) by ELISA. Colors indicate individual mice. (FIG. 12B) Same as in FIG. 12A but WT mice (n=5, left panel) or gl3BNC60 KI (n=5, right panel) mice were immunized once with 426cTM4ΔV1-V3 gp140 dextramer in Alum Imject. (FIG. 12C) Same as in FIG. 12A but WT (n=5, left panel) or gl3BNC60 KI mice (n=5, middle panel) were immunized once with 426cTM4ΔV1-V3 gp120-dextramers in Alum Imject, or in Ribi adjuvant (n=5, right panel). (FIG. 12D) Same as in FIG. 12A but gl3BNC60 KI mice (n=5) were immunized once with 426c.TM4ΔV1-V3 gp120-C4b in Ribi adjuvant. (FIG. 12E) Same as in a but WT mice (n=3, left panel) or gl3BNC60 KI mice (n=5, right panel) were immunized once with 426cTM4ΔV1-V3 gp120-ferritin in Alum Imject. (FIG. 12F) Serum IgG from WT (n=4, left two panels) and 3BNC60 KI mice (n=5) after one (p1) or two (p2) immunizations with WT 426c gp140-dextramer in Alum Imject were tested for binding to WT 426c gp140 (solid lines) or 426c.D368R.E370A (426c-KO, dotted lines) by ELISA.

(FIG. 13A) Chromatograms of the indicated multimeric 426cTM4ΔV1-3 variants run on a 10/300 Superose 6 column. The elution volume is indicated above the peak of each trace. (FIG. 13B) 10 μg of the indicated multimeric 426cTM4ΔV1-3 variants were subjected to BN-PAGE.

FIG. 14. Alignment of mutated gl3BNC60 sequences isolated from antigen-specific IgG+ B cells post immunization, SEQ ID NOs: 141-147. IgG+ B cells were sorted into single wells and VH and VK regions were amplified by PCR and Sanger sequenced. Of 13 heavy chain sequences that were recovered 2 had mutations that led to amino acid substitutions (top). Of 61 light chains that were recovered, 3 had mutations that led to amino acid substitutions (bottom).

FIG. 15. Binding kinetic values for the indicated antibodies to the indicated 426c based, trimeric gp140 constructs from FIGS. 6A, 6B. Values are the average of at least 2 serial Fab dilutions giving a $R^2$ value of >0.95. (–): no detectable binding.

FIG. 16. Neutralization of HIV-1 pseudoviruses by immunized mice.

FIG. 17. Summary of gl3BNC60 sequences isolated from antigen-specific IgG+ B cells post immunization.

DETAILED DESCRIPTION

Figure 3:
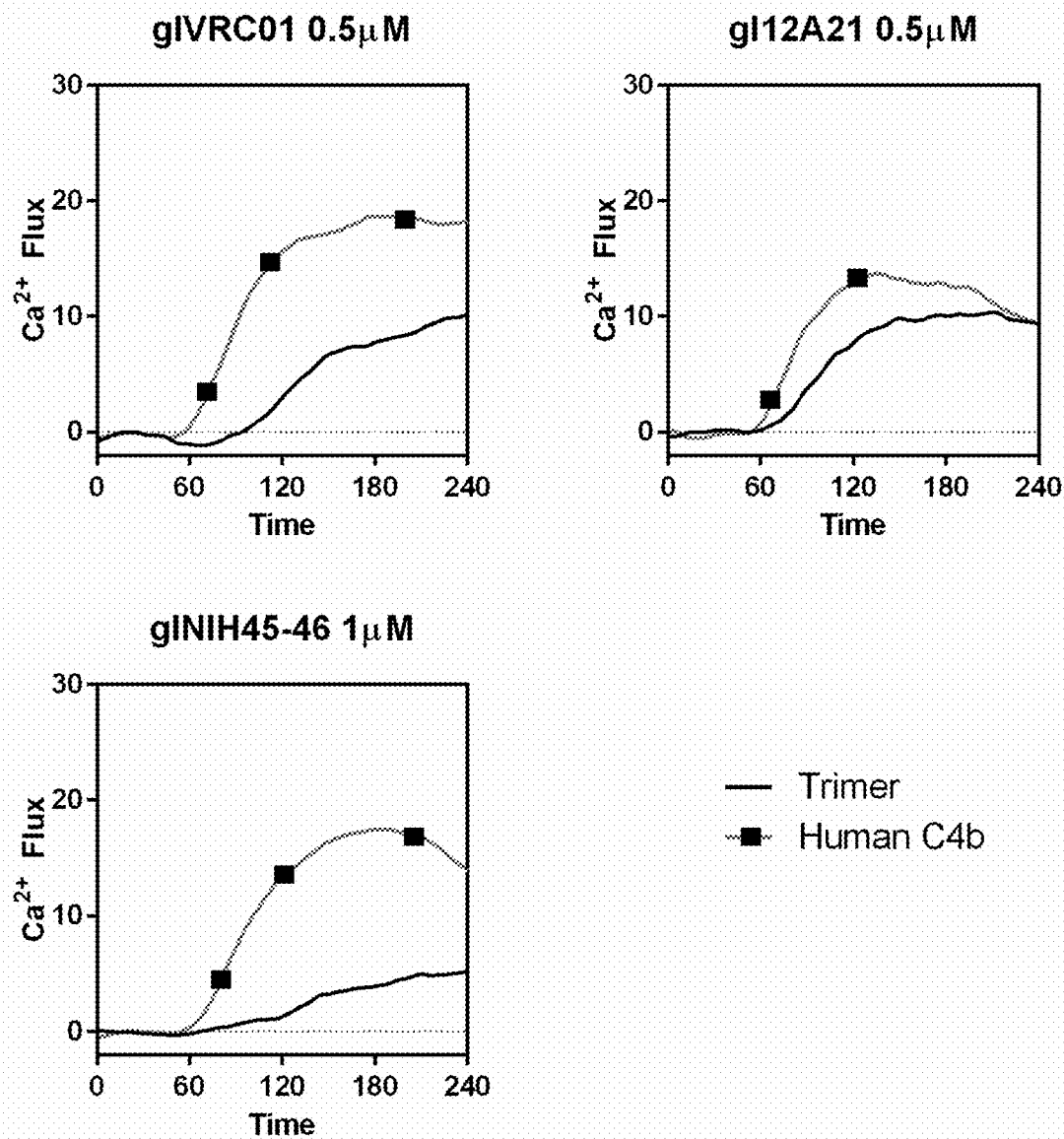
FIG. 3 shows B cell activation. DG75 B cells that were transduced to stably express the germline-reverted (gl) VRC01, 12A21, and NIH45-46 B cell receptors (as indicated), were loaded with the Calcium binding indicator dye Fluo-4. B cells were then challenged with the indicated 426c.TM4ΔV1-3 gp140 trimer (black lines) or the 426c.TM4ΔV1-3 fused to the C4b heptamerization domain (boxed lines) at the indicated concentrations, and the fluorescent signal from the Fluo-4 dye was measured over time. The 426c.TM4ΔV1-3 fused to the C4b heptamerization domain induces a stronger Calcium flux response than the trimeric form of the Envelope.

Acquired Immunodeficiency Syndrome (AIDS) is characterized by immunosuppression that results in opportunistic infections and malignancies; wasting syndromes; and central nervous system degeneration. Destruction of CD4+ T-cells, which are critical to immune defense, is a major cause of the progressive immune dysfunction that is the hallmark of AIDS disease progression. The loss of CD4+ T cells seriously impairs the body's ability to fight most pathogens, but it has a particularly severe impact on the defenses against viruses, fungi, parasites and certain bacteria, including mycobacteria.

AIDS is caused by infection with human immunodeficiency virus (HIV). An infectious HIV particle includes two strands of RNA packaged within a viral protein core. The core is surrounded by a phospholipid bilayer envelope derived from a host cell membrane that also includes virally-encoded membrane proteins.

The HIV genome encodes several structural proteins and has the characteristic 5'-LTR-Gag-Pol-Env-LTR-3' organization of the retrovirus family. The env gene encodes the viral envelope glycoprotein (Env) that is translated as a 160-kilodalton (kDa) precursor (gp160) and cleaved by a cellular protease to yield an external 120-kDa envelope glycoprotein (gp120) and a transmembrane 41-kDa envelope glycoprotein (gp41). These glycoproteins are required for HIV to infect cells.

Mature gp120 wildtype (wt) protein have about 500 amino acids in the primary sequence. gp120 is heavily N-glycosylated giving rise to an apparent molecular weight of 120 kD. The protein includes five conserved regions (C1-05) and five regions of high variability (V1-V5). Exemplary sequences of wt gp120 proteins are found in GENBANK®, for example accession numbers AAB05604 (SEQ ID NO: 1) and AAD12142 (SEQ ID NO: 2). It is understood that there are numerous variations in the sequence of gp120 from what is given in these examples. Reference to residues and mutation positions herein refer to HXB2 numbering, unless clearly noted to the contrary.

HIV infection begins when gp120 on the viral particle binds to CD4 and chemokine receptors on the cell membrane of a subject's target immune system cells (e.g., CD4+ T-cells, macrophages and dendritic cells). The bound virus then fuses with the target cell and reverse transcribes its RNA genome. The resulting viral DNA integrates into the subject cell's genome and begins to produce new viral RNA, resulting in new viral proteins and virions. The virions leave the originally infected cell to then infect new cells. This process kills the originally infected cell.

HIV-1 broadly neutralizing antibodies (bNAbs) are antibodies capable of neutralizing HIV. HIV bNAbs target four major areas of the Env: (i) the membrane proximal external region of the gp41 subunit; (ii) the CD4 receptor-binding site (CD4-BS); (iii) two sites including both carbohydrate and amino acid moieties, one at the base of the "V3" and another on the "V1/V2" loops of the gp120 subunit; and (iv) regions spanning elements of both gp120 and gp41.

Based on their ontogenies and mode of recognition, the CD4-BS bNAbs are grouped into two major types: (i) heavy chain complementary determining region three (CDRH3)-dominated; and (ii) variable heavy (VH)-gene-restricted. Antibodies that make contact primarily through their CDRH3 regions are further subdivided into the CH103, HJ16, VRC13 and VRC16 classes while the VH-gene-restricted Abs include the VRC01- and the 8ANC131-class antibodies.

VRC01-class bNAbs protect non-human primates from experimental simian/human HIV (SHIV)-infection and humanized mice from HIV-1 infection. It was therefore thought that vaccine-elicited VRC01-class bNAbs would protect humans from HIV-1 infection. However, all efforts to elicit such antibodies by immunization in humans or wild type animals with recombinant Env (rEnv) have been unsuccessful.

One of the many important reasons for the lack of success is thought to be the inability of the Env proteins used as immunogens to engage B cell receptors (BCRs) that encode the germline (gl) of VRC01-class antibodies (e.g., "immature" or not fully developed Abs). Indeed maturation of these antibodies to full neutralizing Abs requires that they circumvent steric constraints on Env through extensive somatic hypermutation. For example, HIV-1 has evolved to avoid detection by gl B cells that give rise to VRC01-class bNAbs through development of specific N-linked glycosylation sites (NLGS) (for example, in Loop D and V5 of the gp120 subunit). As a consequence, recombinant Env proteins derived from diverse HIV-1 isolates are ineffective in binding to and stimulating B cells engineered to express the glBCR forms of VRC01-class bNAbs in vitro. Targeted disruption of conserved NLGS at position 276 in Loop D, and at positions 460 and 463 in V5 of the 426c clade C Env, however, permits binding and activation gl B cell lines expressing BCRS of two clonally-related VRC01-class bNAbs, VRC01 and NIH45-46 in vitro. These two BCRs represent a small subset of potential VRC01-class antibody progenitors. Thus, designing immunogens capable of recognizing a larger group of glVRC01-class BCRs should increase the chances of activating rare, naïve glVRC01-class B cells during human immunization.

Previous reports describe preparation of artificial gp120 proteins (in some instances called "engineered outer domain" or "eOD" proteins) for use as HIV vaccines. The previous reports also describe multimerizing the artificial gp120 proteins to enhance immunogenicity of the proteins, and more particularly, the VRC01 epitope of the proteins. It was envisioned that multimerized artificial gp120 proteins would stimulate gl B cells using multivalent avidity, and, further, that the addition of the larger particulate forms would mimic a virus-like symmetric presentation of epitopes, reduce immune responses to regions buried in the multimer, and enhance in vivo trafficking of the artificial gp120 proteins to lymph nodes.

These previous reports described eOD proteins that lack normally occurring loops. The eOD proteins were also multimerized as trimers, tetramers, and octamers using coiled-coil multimerization domains. From the trimers and tetramers, octamers, 24mers, 60mers, and 180mers were formed.

The present disclosure provides engineered and multimerized (e/m) human immunodeficiency virus (HIV) envelope glycoproteins (Env). The engineered Env can be provided as multimerized heptamers. The e/m Env glycoproteins can be derived from glycoprotein 120 (gp120) and can used as an HIV vaccine.

More particularly, the present disclosure provides specifically engineered gp120 sequences with particular multimerization strategies that expand the germline (gl) VRC01-class antibody-recognition potential of the Env. Importantly, B cells were inefficiently activated by soluble trimeric multimerization forms of the Env. Higher order multimeric forms, however, based on heptamers were effective, indicating usefulness as an HIV-1 vaccination. Of note, heptameric multimerized forms were produced using the C4b multimerization domain.

Particular embodiments of the e/m Env include the following mutations: N460D; N463D; S278R; G471S; V65C; S115C; removal of V1 and V2; V3 replacement with a flexible linker; and an N-terminal truncation. In particular embodiments, V1 refers to 131-152 and V2 refers to 161-196. In particular embodiments, removal of V1 and V2 loops includes removal of 123-196. In particular embodiments, V3 refers to 296-331. In particular embodiments, removal of V3 with a flexible linker replacement includes removal of 301-323 and replacement with GGSGSG (SEQ ID NO: 3). Particular embodiments exclude a mutation at position 276. Exclusion of a mutation at this position is unexpected because as previously stated, this position is an important NLGS site used by HIV to avoid B cell detection. Particular embodiments disclosed herein present the outer domain and the inner domain.

In addition to SEQ ID NO: 3, a number of flexible linkers can be used to replace V3. The linker sequence should not be significantly deleterious to the immunogenicity of the e/m Env, and may even be beneficial to immunogenicity. Particular exemplary linkers include flexible Gly-Ser linkers. Such linkers are known to those of skill in the art. One exemplary Gly-Ser linker includes Ac-Cys-Gly-Gly-Gly (SEQ ID NO: 122). Additional Gly-Ser linkers include GSTSGSGKPGSGEGSTKG (SEQ ID NO: 4) and SGRAHAG (SEQ ID NO: 5). Further examples include a linker that includes $(Gly)_n$, where n=1 to 10 (e.g., n=1, 2, 3, 4, 5, 6, 7, 8, 9, or 10; SEQ ID NO: 6); (Ser)$_n$, where n=1 to 10 (e.g., n=1, 2, 3, 4, 5, 6, 7, 8, 9, or 10; SEQ ID NO: 7), (Ala)$_n$, where n=1 to 10 (e.g., n=1, 2, 3, 4, 5, 6, 7, 8, 9, or 10; SEQ ID NO: 8), (Gly-Ser)$_n$, where n=1 to 10 (e.g., n=1, 2, 3, 4, 5, 6, 7, 8, 9, or 10; SEQ ID NO: 9), (Gly-Ser-Ser-Gly)$_n$, where n=1 to 10 (e.g., n=1, 2, 3, 4, 5, 6, 7, 8, 9, or 10; SEQ ID NO: 10), (Gly-Ser-Gly)$_n$, where n=1 to 10 (e.g., n=1, 2, 3, 4, 5, 6, 7, 8, 9, or 10; SEQ ID NO: 11), (Gly-Ser-Ser)$_n$, where n=1 to 10 (e.g., n=1, 2, 3, 4, 5, 6, 7, 8, 9, or 10; SEQ ID NO: 12), (Gly-Ala)$_n$, where n=1 to 10 (e.g., n=1, 2, 3, 4, 5, 6, 7, 8, 9, or 10; SEQ ID NO: 13), or any combination thereof.

An N-terminal truncation refers to a truncation at the N-terminal end of a naturally-occurring Env. In particular embodiments, the N-terminal truncation is before residue 49, 48, 47, 46, 45, 44, 43, 42, 41, 40 or 39. In particular embodiments, the N-terminal truncation is before residue 46, 45, 44, 43 or 42. In particular embodiments, the N-terminal truncation is before residue 44.

Particular embodiments include a C-terminal truncation. In particular embodiments, the C-terminal truncation is after residue 499, 498, 497, 496, 495, 494, 493, 492, 491, 490 or 389. In particular embodiments, the C-terminal truncation is after residue 496, 495, 494, 493 or 492. In particular embodiments, the C-terminal truncation is after residue 494.

In particular embodiments, the e/m Env is multimerized with a C4b multimerization domain. C4 binding protein (C4b) is the major inhibitor of the classical complement and lectin pathway. The complement system is a major part of innate immunity and is the first line of defense against invading microorganisms. Orchestrated by more than 60 proteins, its major task is to discriminate between host cells and pathogens and to initiate immune responses when necessary. It also recognizes necrotic or apoptotic cells. Hofmeyer et al., J Mol Biol. 2013 Apr. 26; 425(8):1302-17.

Full-length native C4b includes seven α-chains linked together by a multimerization (i.e., heptamerization) domain at the C-terminus of the α-chains. Blom et al., (2004) Mol Immunol 40: 1333-1346. One of the α-chains can be replaced by a β-chain in humans. The wild-type C4b multimerization domain is 57 amino acid residues in humans and 54 amino acid residues in mice. Forbes et al., PLoS One. 2012; 7(9): e44943. It contains an amphipathic α-helix region, which is necessary and sufficient for heptamerization, as well as two cysteine residues which stabilize the structure. Kask et al., (2002) Biochemistry 41: 9349-9357.

Immunization of mice with antigen and murine C4b can lead to the induction of auto-antibodies against murine C4b. Ogun et al., (2008) Infect Immun 76: 3817-3823 Ogun et al. tested the C4b α-chain multimerization domains from a variety of mammalian and avian species for adjuvant activity in mice without induction of auto-antibodies. All the C4b oligomerization domains tested formed soluble heptameric proteins, and induced higher antigen-specific antibody titers in mice than antigen alone or in Freund's adjuvant. The most immunogenic form, the C4b derived multimerization domain of IMX313, was a hybrid derived from the multimerization domains of the two chicken orthologues of the C4b α-chain. It was designed to minimize similarity to mammalian C4b α-chain domains and has less than 20% amino acid identity to human C4b. Ogun et al., (2008) infect Immun 76: 3817-3823. This sequence particularly therefore minimizes the potential for auto-antibody induction in humans, and is a candidate "molecular adjuvant" for enhancement of vaccine-induced immune responses in humans. Forbes et al., PLoS One. 2012; 7(9): e44943.

In the recombinant protein vaccine studies by Ogun et al., however, the antibody titers induced against antigen when fused to different C4b α-chain multimerization domains varied significantly. Forbes et al. concluded that the C4b α-chain multimerization domain can effectively adjuvant antigen-specific T cell responses to some, but not all, antigens when fused to their C-termini and delivered by an adenoviral vectored vaccine. Forbes et al. hypothesized that the varying adjuvant activity observed with the C4b α-chain multimerization domain from different species when fused to an antigen could be due to the variable stability and strength of multimers formed.

The current disclosure provides that engineered gp120 antigens fused to C4b multimerization domains provide enhanced immune system responses (e.g., B cell responses) over engineered gp120 antigen alone and over trimeric engineered gp120 multimers. The current disclosure also provides that C4b multimerization of gp120 can induce stronger immune responses against gp120 antigens than other multimerization domains, such as coiled-coil domains.

The sequences of a number of C4b domain proteins are available in the art. These include human C4b multimerization domains as well as a number of homologues of human C4b multimerization domain available in the art. There are two types of homologues: orthologues and paralogues. Orthologues are defined as homologous genes in different organisms, i.e. the genes share a common ancestor coincident with the speciation event that generated them. Paralogues are defined as homologous genes in the same organism derived from a gene, chromosome or genome duplication, i.e. the common ancestor of the genes occurred since the last speciation event.

GenBank indicates mammalian C4b multimerization domain homologues in species including chimpanzees, rhesus monkeys, rabbits, rats, dogs, horses, mice, guinea pigs, pigs, chicken, and cattle. Further C4b multimerization domains may be identified by searching databases of DNA or protein sequences, using commonly available search programs such as BLAST.

Particular C4b multimerization domains that can be used include:

| SEQ ID NO: | Sequence |
|---|---|
| 14 | SGRAHAGWETPEGCEQVLTGKRLMQCLPNPEDVKMALEVYKLSLE IEQLELQRDSARQSTLDKELVPR |
| 15 | KKQGDADVCGEVAYIQSVVSDCHVPTAELRTLLEIRKLFLEIQKL KVELQGLSKE |
| 16 | ETPEGCEQVLTGKRLMQCLPNPEDVKMALEVYKLSLEIEQLELQR DSARQSTLDKEL |
| 17 | WETPEGCEQVLTGKRLMQCLPNPEDVKMALEVYKLSLEIEQLELQ RDSARQSTLDKEL |
| 18 | CEQVLTGKRLMQCLPNPEDVKMALEVYKLSLEIEQLELQRDSARQ STLDKEL |
| 19 | ETPEGCEQVLTGKRLMQCLPNPEDVKMALEVYKLSLEIEQLELQR DSARQYTLDKEL |
| 20 | ETPEGCEQVLAGKRLMQCLPNPEDVKMALEVYKLSLEIEQLELQR DRARQSTLDKEL |
| 21 | ETPEGCEQVLAGKRLMQCLPNPEDVKMALEVYKLSLEIEQLELQR DRARQSTWDKEL |

| SEQ ID NO: | Sequence |
|---|---|
| 22 | EVPEGCEQVQAGRRLMQCLADPYEVKMALEVYKLSLEIELLELQR DKARKSSVLRQL |
| 23 | VVPEGCEHILKGRKTMQCLPNPEDVKMALEIYKLSLDIELLELQR DRAKESTVQSPV |
| 24 | EVPKDCEHVFAGKKLMQCLPNSNDVKMALEVYKLTLEIKQLQLQI DKAKHVDREL |
| 25 | EYPEDCEQVHEGKKLMQCLPNLEEIKLALELYKLSLETKLLELQI DKEKKAKAKYSI |
| 26 | EYPEDCEQVHEGKKLMECLPTLEEIKLALALYKLSLETNLLELQI DKEKKAKAKYST |
| 27 | EIAEGCEQVLAGRKIMQCLPKPEDVRTALELYKLSLEIKQLEKKL EKEEKCTPEVQE |
| 28 | EYPEGCEQVVTGRKLLQCLSRPEEVKLALEVYKLSLEIEILQTNK LKKEAFLLREREKNVTCDFNPE |
| 29 | EYPEGCEQVVTGRKLLKCLSRPEEVKLALEVYKLSLEIALLELQI DKPKDAS |
| 30 | EVPENCEQVIVGKKLMKCLSNPDEAQMALQLYKLSLEAELLRLQI VKARQGS |
| 31 | EASEDLKPALTGNKTMQYVPNSHDVKMALEIYKLTLEVELLQLQI QKEKHTEAH |
| 32 | VSAEVCEAVFKGQKLLKCLPNAMEVKMALEVYKLSLEIEKLEQEK RKLEIA |
| 33 | EVPEECKQVAAGRKLLECLPNPSDVKMALEVYKLSLEIEQLEKEK YVKIQEKFSKKEMKQLTSALH |
| 34 | EVLEDCRIVSRGAQLLHCLSSPEDVHRALKVYKLFLEIERLEHQK EKWIQLHRKPQSMK |
| 35 | EGPEDCEIVNKGRQLLQCLSSPEDVQRALEVYKLSLEIERLEQQR EKRTSVHRKAHYTKVDGP |
| 36 | EAPEGCEQVLTGRKLMQCLPSPEDVKVALEVYKLSLEIKQLEKER DKLMNTHQKFSEKEEMKDLFFP |
| 37 | EVPEGCEQVLTGKKLMQCLPNPEDVKMALEVYKLSLEIELLELQI DKARQGS |
| 38 | GCEQVLTGKRLMQCLPNPEDVKMALEVYKLSLEIEQLELQRDSAR QS |
| 39 | ETPEGCEQVLTGKRLMQCLPNPEDVKMALEVYKLSLEIEQLELQR DSARQS |
| 40 | GSEQVLTGKRLMQSLPNPEDVKMALEVYKLSLEIEQLELQRDSAR QSTLDKEL |
| 41 | ETPEGCEQVLTGKRLMQCLPNPEDVKMALEIYKLTLEIEQLELQR DSARQSTLDKEL |
| 42 | ETPEGCEQVLTGKRLMQCLPNPEDVKMALEIYKLSLEIKQLELQR DSARQSTLDKEL |
| 43 | EGCEQILTGKRLMQCLPDPEDVKMALEIYKLSLEIKQLELQRDRA RQSTL |
| 44 | ETPEGCEQVLTGKRLMQCLPNPEDVKMALEVYKLSLEIKQLELQR DRARQSTLDKEL |
| 45 | EGCEQILTGKRLMQCLPNPEDVKMALEIYKLSLEIEQLELQRDRA RQSTLDK |
| 46 | WETPEGCEQVLTGKRLMQCLPNPEDVKMALEVYKLSLEIEQLELQ RDSARQSTLDKELVPR |

In particular embodiments, the C4b multimerization domain will be a multimerization domain which includes (i) glycine at position 12, (ii) alanine at position 28, (iii) leucines at positions 29, 34, 36, and/or 41; (iv) tyrosine at position 32; (v) lysine at position 33; and/or (vi) cysteine at positions 6 and 18. In particular embodiments, the C4b multimerization domain will be a multimerization domain which includes (i) glycine at position 12, (ii) alanine at position 28, (iii) leucines at positions 29, 34, 36, and 41; (iv) tyrosine at position 32; (v) lysine at position 33; and (vi) cysteine at positions 6 and 18.

C4b multimerization domains can include any of SEQ ID NOs: 14-46 with an N-terminal deletion of at least 1 consecutive amino acid residues (eg. at least 2, 3, 4, 5, 6, 7, 8, 9, 10 consecutive amino acid residues) in length. Additional embodiments can include a C-terminal deletion of at least 1 consecutive amino acid residues (eg. at least 2, 3, 4, 5, 6, 7, 8, 9, 10 consecutive amino acid residues) in length.

Particular C4b multimerization domain embodiments will retain or will be modified to include at least 1 of the following residues: A6; E11; A13; D21; C22; P25; A27; E28; L29; R30; T31; L32; L33; E34; I35; K37; L38; L40; E41; I42; Q43; K44; L45; E48; L49; or Q50. Further embodiments will retain or will be modified to include A6; E11; A13; D21; C22; P25; A27; E28; L29; R30; T31; L32; L33; E34; I35; K37; L38; L40; E41; I42; Q43; K44; L45; E48; L49; and Q50. Particular C4b multimerization domain embodiments will include the amino acid sequence "AELR".

Particular embodiments can utilize a heptamerization domain such as:

| SEQ ID NO: | Sequence |
|---|---|
| 47 | AHAGWETPEGCEQVLTGKRLMQCLPNPEDVKMA- LEVYKLSLEIEQLE LQRDSARQSTLDKEL (Human) |
| 48 | SKKQGDADVCGEVAYIQSVVSDCHVPTEDVKTL- LEIRKLFLEIQKLK VELQGLSKE (Chicken) |
| 49 | SKKQGDADVCGEVAYIQSVVSDCHVPT AELRTLLEIRKLFLEIQKLK VELQGLSKE (Modified Chicken) |

Particular embodiments include e/m Env that differ from previously engineered Env based on (i) the precise selection of mutations and (ii) the particular multimerization strategy. When (i) and (ii) are combined, an exemplary e/m Env includes:

| SEQ ID NO: | Sequence |
|---|---|
| 50 | VWKEAKTTLFCASDAKAYEKECH- NVWATHACVPTDPNPQEVVLENVT ENFNMWKNDMVDQMQEDVISIWDQCLKPCVKLTNT- STLTQACPKVTF DPIPIHYCAPAG- YAILKCNNKTFNGKGPCNNVSTVQCTHGIKPVVST QLLLNGSLAEEEIVIRSKNLRDNAKIIIVQLNKSVEIVC- TRPNNGGS GSGGDIRQAYCNISGRNWSEAVNQVKKKLKEHFPHKNIS- FQSSSGGD LEITTHSFNCGGEFFYCNTSGLFNDTISNATIMLPCRIKQI- INMWQE |

| SEQ ID NO: | Sequence |
|---|---|
| | VGKAIYAPPIKGNITCKSDITGLLLLRDGGDTTDNTEI-<br>FRPSGGDMR<br>DNWRSELYKYKVVEIKPLSGRAHAGWET-<br>PEGCEQVLTGKRLMQCLPN<br>PEDVKMALEVYKLSLEIEQLELQRDSARQSTLDKELVPR |

This e/m Env includes: the following mutations: N460D; N463D; S278R; G471S; V65C; S115C; removal of V1 and V2; V3 replacement with a flexible linker; an N-terminal truncation from 44, a C-terminal truncation after 494 and a C4b multimerization domain (see FIG. 2, SEQ ID NO: 134). This e/m Env excludes a mutation at position 276.

The present disclosure also encompasses other engineered Env multimerized with a C4b binding protein multimerization domain. For example, the C4b multimerization strategy can be used with any engineered Env when C4b multimerization generates a statistically significantly increase in an immunization effect. A statistically significantly increase in an immunization effect can be confirmed by B cell activation as measured by calcium flux and/or by staining bone marrow cells for IgD and IgM to identify mature B cell populations. While C4b multimerization is preferred, in particular embodiments, dextrameric and ferritin-based multimerization can also be used. An exemplary ferritin fusion sequence includes, for example, PMID 26279189. In particular embodiments, a ferritin fusion sequence includes

| SEQ ID NO: | Sequence |
|---|---|
| 51 | VWKEAKTTLFCASDAKAYEKECHNVWATHACVPTDPNPQEVVLENV<br>TENFNMWKNDMVDQMQEDVISIWDQCLKPCVKLTNTSTLTQACPKV<br>TFDPIPIHYCAPAGYAILKCNNKTFNGKGPCNNVSTVQCTHGIKPV<br>VSTQLLLNGSLAEEEIVIRSKNLRDNAKIIIVQLNKSVEIVCTRPN<br>NGGSGSGGDIRQAYCNISGRNWSEAVNQVKKKLKEHFPHKNISFQS<br>SSGGDLEITTHSFNCGGEFFYCNTSGLFNDTISNATIMLPCRIKQI<br>INMWQEVGKAIYAPPIKGNITCKSDITGLLLLRDGGDTTDNTEIFR |
| | PSGGDMRDNWRSELYKYKVVEIKPLGSGGSGESQVRQQFSKDIEKL<br>LNEQVNKEMQSSNLYMSMSSWCYTHSLDGAGLFLFDHAAEEYEHAK<br>KLIIPLNENNVPVQLTSISAPEHKFEGLTQIFQKAYEHEQHISESI<br>NNIVDHAIKSKDHATFNFLQVVYVAEQHEEEVLFKDILDKIELIGN<br>ENHGLYLADQYVKGIAKSRKSGS |

Particular engineered gp120 sequences useful within the present disclosure also include those that (i) maintain high affinity for broadly neutralizing antibodies b12 and VRC01; (ii) bind with little or no detectable affinity to CD4 or non-neutralizing CD4bs antibodies such as b6, b13, F105, 15e, m14 or m18; (iii) lack the V3 loop and beta 20/21 hairpin and are minimal in size (175 residues compared to 230 for wild-type outer domain); (iv) display no or low evidence of aggregation; (v) have N and C termini located distal from the CD4bs to allow coupling, by chemical or genetic means, to larger particles for the purpose of multimeric display; and/or (vi) may be expressed with a minimum of only two (2) glycans which may be useful for manipulating immune responses.

In particular embodiments, high affinity means that a binding domain associates with its target epitope with a dissociation constant ($1(D)$) of $10^{-5}$ M or less, in one embodiment of from $10^{-5}$ M to $10^{-13}$ M, or in one embodiment of from $10^{-5}$ M to $10^{-10}$ M. In particular embodiments, high affinity means that a binding domain associates with its target epitope with a dissociation constant ($1(D)$) of $10^{-7}$ M or less, or in one embodiment of from $10^{-7}$ M to $10^{-12}$ M, or in one embodiment of from $10^{-7}$ M to $10^{-15}$ M. In particular embodiments, high affinity means that a binding domain associates with its target epitope with an association constant presented in FIG. 15 or within a standard deviation of an association constant presented in FIG. 15.

In particular embodiments, little or no detectable affinity means that the binding domain associates with its target epitope with a dissociation constant (KD) of $10^{-4}$ M or more, in one embodiment of from $10^{-4}$ M to 1 M.

Exemplary engineered Env that can be multimerized with C4b, ferritin, and/or other heptamerization domains include:

| SEQ ID NO: | Sequence |
|---|---|
| 52 | VWKEAKTTLFCASDAKAYEKECHNVWATHACVPTDPNPQEVVLENVTENFNM<br>WKNDMVDQMQEDVISIWDQCLKPCVKLTNTSTLTQACPKVTFDPIPIHYCAPAG<br>YAILKCNNKTFNGKGPCNNVSTVQCTHGIKPVVSTQLLLNGSLAEEEIVIRSKNL<br>RDNAKIIIVQLNKSVEIVCTRPNNGGSGSGGDIRQAYCNISGRNWSEAVNQVKK<br>KLKEHFPHKNISFQSSSGGDLEITTHSFNCGGEFFYCNTSGLFNDTISNATIMLP<br>CRIKQIINMWQEVGKAIYAPPIKGNITCKSDITGLLLLRDGGDTTDNTEIFRPSGG<br>DMRDNWRSELYKYKVVEIKPL |
| 53 | RPVVSTQLLLNGSLAEEEVVIRSVNFTDNAKTIIVQLNTSVEINCTGAGHCNISRA<br>KWNNTLKQIASKLREQFGNNKTIIFKQSSGGDPEIVTHSFNCGGEFFYCDSTQLF<br>NSTWFNSTWSTEGSNNTEGSDTITLPCRPAPPPHCSSNITGLLLTRDGGNSNN<br>ESEIFRPGGGDMRDNWRSE |
| 54 | RPVVSTQLLLNGSLAEEEVVIRSVNFTDNAKTIIVQLNTSVEINCTGAGHCNISRA<br>KWNNTLKQIASKLREQFGNNKTIIFKQSSGGDPEIVTHSFNCGGEFFYCNSTQLF<br>NSTWFNSTWSTEGSNNTEGSDTITLPCRPAPPPHCSSNITGLLLTRDGGNSNN<br>ESEIFRPGGGDMRDNWRSE |
| 55 | DTITLPCRPAPPPHCSSNITGLLLTRDGGNSNNESEIFRPGGGDMRDNWRSGLS<br>GPVVSTQLLLNGSLAEEEVVIRSVNFTDNAKTIIVQLNTSVEINCTGAGHCNISRA<br>KWNNTLKQIASKLREQFGNNKTIIFKQSSGGDPEIVTHSFNCGGEFFYCDSTQLF<br>NSTWFNSTWS |
| 56 | GEFFYCDSTQLFNSTWFNSTWSTEGSNNTEGSDTITLPCRPAPPPHCSSNITGL<br>LLTRDGGNSNNESEIFRPGGGDMRDNWRSGLSGPVVSTQLLLNGSLAEEEVVI<br>RSVNFTDNAKTIIVQLNTSVEINCTGAGHCNISRAKWNNTLKQIASKLREQFGNN<br>KTIIFKQSSGGDPEIVTHSFNCG |

| SEQ ID NO: | Sequence |
|---|---|
| 57 | DTITLPCRPAPPPHCSSNITGLILTRDGGNSNNESEIFRPGGGDMRDIARCQIAG<br>TVVSTQLLLNGSLAEEEVVIRSVNFTDNAKSICVQLNTSVEINCTGAGHCNISRAK<br>WNNTLKQIASKLREQFGNNKTIIFKQSSGGDPEIVTHSFNCGGEFFYCDSTQLFN<br>STWFNSTWS |
| 58 | DTITLPCRPAPPPHCSSNITGLILTRDGGNSNNESEIFRPGGGDMRDIARCQIAG<br>TVVSTQLLLNGSLAEEEVVCRSVNFTDNAKSICVQLNTSVEINCTGAGHCNISRA<br>KWNNTLKQIASCLREQFGNNKTIIFKQSSGGDPEIVTHSFNCGGEFFYCDSTQLF<br>NSTWFNSTWS |
| 59 | DTITLPCRPAPPPHCSSNITGLILTRDGGNSNNESEIFRPGGGDMAGMPRCGGG<br>AVSTQLLLNGSLAEEEVVCRSVNFTDNAKSICVQLNTSVEINCTGAGHCNISRAK<br>WNNTLKQIASCLREQFGNNKTIIFKQSSGGDPEIVTHSFNCGGEFFYCDSTQLF<br>NSTWF |
| 60 | DTITLPCRPAPPPHCSSNITGLILTRDGGNSNDESEIFRPGGGDMRDIARCQIAG<br>TVVSTQLLLNGSLAEEEVVIRSVDFTDNAKSICVQLDTSVEIDCTGAGHCDISRAK<br>WDNTLKQIASKLREQFGNDKTIIFKQSSGGDPEIVTHSFNCGGEFFYCDSTQLFD<br>STWFDSTWS |
| 61 | GEFFYCDSTQLFNSTWFNSTWSTEGSNNTEGSDTITLPCRPAPPPHCSSNITGL<br>ILTRDGGNSNNESEIFRPGGGDMRDIARCQIAGTVVSTQLLLNGSLAEEEVVIRS<br>VNFTDNAKSICVQLNTSVEINCTGAGHCNISRAKWNNTLKQIASKLREQFGNNK<br>TIIFKQSSGGDPEIVTHSFNCG |
| 62 | GEFFYCDSTQLFNSTWFNSTWSTEGSNNTEGSDTITLPCRPAPPPHCSSNITGL<br>ILTRDGGNSNNESEIFRPGGGDMRCGARSGIAGTVVSTQLLLNGSLAEEEVVIR<br>SVNFTDNAKCIIVQLNTSVEINCTGAGHCNISRAKWNNTLKQIASKLREQFGNNK<br>TIIFKQSSGGDPEIVTHSFNCG |
| 63 | GEFFYCDSTQLFNSTWFNSTWSTEGSNNTEGSDTITLPCRPAPPPHCSSNITGL<br>ILTRDGGNSNNESEIFRPGGGDMRDIARCQIAGTVVSTQLLLNGSLAEEEVVCR<br>SVNFTDNAKSICVQLNTSVEINCTGAGHCNISRAKWNNTLKQIASCLREQFGNN<br>KTIIFKQSSGGDPEIVTHSFNCG |
| 64 | DTITLPCRPAPPPHCSSNITGLILTRDGGNSNNESEIFRPGGGDMRDIARCQIAG<br>TVVSTQLLLNGSLAEEEVVIRSVNFTDNAKSICVQLNTSVEINCTGAGHCNISRAK<br>WNNTLKQIASKLREQFGNNKTIIFKQSSGGDPEIVTHSFNCGGEFFYCNSTQLFN<br>STWFNSTWS |
| 65 | DTITLPCRPAPPPHCSSNITGLILTRDGGNSNNESEIFRPGGGDMRDIARCQIAG<br>TVVSTQLLLNGSLAEEEVVIRSVDFTDNAKSICVQLNTSVEINCTGAGHCNISRAK<br>WNNTLKQIASKLREQFGNNKTIIFKQSSGGDPEIVTHSFNCGGEFFYCNSTQLFN<br>STWFNSTWS |
| 66 | DTITLPCRPAPPPHCSSNITGLILTRDGGNSNDESEIFRPGGGDMRDIARCQIAG<br>TVVSTQLLLNGSLAEEEVVIRSVDFTDNAKSICVQLNTSVEINCTGAGHCNISRAK<br>WNNTLKQIASKLREQFGNNKTIIFKQSSGGDPEIVTHSFNCGGEFFYCNSTQLFN<br>STWFNSTWS |
| 67 | DTITLPCRPAPPPHCSSNITGLILTRDGGNSNNESEIFRPGGGDMRDIARCQIAG<br>TVVSTQLFLNGSLAEEEVVIRSVNFTDNAKSICVQLNTSVEINCTGAGHCNISRA<br>KWNNTLKQIASKLREQFGNNKTIIFKQSSGGDPEIVTHSFNCGGEFFYCNSTQLF<br>NSTWFNSTWS |
| 68 | DTITLPCRPAPPPHCSSNITGLILTRDGGNSNNESEIFRPGGGDMRDIARCQIAG<br>TVVSTQLFLNGSLAEEEVVIRSVDFTDNAKSICVQLNTSVEINCTGAGHCNISRA<br>KWNNTLKQIASKLREQFGNNKTIIFKQSSGGDPEIVTHSFNCGGEFFYCNSTQLF<br>NSTWFNSTWS |
| 69 | DTITLPCRPAPPPHCSSNITGLILTRDGGNSNDESEIFRPGGGDMRDIARCQIAG<br>TVVSTQLFLNGSLAEEEVVIRSVDFTDNAKSICVQLNTSVEINCTGAGHCNISRA<br>KWNNTLKQIASKLREQFGNNKTIIFKQSSGGDPEIVTHSFNCGGEFFYCNSTQLF<br>NSTWFNSTWS |
| 70 | DTITLPCRPAPPPHCSSNITGLILTRDGGNSNNESEIFRPGGGDMRDNARCQIAG<br>TVVSTQLLLNGSLAEEEVVIRSVNFTDNAKSICVQLNTSVEINCTGAGHCNISRAK<br>WNNTLKQIASKLREQFGNNKTIIFKQSSGGDPEIVTHSFNCGGEFFYCNSTQLFN<br>STWFNSTWS |
| 71 | DTITLPCRPAPPPHCSSNITGLILTRDGGNSNNESEIFRPGGGDMRDIARCQIAG<br>TVVSTQLLLNGSLAEEEVVIRSVNFTDNAKSICVQLNTSVEINCTGAGHCNISRAK<br>WNNTLKQIASKLREQFGNKTIIFKQSSGGDPEIVTHSFNCGGEFFYCNSTQLFNS<br>TWFNSTWS |

| SEQ ID NO: | Sequence |
|---|---|
| 72 | DTITLPCRPAPPPHCSSNITGLILTRDGGNSNNESEIFRPGGGDMRDIARCQIAG TVVSTQLLLNGSLAEEEVIRSVNFTDNAKSICVQLNTSVEINCTGAGHCNISRAK WNNTLKQIASKLREQFGNNKTIIFKQSSGGDPEIVTHSFNCGGEFFYCNTTQLFN STWFNSTWS |
| 73 | DTITLPCRPAPPPHCSSNITGLILTRDGGNSNNESEIFRPGGGDMRDIARCQIAG TVVSTQLLLNGSLAEEEIVIRSVNFTDNAKSICVQLNTSVE1NCTGAGHCNISRAK WNNTLKQIASKLREQFGNNKTIIFKQSSGGDPEIVTHSFNCGGEFFYCNSTQLFN STWFNSTWS |
| 74 | DTITLPCRPAPPPHCSSNITGLILTRDGGNSNNESEIFRPGGGDMRDIARCQIAG TVVSSQLFLNGSLAEEEVVIRSVNFTDNAKSICVQLNTSVEINCTGAGHCNISRA KWNNTLKQIASKLREQFGNNKTIIFKQSSGGDPEIVTHWFNCGGEFFYCNSTQL FNSTWFNSTWS |
| 75 | DTITLPCRPAPPPHCSSNITGLILTRDGGNSNNESEIFRPGGGDMRDIARCQIAG TVVSSQLFLNGSLAEEEVVIRSVDFTDNAKSICVQLNTSVEINCTGAGHCNISRA KWNNTLKQIASKLREQFGNNKTIIFKQSSGGDPEIVTHWFNCGGEFFYCNSTQL FNSTWFNSTWS |
| 76 | DTITLPCRPAPPPHCSSNITGLILTRDGGNSNDESEIFRPGGGDMRDIARCQIAG TVVSSQLFLNGSLAEEEVVIRSVDFTDNAKSICVQLNTSVEINCTGAGHCNISRA KWNNTLKQIASKLREQFGNNKTIIFKQSSGGDPEIVTHWFNCGGEFFYCNSTQL FNSTWFNSTWS |
| 77 | DTITLPCRPAPPPHCSSNITGLILTRDGGTSDDKTEIFRPGGGDMRDIARCQIAGT VVSTQLLLNGSLAEEEVVIRSEDFRDNAKSICVQLNTSVEINCTGAGHCNISRAK WNNTLKQIASKLREQFGNKTIIFKQSSGGDPEFVTHSFNCGGEFFYCDSTQLFD STWFDSTWS |
| 78 | DTITLPCRPAPPPHCSSNITGLILTRGGGISDDKTEIFRPGGGDMRDIARCQIAGT VVSTQLLLNGSLAEEEVVIRSEDFRDNSKSICVQLNTSVEINCTGAGHCNISRAK WNNTLKQIASKLREQFGNKTIIFSQSLGGDPEFVTHSFNCGGEFFYCDSTQLFD STWFDSTWS |
| 79 | DTITLPCRPAPPPHCSSNITGLILTRGGGISDDKTEIFRPGGGDMRDIARCQIAGT VVSTQLLLNGSLAEEEVVIRSENFTDNSKSICVQLNTSVEINCTGAGHCNISRAK WNNTLKQIASKLREQFGNKTIIFSQSLGGDPEFVTHSFNCGGEFFYCDSTQLFD STWFDSTWS |
| 80 | DTITLPCRPAPPPHCSSNITGLILTRGGGISDDKTEIFRPSGGDMRDIARCQIAGT VVSTQLLLNGSLAEEEVVIRSEDFRDNSKSICVQLNTSVEINCTGAGHCNISRAK WNNTLKQIASKLREQFGNKTIIFSQSLGGDPEFVTHSFNCGGEFFYCDSTQLFD STWFDSTW |
| 81 | DTITLPCRPAPPPHCSSNITGLILTRGGGISDDKTEIFRPGGGDMRDIARCQIAGT VVSTQLLLNGSLAEEEVVIRSEDFRDNSKSICVQLNTSVEINCTGAGHCNISRAK WNNTLKQIASKLREQFGNRTIIFSQSLGGDPEFVTHSFNCGGEFFYCDSTQLFD STWFDSTW |
| 82 | DTITLPCRPAPPPHCSSNITGLILTRGGGISDDDTEIFRPSGGDMRDIARCQIAGT VVSTQLFLNGSLAEEEVVIRSEDFRDNSKSICVQLNTSVEINCTGAGHCNISRAK WNNTLKQIASKLREQFGNRTIIFSQSLGGDPEFVTHSFNCGGEFFYCDSTQLFD STWFDSTW |
| 83 | DTITLPCRPAPPPHCSSNITGLILTRAGGISDDNTEIFRPSGGDMRDIARCQIAGT VVSTQLFLNGSLAEEEVVIRSEDFRDNSKSICVQLNTSVEINCTGAGHCNISRAK WNNTLKQIASKLREQFGNRTIIFSQSLGGDPEFVTHSFNCGGEFFYCDSTQLFD STWFDSTW |
| 84 | DTITLPCRPAPPPHCSSNITGLILTRGGGISDDNTEIFRPSGGDMRDIARCQIAGT VVSTQLLLNGSLAEEEVVIRSEDFRDNSKSICVQLNTSVEINCTGAGHCNISRAK WNNTLKQIASKLREQFGNRTIIFSQSLGGDPEFVTHSFNCGGEFFYCDSTQLFD STWFDSTW |
| 85 | DTITLPCRPAPPPHCSSNITGLILTRGGGVSDDDTEIFRPSGGDMRDIARCQIAG TVVSTQLFLNGSLAEEEVVIRSVDFRDNAKSICVQLNTSVEINCTGAGHCNISRA KWNNTLKQIASKLREQFGNRTIIFSQSSGGDPEFVTHSFNCGGEFFYCDSTQLF DSTWFDSTW |
| 86 | DTITLPCRPAPPPHCSSNITGLILTRGGGVSDDDTEIFRPAGGDMRDIARCQIAG TVVSTQLFLNGSLAEEEVVIRSVDFRDNAKSICVQLNTSVEINCTGAGHCNISRA KWNNTLKQIASKLREQFGNRTIIFSQSSGGDPEFVTHSFNCGGEFFYCDSTQLF DSTWFDSTW |

| SEQ ID NO: | Sequence |
|---|---|
| 87 | DTITLPCRPAPPPHCSSNITGLILTRGGGVSDDDTEIFRPSGGDMRDIARCQIAG<br>TVVSTQLFLNGSLAEEEVVIRSVDFRDNAKSICVQLNTSVEINCTGAGHCNISRA<br>KWNNTLKQIASKLREQFGNRTIIFSQSSGGDPEFVTHSFNCGGEFFYCDSTQLF<br>DSTWFD |
| 88 | DTITLPCRPAPPPHCSSNITGLILTRDGGVSNDETEIFRPSGGDMRDIARCQIAGT<br>VVSTQLFLNGSLAEEEVVIRSVDFRDNAKSICVQLNTSVEINCTGAGHCNISRAK<br>WNNTLKQIASKLREQFGNRTIIFKQSSGGDPEFVTHSFNCGGEFFYCDSTQLFN<br>STWFNST |
| 89 | DTITLPCRPAPPPHCSSNITGLILTRDGGNSNDETEIFRPSGGDMRDIARCQIAGT<br>VVSTQLFLNGSLAEEEVVIRSVDFRDNAKSICVQLNTSVEINCTGAGHCNISRAK<br>WNNTLKQIASKLREQFGNRTIIFKQSSGGDPEFVTHSFNCGGEFFYCDSTQLFN<br>STWFNST |
| 90 | DTITLPCRPAPPPHCSSNITGLILTRDGGVSNDESEIFRPSGGDMRDIARCQIAGT<br>VVSTQLFLNGSLAEEEVVIRSVDFRDNAKSICVQLNTSVEINCTGAGHCNISRAK<br>WNNTLKQIASKLREQFGNRTIIFKQSSGGDPEFVTHSFNCGGEFFYCDSTQLFN<br>STWFNST |
| 91 | DTITLPCRPAPPPHCSSNITGLILTRDGGVSNDETEIFRPGGGDMRDIARCQIAG<br>TVVSTQLFLNGSLAEEEVVIRSVDFRDNAKSICVQLNTSVEINCTGAGHCNISRA<br>KWNNTLKQIASKLREQFGNRTIIFKQSSGGDPEFVTHSFNCGGEFFYCDSTQLF<br>NSTWFNST |
| 92 | DTITLPCRPAPPPHCSSNITGLILTRDGGVSNDETEIFRPSGGDMRDIARCQIAGT<br>VVSTQLLLNGSLAEEEVVIRSVDFRDNAKSICVQLNTSVEINCTGAGHCNISRAK<br>WNNTLKQIASKLREQFGNRTIIFKQSSGGDPEFVTHSFNCGGEFFYCDSTQLFN<br>STWFNST |
| 93 | DTITLPCRPAPPPHCSSNITGLILTRDGGVSNDETEIFRPSGGDMRDIARCQIAGT<br>VVSTQLFLNGSLAEEEVVIRSVDFTDNAKSICVQLNTSVEINCTGAGHCNISRAK<br>WNNTLKQIASKLREQFGNRTIIFKQSSGGDPEFVTHSFNCGGEFFYCDSTQLFN<br>STWFNST |
| 94 | DTITLPCRPAPPPHCSSNITGLILTRDGGVSNDETEIFRPSGGDMRDIARCQIAGT<br>VVSTQLFLNGSLAEEEVVIRSVDFRDNAKSICVQLNTSVEINCTGAGHCNISRAK<br>WNNTLKQIASKLREQFGNKTIIFKQSSGGDPEFVTHSFNCGGEFFYCDSTQLFN<br>STWFNST |
| 95 | DTITLPCRPAPPPHCSSNITGLILTRDGGVSNDETEIFRPSGGDMRDIARCQIAGT<br>VVSTQLFLNGSLAEEEVVIRSVDFRDNAKSICVQLNTSVEINCTGAGHCNISRAK<br>WNNTLKQIASKLREQFGNRTIIFKQSSGGDPEIVTHSFNCGGEFFYCDSTQLFNS<br>TWFNST |
| 96 | DTITLPCRPAPPPHCSSNITGLILTRDGGVSNDETEIFRPSGGDMRDIARCQIAGT<br>VVSTQLFLNGSLAEEEVVIRSVDFRDNAKSICVQLDTSVEIDCTGAGHCDISRAK<br>WDNTLKQIASKLREQFGDRTIIFKQSSGGDPEFVTHSFNCGGEFFYCDSTQLFD<br>STWFDST |
| 97 | DTITLPCRPAPPPHCSSNITGLILTRDGGVSNNETEIFRPSGGDMRDIARCQIAGT<br>VVSTQLFLNGSLAEEEVVIRSVDFRDNAKSICVQLNTSVEINCTGAGHCNISRAK<br>WNNTLKQIASKLREQFGNRTIIFKQSSGGDPEFVTHSFNCGGEFFYCNSTQLFN<br>STWFNST |
| 98 | DTITLPCRPAPPPHCSSNITGLILTRDGGNSNNETEIFRPSGGDMRDIARCQIAGT<br>VVSTQLFLNGSLAEEEVVIRSVDFRDNAKSICVQLNTSVEINCTGAGHCNISRAK<br>WNNTLKQIASKLREQFGNRTIIFKQSSGGDPEFVTHSFNCGGEFFYCNSTQLFN<br>STWFNST |
| 99 | DTITLPCRPAPPPHCSSNITGLILTRDGGVSNNETEIFRPGGGDMRDIARCQIAG<br>TVVSTQLFLNGSLAEEEVVIRSVDFRDNAKSICVQLNTSVEINCTGAGHCNISRA<br>KWNNTLKQIASKLREQFGNRTIIFKQSSGGDPEFVTHSFNCGGEFFYCNSTQLF<br>NSTWFNST |
| 100 | DTITLPCRPAPPPHCSSNITGLILTRDGGVSNNETEIFRPSGGDMRDIARCQIAGT<br>VVSTQLLLNGSLAEEEVVIRSVDFRDNAKSICVQLNTSVEINCTGAGHCNISRAK<br>WNNTLKQIASKLREQFGNRTIIFKQSSGGDPEFVTHSFNCGGEFFYCNSTQLFN<br>STWFNST |
| 101 | DTITLPCRPAPPPHCSSNITGLILTRDGGVSNNETEIFRPSGGDMRDIARCQIAGT<br>VVSTQLFLNGSLAEEEVVIRSVDFTDNAKSICVQLNTSVEINCTGAGHCNISRAK<br>WNNTLKQIASKLREQFGNRTIIFKQSSGGDPEFVTHSFNCGGEFFYCNSTQLFN<br>STWFNST |

| SEQ ID NO: | Sequence |
|---|---|
| 102 | DTITLPCRPAPPPHCSSNITGLILTRDGGVSNNETEIFRPSGGDMRDIARCQIAGT VVSTQLFLNGSLAEEEVVIRSVDFRDNAKSICVQLNTSVEINCTGAGHCNISRAK WNNTLKQIASKLREQFGNKTIIFKQSSGGDPEFVTHSFNCGGEFFYCNSTQLFN STWFNST |
| 103 | DTITLPCRPAPPPHCSSNITGLILTRDGGVSNNETEIFRPSGGDMRDIARCQIAGT VVSTQLFLNGSLAEEEVVIRSVDFRDNAKSICVQLNTSVEINCTGAGHCNISRAK WNNTLKQIASKLREQFGNRTIIFKQSSGGDPEIVTHSFNCGGEFFYCNSTQLFNS TWFNST |
| 104 | DTITLPCRPAPPPHCSSNITGLILTRDGGVSNNETEIFRPSGGDMRDIARCQIAGT VVSTQLFLNGSLAEEEVVIRSVNFTDNAKSICVQLNTSVEINCTGAGHCNISRAK WNNTLKQIASKLREQFGNRTIIFKQSSGGDPEFVTHSFNCGGEFFYCNSTQLFN STWFNST |
| 105 | DTITLPCRPAPPPHCSSNITGLILTRAGGVSDNNTEIFFPSGGDMRDIARCQIAGT VVSTQLFLNGSLAEEEVVIRSVDFRDNAKSICVQLNTSVEINCTGAGHCNISRAK WNNTLKQIASKLREQFGNRTIIFSQSTGGDPEFVTHSFNCGGEFFYCNSTQLFN STWFNST |
| 106 | DTITLPCRPAPPPHCSSNITGLILGRAGGASDDNTEIFYPSGGDMRDIARCQIAG TVVSTQLFLNGSLAEEEVVIRSVDFRDNAKSICVQLNTSVEINCTGAGHCNISRA KWNNTLKQIASKLREQFGNRTIIFSQSTGGDPEIVTHSFNCGGEFFYCNSTQLFN STWFNSTW |
| 107 | DTITLPCRPAPPPHCSSNITGLILTRAGGVSNNETEIFFPSGGDMRDIARCQIAGT VVSTQLFLNGSLAEEEVVIRSVDFRDNAKSICVQLNTSVEINCTGAGHCNISRAK WNNTLKQIASKLREQFGNRTIIFKQSSGGDPEFVTHSFNCGGEFFYCNSTQLFN STWFNST |
| 108 | VWKEATTTLFCASDAKAYDTEVHNVWATHACVPTDPNPQEVELENVTENFNM WKNNMVEQMHEDIISLWDQSLKPCVKLTGGSVITQACPKISFEPIPIHYCAPAGF AILKCKDKKFNGKGPCSNVSTVQCTHGIRPVVSTQLLLNGSLAEEEVVIRSENFA DNAKTIIVQLNESVEINCTRPNNGGSGSGGDIRQAHCNLSRAKWNDTLNKIVIKL REQFGNKTIVFKHSSGGDPEIVTHSFNCGGEFFYCNSTQLFNSTWNVTEESNN TVENNTITLPCRIKQIINMWQKVGRAMYAPPIRGQIRCSSNITGLLLTRDGGPEDN KTEVFRPGGGDMRDNWRSELYKYKVVKIE |
| 109 | VWKDATTTLFCASDAKAHETEVHNVWATHACVPTDPNPQEVELKNVTENFNM WKNNMVEQMHEDIISLWDQSLKPCVKLTGGSVITQACPKVSFEPIPIHYCAPAG FAILKCKDKKFNGKGPCSNVSTVQCTHGIRPVVSTQLLLNGSLAEEEVVIRSEDF RNNAKIIIVQLNESVEINCTGAGHCNLSRAKWNDTLNKIVIKLREQFGNKTIVFKH SSGGDPEIVTHSFNCGGEFFYCNSTQLFNSTWNVTEESNNTVENNTITLPCRIK QIINMWQEVGRAMYAPPIRGQIRCSSNI |
| 110 | DTITLPCRPAPPPHCSSNITGLILTRDGGNSNNESEIFRPGGGDMRDIANCSIAG TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGGEFFYCNSTQLFN STWFNSTWS |
| 111 | DTITLPCRPAPPPHCSSNITGLILTRDGGNSNNESEIFRPGGGDMRDIARCQNAS TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGGEFFYCNSTQLFN STWFNSTWS |
| 112 | DTITLPCRPAPPPHCSSNITGLILTRDGGNSNNESEIFRPGGGDMRDIARCQIAG NVTSTQLLLNGSLAEEEVVIRSVNFTDNAKSICVQLNTSVEINCTGAGHCNISRA KWNNTLKQIASKLREQFGNNKTIIFKQSSGGDPEIVTHSFNCGGEFFYCNSTQLF NSTWFNSTWS |
| 113 | DTITLPCRPAPPPHCSSNITGLILTRDGGNSNNESEIFRPGGGDMRDIARCQIAG TVVSTQLLLNGSLAEEEVVIRSVNFTDNAKSICVQLNTSVEINCTGAGHCNISRAK WNNTLKQIASKLRENFSNNKTIIFKQSSGGDPEIVTHSFNCGGEFFYCNSTQLFN STWFNSTWS |
| 114 | DTITLPCNPSPPPHCSSNITGLILTRDGGNSNNESEIFRPGGGDMRDIARCQIAG TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGGEFFYCNSTQLFN STWFNSTWS |
| 115 | DTITLPCRNATPPHCSSNITGLILTRDGGNSNNESEIFRPGGGDMRDIARCQIAG TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGGEFFYCNSTQLFN STWFNSTWS |

-continued

| SEQ ID NO: | Sequence |
|---|---|
| 116 | DTITLPCRPAPPPHCSSNITGLILTRDGGNSNNESEIFRPGGGDMRDIARCQIAG TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGNETFYCNSTQLFN STWFNSTWS |
| 117 | DTITLPCNPSPPPHCSSNITGLILTRDGGNSNNESEIFRPGGGDMRDIARCQNAS TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGNETFYCNSTQLFN STWFNSTWS |
| 118 | DTITLPCNPSPPPHCSSNITGLILTRDGGNSNNESEIFRPGGGDMRDIANCSIAG TVVSTQLLLNGSLAEEEVVIRSVNFTDNAKSICVQLNTSVEINCTGAGHCNISRAK WNNTLKQIASKLREQFGNNKTIIFKQSSGGDPEIVTHSFNCGNETFYCNSTQLFN STWFNSTWS |
| 119 | DTITLPCNPSPPPHCSSNITGLILTRDGGNSNNESEIFRPGGGDMRDIANCSIAG NVTSTQLLLNGSLAEEEVVIRSVNFTDNAKSICVQLNTSVEINCTGAGHCNISRA KWNNTLKQIASKLREQFGNNKTIIFKQSSGGDPEIVTHSFNCGNETFYCNSTQLF NSTWFNSTWS |
| 120 | DTITLPCNPSPPPHCSSNITGLILTRDGGNSNNESEIFRPGGGDMRDIANCSIAG TVVSTQLLLNGSLAEEEVVIRSVNFTDNAKSICVQLNTSVEINCTGAGHCNISRAK WNNTLKQIASKLRENFSNNKTIIFKQSSGGDPEIVTHSFNCGNETFYCNSTQLFN STWFNSTWS |
| 121 | DTITLPCNPSPPPHCSSNITGLILTRDGGNSNNESEIFRPGGGDMRDIANCSIAG NVTSTQLLLNGSLAEEEVVIRSVNFTDNAKSICVQLNTSVEINCTGAGHCNISRA KWNNTLKQIASKLRENFSNNKTIIFKQSSGGDPEIVTHSFNCGNETFYCNSTQLF NSTWFNSTWS |

Within these examples, SEQ ID NOs: 53-63 are advantageous for the elicitation of CD4-binding site (CD4bs)-directed broadly-neutralizing antibodies (bnAbs). SEQ ID NOs: 64-76 are advantageous for improving binding of mature VRC01. SEQ ID NOs: 77-109 are advantageous for improving binding to gl VRC01 and/or other VI-11-2 antibodies. SEQ ID NOs: 110-121 are involved in glycan masking.

As will be understood by one of ordinary skill in the art, all sequences disclosed herein and all combinations of resulting e/m Env can additionally include additional amino acid sequences to include further beneficial attributes. For example, sequences disclosed herein can include tag peptides which in some embodiments can provide an epitope to which an anti-tag antibody can selectively bind. The epitope tag generally can be placed at the amino- or carboxyl-terminus of the e/m Env. However, in some embodiments, an epitope tag can be placed within the amino acid sequence of an e/m Env. In some embodiments, an epitope tag can be used as a linker to join a g120 peptide to a C4b multimerization domain or another peptide or another type of molecule. In some embodiments a linker can be Ac-Cys-Gly-Gly-Gly (SEQ ID NO: 122). The presence of such epitope-tagged forms of e/m Env can be detected using an antibody against the epitope tag. Also, provision of the epitope tag enables the e/m Env to be readily purified by affinity purification using an anti-tag antibody or another type of affinity matrix that binds to the epitope tag; this also can be useful for binding the e/m Env to a support for heterogeneous screening methods. Various tag polypeptides and their respective antibodies are well known in the art. Examples include poly-histidine (poly-his) or poly-histidine-glycine (poly-his-gly) tags (e.g., GSHHHHHH (SEQ ID NO: 123); GTKHHHHHH (SEQ ID NO: 124)); the flu HA tag polypeptide and its antibody 12CA5 (Field et al., Mol. Cell. Biol., 8:2159-2165 (1988)); the c-myc tag and the 8F9, 3C7, 6E10, G4, B7 and 9E10 antibodies thereto (Evan et al., Molecular and Cellular Biology, 5:3610-3616 (1985)); and the Herpes Simplex virus glycoprotein D (gD) tag and its antibody (Paborsky et al., Protein Engineering, 3(6):547-553 (1990)). Other tag polypeptides include the Flag-peptide (Hopp et al., BioTechnology, 6:1204-1210 (1988)); the KT3 epitope peptide (Martin et al., Science, 255:192-194 (1992)); tubulin epitope peptide (Skinner et al., J. Biol. Chem., 266:15163-15166 (1991)); and the T7 gene 10 protein peptide tag (Lutz-Freyermuth et al., Proc. Natl. Acad. Sci. USA, 87:6393-6397 (1990)).

In particular embodiments, the e/m Env include an intervening linker between the engineered Env and C4b multimerization domains. In general, the amino acids within the linker sequences are not deleterious to the immunogenicity of the fusion, and may even be beneficial to immunogenicity. Alternatively, a e/m Env can lack linker sequences, but for the linker sequence that replaces the V3 loop. Particular embodiments can include flexible linkers described elsewhere herein. In particular embodiments, rigid linker sequences, such as proline-rich sequences may also be used.

e/m Env may additionally include additional domains such as additional antigen or antigenic fragment (e.g., 2, 3, 4, 6, 8, 10 additional antigens or antigenic fragments). Additional antigen(s) or antigenic fragments may be the same as the gp120 domain of a particular embodiment or may be different.

"Variants" include protein sequences having one or more amino acid additions, deletions, stop positions, or substitutions, as compared to a protein sequence disclosed elsewhere herein.

An amino acid substitution can be a conservative or a non-conservative substitution. Variants of protein sequence disclosed herein can include those having one or more conservative amino acid substitutions. A "conservative substitution" or "conservative amino acid substitution" involves a substitution found in one of the following conservative substitutions groups: Group 1: Alanine (Ala; A), Glycine (Gly; G), Serine (Ser; S), Threonine (Thr; T); Group 2: Aspartic acid (Asp; D), Glutamic acid (Glu; E); Group 3: Asparagine (Asn; N), Glutamine (Gln; Q); Group 4: Arginine (Arg; R), Lysine (Lys; K), Histidine (His; H); Group 5: Isoleucine (Ile; I), Leucine (Leu; L), Methionine (Met; M), Valine (Val; V); and Group 6: Phenylalanine (Phe; F), Tyrosine (Tyr; Y), Tryptophan (Trp; W).

Additionally, amino acids can be grouped into conservative substitution groups by similar function, chemical structure, or composition (e.g., acidic, basic, aliphatic, aromatic, or sulfur-containing). For example, an aliphatic grouping may include, for purposes of substitution, G, A, V, L, and I. Other groups including amino acids that are considered conservative substitutions for one another include: sulfur-containing: M and C; acidic: D, E, N, and Q; small aliphatic, nonpolar or slightly polar residues: A, S, T, P, and G; polar, negatively charged residues and their amides: D, N, E, and Q; polar, positively charged residues: H, R, and K; large aliphatic, nonpolar residues: M, L, I, V, and C; and large aromatic residues: F, Y, and W.

Non-conservative substitutions include those that significantly affect: the structure of the peptide backbone in the area of the alteration (e.g., the alpha-helical or beta-sheet structure); the charge or hydrophobicity of the molecule at the target site; or the bulk of the side chain. Non-conservative substitutions which in general are expected to produce the greatest changes in the proteins's properties are those in which (i) a hydrophilic residue (e.g. S or T) can be substituted for (or by) a hydrophobic residue (e.g. L, I, F, V, or A); (ii) a C or P can be substituted for (or by) any other residue; (iii) a residue having an electropositive side chain (e.g. K, R, or H) can be substituted for (or by) an electronegative residue (e.g. Q or D); or (iv) a residue having a bulky side chain (e.g. F), can be substituted for (or by) one not having a bulky side chain, (e.g. G). Additional information is found in Creighton (1984) Proteins, W.H. Freeman and Company.

Variants of protein sequences disclosed herein also include proteins with at least 70% sequence identity, at least 80% sequence identity, at least 85% sequence identity, at least 90% sequence identity, at least 95% sequence identity, at least 96% sequence identity, at least 97% sequence identity, at least 98% sequence identity, or at least 99% sequence identity to a protein sequence disclosed herein.

Variants of proteins disclosed herein include proteins that share: 70% sequence identity with any of SEQ ID NOs: 1-124, 126, or 134-146 (and particularly SEQ ID NO: 50); 75% sequence identity with any of SEQ ID NOs: 1-124, 126, or 134-146 (and particularly SEQ ID NO: 50); 80% sequence identity with any of SEQ ID NOs: 1-124, 126, or 134-146 (and particularly SEQ ID NO: 50); 81% A sequence identity with any of SEQ ID NOs: 1-124, 126, or 134-146 (and particularly SEQ ID NO: 50); 82% sequence identity with any of SEQ ID NOs: 1-124, 126, or 134-146 (and particularly SEQ ID NO: 50); 83% sequence identity with any of SEQ ID NOs: 1-124, 126, or 134-146 (and particularly SEQ ID NO: 50); 84% sequence identity with any of SEQ ID NOs: 1-124, 126, or 134-146 (and particularly SEQ ID NO: 50); 85% sequence identity with any of SEQ ID NOs: 1-124, 126, or 134-146 (and particularly SEQ ID NO: 50); 86% sequence identity with any of SEQ ID NOs: 1-124, 126, or 134-146 (and particularly SEQ ID NO: 50); 87% sequence identity with any of SEQ ID NOs: 1-124, 126, or 134-146 (and particularly SEQ ID NO: 50); 88% sequence identity with any of SEQ ID NOs: 1-124, 126, or 134-146 (and particularly SEQ ID NO: 50); 89% sequence identity with any of SEQ ID NOs: 1-124, 126, or 134-146 (and particularly SEQ ID NO: 50); 90% sequence identity with any of SEQ ID NOs: 1-124, 126, or 134-146 (and particularly SEQ ID NO: 50); 91% A sequence identity with any of SEQ ID NOs: 1-124, 126, or 134-146 (and particularly SEQ ID NO: 50); 92% sequence identity with any of SEQ ID NOs: 1-124, 126, or 134-146 (and particularly SEQ ID NO: 50); 93% sequence identity with any of SEQ ID NOs: 1-124, 126, or 134-146 (and particularly SEQ ID NO: 50); 94% sequence identity with any of SEQ ID NOs: 1-124, 126, or 134-146 (and particularly SEQ ID NO: 50); 95% sequence identity with any of SEQ ID NOs: 1-124, 126, or 134-146 (and particularly SEQ ID NO: 50); 96% sequence identity with any of SEQ ID NOs: 1-124, 126, or 134-146 (and particularly SEQ ID NO: 50); 97% sequence identity with any of SEQ ID NOs: 1-124, 126, or 134-146 (and particularly SEQ ID NO: 50); 98% sequence identity with any of SEQ ID NOs: 1-124, 126, or 134-146 (and particularly SEQ ID NO: 50); or 99% sequence identity with any of SEQ ID NOs: 1-124, 126, or 134-146 (and particularly SEQ ID NO: 50).

"Percent_(%) amino acid sequence identity" with respect to the sequences identified herein is defined as the percentage of amino acid residues in a candidate sequence that are identical with the amino acid residues in the reference sequence for each of the gp120 domain, the C4b multimerization domain, and/or the complete fusion after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, including any algorithms needed to achieve maximal alignment over the full-length of the sequences being compared. For example,_% amino acid sequence identity values generated using the WU-BLAST-2 computer program (Altschul et al., Methods in Enzymology, 266:460-480 (1996)) uses several search parameters, most of which are set to the default values. Those that are not set to default values (i.e., the adjustable parameters) are set with the following values: overlap span=1, overlap fraction=0.125, word threshold (T)=11 and scoring matrix BLOSUM62.

Variants will typically exhibit the same qualitative biological activity and elicit a substantially similar immune response as a reference peptide, although variants can be selected to modify the characteristics of a reference peptide as needed. Screening of variants can be performed using assays of gp210 peptide activities, as known in the art. In particular embodiments, there is no statistically-significant difference in an immunization effect between a variant peptide and a reference peptide.

Covalent modifications of e/m Env are included within the scope of the disclosure. One type of covalent modification includes reacting targeted amino acid residues of e/m Env with an organic derivatizing agent that is capable of reacting with selected side chains or the N- or C-terminal residues of e/m Env. Derivatization with bifunctional agents can be useful, for instance, for crosslinking e/m Env to a water-insoluble support matrix or surface for use in the methods described below, or for in vivo stability. Commonly used crosslinking agents include 1,1-bis(diazoacetyl)-2-phenylethane, glutaraldehyde, N-hydroxysuccinimide esters (e.g., esters with 4-azidosalicylic acid), homobifunctional imidoesters, including disuccinimidyl esters (e.g., 3,3'-dithiobis(succinimidylpropionate), bifunctional maleimides (e.g., bis-N-maleimido-1,8-octane) and agents such as methyl-3-((p-azidophenyl)dithio)propioimidate, and 1-ethyl-3-(-3-dimethylaminopropyl)carbodiimide hydrochloride.

Other modifications include deamidation of glutaminyl and asparaginyl residues to the corresponding glutamyl and aspartyl residues, respectively, hydroxylation of P and L, phosphorylation of hydroxyl groups of S or T residues, methylation of the amino groups of L, R, and H side chains (see, e.g., T. E. Creighton, Proteins: Structure and Molecular Properties, W.H. Freeman & Co., San Francisco, pp. 79-86 (1983)), acetylation of the N-terminal amine, and/or amidation of any C-terminal carboxyl group. In addition, modifications such as derivitization with polyethylene glycols (and other glycols) to increase the in vivo stability half-life are also included.

Compositions. Generally, e/m Env can be formulated into pharmaceutically useful compositions, whereby therapeutically effective amounts of e/m Env are combined in admixture with a pharmaceutically acceptable carrier. Salts and/or pro-drugs of e/m Env can also be used.

A pharmaceutically acceptable salt includes any salt that retains the activity of the e/m Env and is acceptable for pharmaceutical use. A pharmaceutically acceptable salt also refers to any salt which may form in vivo as a result of administration of an acid, another salt, or a prodrug which is converted into an acid or salt.

Suitable pharmaceutically acceptable acid addition salts can be prepared from an inorganic acid or an organic acid. Examples of such inorganic acids are hydrochloric, hydrobromic, hydroiodic, nitric, carbonic, sulfuric and phosphoric acid. Appropriate organic acids can be selected from aliphatic, cycloaliphatic, aromatic, arylaliphatic, heterocyclic, carboxylic and sulfonic classes of organic acids.

Suitable pharmaceutically acceptable base addition salts include metallic salts made from aluminum, calcium, lithium, magnesium, potassium, sodium and zinc or organic salts made from N,N'-dibenzylethylene-diamine, chloroprocaine, choline, diethanolamine, ethylenediamine, N-methylglucamine, lysine, arginine and procaine.

A prodrug includes an active ingredient which is converted to a therapeutically active compound after administration, such as by cleavage of a e/m Env or by hydrolysis of a biologically labile group.

In some embodiments, the compositions include e/m Env of at least 0.1% w/v of the composition; at least 1% w/v of composition; at least 10% w/v of composition; at least 20% w/v of composition; at least 30% w/v of composition; at least 40% w/v of composition; at least 50% w/v of composition; at least 60% w/v of composition; at least 70% w/v of composition; at least 80% w/v of composition; at least 90% w/v of composition; at least 95% w/v of composition; or at least 99% w/v of composition.

In other embodiments, e/m Env can be provided as part of a composition that can include, for example, at least 0.1% w/w of composition; at least 1% w/w of composition; at least 10% w/w of composition; at least 20% w/w of composition; at least 30% w/w of composition; at least 40% w/w of composition; at least 50% w/w of composition; at least 60% w/w of composition; at least 70% w/w of composition; at least 80% w/w of composition; at least 90% w/w of composition; at least 95% w/w of composition; or at least 99% w/w of composition.

Exemplary generally used pharmaceutically acceptable carriers include any and all absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

Exemplary antioxidants include ascorbic acid, methionine, and vitamin E.

Exemplary buffering agents include citrate buffers, succinate buffers, tartrate buffers, fumarate buffers, gluconate buffers, oxalate buffers, lactate buffers, acetate buffers, phosphate buffers, histidine buffers, and/or trimethylamine salts.

An exemplary chelating agent is EDTA.

Exemplary isotonic agents include polyhydric sugar alcohols including trihydric or higher sugar alcohols, such as glycerin, erythritol, arabitol, xylitol, sorbitol, or mannitol.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Stabilizers refer to a broad category of excipients which can range in function from a bulking agent to an additive which solubilizes the e/m Env or helps to prevent denaturation or adherence to the container wall. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on e/m Env weight.

The compositions disclosed herein can be formulated for administration by, for example, injection, inhalation, infusion, perfusion, lavage, or ingestion. The compositions disclosed herein can further be formulated for intravenous, intradermal, intraarterial, intranodal, intralymphatic, intraperitoneal, intralesional, intraprostatic, intravaginal, intrarectal, topical, intrathecal, intratumoral, intramuscular, intravesicular, oral and/or subcutaneous administration and more particularly by intravenous, intradermal, intraarterial, intranodal, intralymphatic, intraperitoneal, intralesional, intraprostatic, intravaginal, intrarectal, intrathecal, intratumoral, intramuscular, intravesicular, and/or subcutaneous injection.

For injection, compositions can be formulated as aqueous solutions, such as in buffers including Hanks' solution, Ringer's solution, or physiological saline. The aqueous solutions can contain formulatory agents such as suspending, stabilizing, and/or dispersing agents. Alternatively, the formulation can be in lyophilized and/or powder form for constitution with a suitable vehicle, e.g., sterile pyrogen-free water, before use.

For oral administration, the compositions can be formulated as tablets, pills, dragees, capsules, liquids, gels, syrups, slurries, suspensions and the like. For oral solid formulations such as powders, capsules and tablets, suitable excipients include binders (gum tragacanth, acacia, cornstarch, gelatin), fillers such as sugars, e.g. lactose, sucrose, mannitol and sorbitol; dicalcium phosphate, starch, magnesium stearate, sodium saccharine, cellulose, magnesium carbonate; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents can be added, such as corn starch, potato starch, alginic acid, cross-linked polyvinylpyrrolidone, agar, or alginic acid or a salt thereof such as sodium alginate. If desired, solid dosage forms can be sugar-coated or enteric-coated using standard techniques. Flavoring agents, such as peppermint, oil of wintergreen, cherry flavoring, orange flavoring, etc. can also be used.

Compositions can be formulated as an aerosol. In one embodiment, the aerosol is provided as part of an anhydrous, liquid or dry powder inhaler. Aerosol sprays from pressurized packs or nebulizers can also be used with a suitable propellant, e.g., dichlorodifluoromethane, trichlorofluoromethane, dichlorotetrafluoroethane, carbon dioxide or other suitable gas. In the case of a pressurized aerosol, a dosage unit may be determined by providing a valve to deliver a metered amount. Capsules and cartridges of gelatin for use in an inhaler or insufflator may also be formulated containing a powder mix of e/m Env and a suitable powder base such as lactose or starch.

Compositions can also be formulated as depot preparations. Depot preparations can be formulated with suitable polymeric or hydrophobic materials (for example as an emulsion in an acceptable oil) or ion exchange resins, or as sparingly soluble derivatives, for example, as sparingly soluble salts.

Additionally, compositions can be formulated as sustained-release systems utilizing semipermeable matrices of solid polymers containing at least one e/m Env. Various sustained-release materials have been established and are well known by those of ordinary skill in the art. Sustained-release systems may, depending on their chemical nature, release e/m Env following administration for a few weeks up to over 100 days. Depot preparations can be administered by injection; parenteral injection; instillation; or implantation into soft tissues, a body cavity, or occasionally into a blood vessel with injection through fine needles.

Depot formulations can include a variety of bioerodible polymers including poly(lactide), poly(glycolide), poly (caprolactone) and poly(lactide)-co(glycolide) (PLG) of desirable lactide:glycolide ratios, average molecular weights, polydispersities, and terminal group chemistries. Blending different polymer types in different ratios using various grades can result in characteristics that borrow from each of the contributing polymers.

The use of different solvents (for example, dichloromethane, chloroform, ethyl acetate, triacetin, N-methyl pyrrolidone, tetrahydrofuran, phenol, or combinations thereof) can alter microparticle size and structure in order to modulate release characteristics. Other useful solvents include water, ethanol, dimethyl sulfoxide (DMSO), N-methyl-2-pyrrolidone (NMP), acetone, methanol, isopropyl alcohol (IPA), ethyl benzoate, and benzyl benzoate.

Exemplary release modifiers can include surfactants, detergents, internal phase viscosity enhancers, complexing agents, surface active molecules, co-solvents, chelators, stabilizers, derivatives of cellulose, (hydroxypropyl)methyl cellulose (HPMC), HPMC acetate, cellulose acetate, pluronics (e.g., F68/F127), polysorbates, Span® (Croda Americas, Wilmington, Del.), poly(vinyl alcohol) (PVA), Brij® (Croda Americas, Wilmington, Del.), sucrose acetate isobutyrate (SAIB), salts, and buffers.

Excipients that partition into the external phase boundary of microparticles such as surfactants including polysorbates, dioctylsulfosuccinates, poloxamers, PVA, can also alter properties including particle stability and erosion rates, hydration and channel structure, interfacial transport, and kinetics in a favorable manner.

Additional processing of the disclosed sustained release depot formulations can utilize stabilizing excipients including mannitol, sucrose, trehalose, and glycine with other components such as polysorbates, PVAs, and dioctylsulfosuccinates in buffers such as Tris, citrate, or histidine. A freeze-dry cycle can also be used to produce very low moisture powders that reconstitute to similar size and performance characteristics of the original suspension.

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

Kits. Also disclosed herein are kits including one or more containers including one or more of the e/m Env and/or compositions described herein. Associated with such container(s) can be a notice in the form prescribed by a governmental agency regulating the manufacture, use, or sale of pharmaceuticals or biological products, which notice reflects approval by the agency of manufacture, use, or sale for human administration.

Optionally, the kits described herein further include instructions for using the kit in the methods disclosed herein. In various embodiments, the kit may include instructions regarding preparation of the e/m Env and/or compositions for administration; administration of the e/m Env and/or compositions; appropriate reference levels to interpret results associated with using the kit; proper disposal of the related waste; and the like. The instructions can be in the form of printed instructions provided within the kit or the instructions can be printed on a portion of the kit itself. Instructions may be in the form of a sheet, pamphlet, brochure, CD-Rom, or computer-readable device, or can provide directions to instructions at a remote location, such as a website. In various embodiments, possible side effects and contraindications to further use of components of the kit based on a subject's symptoms can be included.

Methods of Use. Once formed, the compositions find use in a number of applications. In particular embodiments, the compositions find use in the treatment of disease. "Treatment" refers to both therapeutic treatment and prophylactic treatment or preventative measures, wherein the object is to prevent, reduce the occurrence or severity of, or slow down or lessen a targeted pathologic condition or disorder. "Subjects" include those in need of treatment, such as, those with an infection, as well as those prone to have or develop an infection, or those in whom infection is to be prevented, such as those in a high risk group for exposure to a pathogen.

Thus, in various exemplary embodiments, a subject can be a human subject. Other types of subjects include veterinary animals (dogs, cats, reptiles, birds, etc. and also including animals found within zoos), livestock (horses, cattle, goats, pigs, chickens, etc.), and research animals (monkeys, rats, mice, fish, etc.).

The compositions can be administered prophylactically in subjects who are at risk of developing HIV infection, or who have been exposed to HIV, to prevent, reduce, or delay the development of HIV infection or disease. For example, the compositions can be administered to a subject likely to have been exposed to HIV or to a subject who is at high risk for exposure to HIV.

In particular embodiments, compositions can be administered to a subject in a therapeutically effective amount. A "therapeutically effective amount" is an amount sufficient to produce a desired physiological effect and/or an amount capable of achieving a desired result, particularly for treatment of a disorder or disease condition, including reducing or eliminating one or more symptom of the disorder or disease or prevention or delaying the onset of at least one a disease symptom. Therapeutically effective amounts can provide therapeutic treatments and/or prophylactic treatments.

Particular uses of the compositions include use as prophylactic vaccines. Vaccines increase the immunity of a subject against a particular disease. Therefore, "HIV vaccine" can refer to a treatment that increases the immunity of a subject against HIV. Therefore, in some embodiments, a vaccine may be administered prophylactically, for example to a subject that is immunologically naive (e.g., no prior exposure or experience with HIV). In some embodiments, a vaccine may be administered therapeutically to a subject who has been exposed to HIV. Thus, a vaccine can be used to ameliorate a symptom associated with AIDS or HIV infection, such as a reduced T cell count.

In particular embodiments, an HIV vaccine is a therapeutically effective composition comprising one or more e/m Env disclosed herein that induce an immune response in a subject against HIV. The skilled artisan will appreciate that the immune system generally is capable of producing an innate immune response and an adaptive immune response. An innate immune response generally can be characterized as not being substantially antigen specific and/or not generating immune memory. An adaptive immune response can be characterized as being substantially antigen specific, maturing over time (e.g., increasing affinity and/or avidity for antigen), and in general can produce immunologic memory. Even though these and other functional distinctions between innate and adaptive immunity can be discerned, the skilled artisan will appreciate that the innate and adaptive immune systems can be integrated and therefore can act in concert.

"Immune response" refers to a response of the immune system to an e/m Env disclosed herein. In various exemplary embodiments, an immune response to an e/m Env can be an innate and/or adaptive response. In some embodiments, an adaptive immune response can be a "primary immune response" which refers to an immune response occurring on the first exposure of a "naive" subject to an e/m Env. For example, in the case of a primary antibody response, after a lag or latent period of from approximately 3 to 14 days depending on, for example, the composition, dose, and subject, antibodies to the e/m Env can be produced. Generally, IgM production lasts for several days followed by IgG production and the IgM response can decrease. Antibody production can terminate after several weeks but memory cells can be produced. In some embodiments, an adaptive immune response can be a "secondary immune response", "anamnestic response," or "booster response" which refer to the immune response occurring on a second and subsequent exposure of a subject to an e/m Env disclosed herein. Generally, in a secondary immune response, memory cells respond to the e/m Env and therefore the secondary immune response can differ from a primary immune response qualitatively and/or quantitatively. For example, in comparison to a primary antibody response, the lag period of a secondary antibody response can be shorter, the peak antibody titer can be higher, higher affinity antibody can be produced, and/or antibody can persist for a greater period of time.

Thus, in particular embodiments, an immune response against HIV will include antibody production against the gp120 domain of an e/m Env.

"Antibodies" refer to polyclonal or monoclonal antibodies that can be induced by an e/m Env according to the methods disclosed herein. In some embodiments, an antibody can bind to a gp120 domain of an e/m Env. In some embodiments, an antibody prevents AIDS and/or ameliorates a symptom of AIDS or HIV infection in a subject. Thus, in some embodiments, an antibody can bind to gp120 (i.e., an etiologic agent of HIV). Without being bound by theory, in some embodiments, the binding of an antibody can substantially neutralize or inactivate HIV gp120. Thus, antibodies are capable of reducing or eliminating a pathologic effect of HIV. That is, the binding of antibodies to gp120 of HIV may decrease or eliminate HIV infectivity and/or virulence factor activity, including replication, synthesis, and/or toxicity. In particular embodiments, at least a 25% decrease of one of these parameters is required to determine that a dose provides a therapeutically effective amount.

The actual dose amount administered to a particular subject can be determined by a physician, veterinarian, or researcher taking into account parameters such as physical and physiological factors including target, body weight, severity of infection, stage of infection, previous or concurrent therapeutic interventions, idiopathy of the subject, and route of administration.

For administration, therapeutically effective amounts (also referred to herein as doses) can be initially estimated based on results from in vitro assays and/or animal model studies. Exemplary doses include 1, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240 or 250 µg/kg body mass or mg/kg body mass although higher and/or lower doses can be used. The number of doses that can be administered as a function of time can be from 1, 2, 3, 4 or 5 doses over 1, 2, 3, 4, 5 or 6 weeks but can be increased or decreased depending at least in part on the immune status of a subject.

In particular embodiments, a composition can be administered initially, and thereafter maintained by further administration. For example, a composition can be administered by intravenous injection to bring blood levels to a suitable level. The subject's levels are then maintained by an oral dosage form, although other forms of administration, dependent upon the patient's condition, may be used. In the instance of a vaccine composition, the vaccine may be administered as a single dose, or the vaccine may incorporate set booster doses. For example, booster doses may include variants in order to provide protection against multiple clades of HIV.

The e/m Env can be prepared by expressing polynucleotide sequences in vectors or other expression vehicles in compatible prokaryotic or eukaryotic host cells using standard molecular biology methods (e.g., Sambrook et al. 1989, Molecular Cloning a Laboratory Manual, Second Edition, Cold Spring Harbor Laboratory Press, Cold Spring Harbor, N.Y.; incorporated herein by reference).

A "polynucleotide sequence" is at least two nucleotides covalently linked together. A polynucleotide sequence will generally contain phosphodiester bonds, although in some cases, polynucleotide sequence analogs are included that may have alternate backbones, including, for example, phosphoramide, phosphorothioate, phosphorodithioate, O-methylphophoroamidite linkages, and peptide nucleic acid backbones and linkages. Other analog nucleic acids include those with positive backbones; non-ionic backbones; and non-ribose backbones. Polynucleotide sequences containing one or more carbocyclic sugars are also included within the definition of nucleic acids. These modifications of the ribose-phosphate backbone may be included to facilitate the addition of additional moieties such as labels, or to increase the stability and half-life of such molecules in physiological environments. Determining the type of nucleotides and their position within a polynucleotide sequence depends at least in part on the intended use of the polynucleotide sequence and is within the abilities of the skilled artisan.

The polynucleotide sequences may be single stranded or double stranded, as specified, or contain portions of both double stranded or single stranded sequences. The polynucleotide sequence may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

In particular embodiments, a polynucleotide sequence can express a domain or an e/m Env disclosed herein. As such, polynucleotide sequences can include polynucleotide sequences encoding a polypeptide(s) of interest, operably linked to additional regulatory or accessory elements required or helpful for its expression and use. Generally, "operably linked" means that the nucleic acid sequences being linked are contiguous and arranged so that they function in concert for their intended purposes—for example, transcription initiates in the promoter and proceeds through the coding polynucleotide segment to the terminator. Where necessary to join two protein coding regions, the polynucleotide coding sequences should be contiguous and in reading frame.

Regulatory or accessory elements can include promoter and terminator sequences, enhancer sequences, polyadenylation signals, translational regulatory elements, including ribosomal binding sites. The transcriptional and translational regulatory or accessory elements employed are functional in the host cell used for expression, and may include those naturally associated with HIV genes. Therefore, in some embodiments a polynucleotide sequence can include sequences such as a promoter (e.g., inducible or constitutive), enhancer sequences (e.g., IE1 enhancer), introns sequences, transcriptional regulatory elements, and polyadenylation sequences (e.g., BGH polyadenylation sequence).

Promoters such as the trp, lac and phage promoters, tRNA promoters and glycolytic enzyme promoters may be used in prokaryotic hosts. Useful yeast promoters include the promoter regions for metallothionein, 3-phosphoglycerate kinase or other glycolytic enzymes such as enolase or glyceraldehyde-3-phosphate dehydrogenase, enzymes responsible for maltose and galactose utilization, and others. Appropriate non-native mammalian promoters may include the early and late promoters from SV40 or promoters derived from murine moloney leukaemia virus, mouse mammary tumour virus, avian sarcoma viruses, adenovirus II, bovine papilloma virus or polyoma. In particular embodiments, the expression vector comprises a CMV promoter.

Polynucleotide sequences encoding protein sequences disclosed herein can be derived by commercially and publicly-available databases.

In another aspect, the disclosure provides a vector comprising a polynucleotide sequence that encodes an e/m Env comprising a gp120 domain and a C4b multimerization domain.

In particular embodiments, the vector is selected from a DNA vector, a RNA vector, a viral vector, a bacterial vector, a plasmid vector, a cosmid vector, an artificial chromosome vector, such as a yeast artificial chromosome vector.

Viral vectors are usually non-replicating or replication-impaired vectors, which means that the viral vector cannot replicate to any significant extent in normal cells (e.g., normal human cells), as measured by conventional means (e.g. via measuring DNA synthesis and/or viral titer). Non-replicating or replication-impaired vectors may have become so naturally (i.e., they have been isolated as such from nature) or artificially (e.g., by breeding in vitro or by genetic manipulation). There will generally be at least one cell-type in which the replication-impaired viral vector can be grown—for example, modified vaccinia Ankara (MVA) can be grown in CEF cells. Typically, viral vectors are incapable of causing a significant infection in a subject, typically in a mammalian subject.

In particular embodiments, the vector is selected from an adenovirus or a poxvirus vector. Examples of viral vectors that are useful in this context include attenuated vaccinia virus vectors such as modified vaccinia Ankara (MVA) and NYVAC, or strains derived therefrom. Other examples of vectors include an avipox vector, such as a fowlpox vectors (e.g., FP9) or canarypox vectors (e.g., ALVAC and strains derived therefrom). Alternative viral vectors include adenoviral vectors (e.g., non-human adenovirus vectors), alphavirus vectors, flavivirus vectors, herpes viral vectors (e.g., herpes simplex, CMV and EBV), influenza virus vectors and retroviral vectors.

In particular embodiments, the vector is a human adenovirus. In another embodiment, the vector is a simian adenovirus. In another embodiment, the vector is a chimpanzee adenovirus. A chimpanzee as referred to herein may include *Pan troglodytes* (common chimpanzee) and *Pan paniscus* (Bonobo). In particular embodiments, the vector is selected from adenovirus 5 (Ad5), adenovirus 35 (Ad35), adenovirus 11 (Ad11), adenovirus 26 (Ad26), adenovirus 48 (Ad48) or adenovirus 50 (Ad50).

"Host cells", and other such terms denoting microorganisms or higher eukaryotic cell lines cultured as unicellular entities refer to cells which can be, or have been, used as recipients for recombinant vector or other transfer DNA, and include the progeny of the original cell which has been transformed. It is understood that the progeny of a single parental cell may not necessarily be completely identical in morphology or in genomic or total DNA complement as the original parent, due to natural, accidental or deliberate mutation.

The most commonly used prokaryotic hosts are strains of *E. coli*, although other prokaryotes, such as *B. subtilis* or *Pseudomonas* may be used. Mammalian or other eukaryotic host cells, such as those of yeast, filamentous fungi, plant, insect, amphibian or avian species, may also be useful. Propagation of mammalian cells in culture is per se well known. Examples of commonly used mammalian host cell lines are VERO and HeLa cells, Chinese hamster ovary (CHO) cells, and WI38, BHK, and COS cell lines, although other cell lines may be appropriate, e.g., to provide higher expression.

Expression and cloning vectors may contain a selectable marker, a gene encoding a protein necessary for the survival or growth of a host cell transformed with the vector. This gene ensures the growth of only those host cells which express the inserts. Conventional selection genes encode proteins that (i) confer resistance to antibiotics or other toxic substances, e.g., ampicillin, neomycin, methotrexate, etc.; (ii) complement auxotrophic deficiencies; or (iii) supply critical nutrients not available from complex media, e.g. the gene encoding D-alanine racemase for Bacilli. The choice of appropriate selectable marker will depend on the host cell.

The transformed host cell can be cultured in accordance with known methods, and the expressed polypeptide may be harvested i.e. recovered and isolated (eg. from the culture medium) using conventional protocols.

EXEMPLARY EMBODIMENTS

1. An engineered and multimerized (e/m) human immunodeficiency virus (HIV) envelope glycoprotein (Env) including SEQ ID NO: 50.
2. An e/m Env including an artificial human immunodeficiency virus (HIV) envelope glycoprotein selected from SEQ ID NOs: 52-121 and a heptamerization domain selected from SEQ ID NOs: 14-49 or 51.
3. An e/m Env including an artificial HIV envelope glycoprotein selected from SEQ ID NO: 52 and a heptamerization domain selected from SEQ ID NO: 14 or SEQ ID NOs: 46-49 or 51.
4. An e/m Env including an HIV envelope glycoprotein and a heptamerization domain.
5. An e/m Env of embodiment 4, wherein the heptamerization domain is selected from SEQ ID NOs: 14-49 or 51.
6. An e/m Env of embodiment 4 or 5, wherein the HIV envelope glycoprotein is an artificial gp120.
7. An e/m Env of any of embodiments 4-6, wherein the artificial gp120 is selected from SEQ ID NOs: 52-121.
8. An e/m Env of any one of embodiments 1-7, multimerized into a heptamer or a larger order multimer based on a heptamer.
9. A composition including a fusion protein of embodiment 8 or an e/m Env of any of embodiments 1-8.
10. A kit including an e/m Env of any one of embodiments 1-9.
11. A vector encoding an e/m Env of any one of embodiments 1-9.
12. A host cell including a vector of embodiment 11.
13. An e/m Env including: (i) mutations: N460D; N463D; S278R; G471S; V65C; and S115C; (ii) removal of the V1 loop and the V2 loop; (iii) replacement of the V3 loop with a flexible linker; (iv) an N-terminal truncation; and (v) a heptamerization domain; wherein the e/m Env does not include a mutation at position 276.
14. An e/m Env of embodiment 13 wherein the N-terminal truncation is before residue 49, 48, 47, 46, 45, 44, 43, 42, 41, 40 or 39.
15. An e/m Env of embodiment 13 wherein the N-terminal truncation is before residue 44.
16. An e/m Env of any one of embodiments 13-15 further including a C-terminal truncation after residue 499, 498, 497, 496, 495, 494, 493, 492, 491, 490 or 389.
17. An e/m Env of any one of embodiments 13-15 wherein the C-terminal truncation is after residue 494.
18. An e/m Env of any one of embodiments 13-17 wherein the flexible linker is selected from SEQ ID NOs: 3-13, or 126.
19. An e/m Env of any one of embodiments 13-18 wherein the V3 loop includes 296-331.
20. An e/m Env of any one of embodiments 13-19 wherein the heptamerization domain is selected from SEQ ID NOs: 14-49 or 51.
21. An e/m Env of any one of embodiments 13-20 wherein removal of the V1 loop includes removal of 131-152 and/or removal of the V2 loop includes removal of 161-196.
22. An e/m Env of any one of embodiments 13-20 wherein removal of the V1 loop and removal of the V2 loop includes removal of 123-196.
23. An e/m Env of any one of embodiments 13-22, multimerized into a heptamer or a larger order multimer based on a heptamer.
24. A composition including a fusion protein of embodiment 23 or an e/m Env of any of embodiments 13-23.
25. A kit including an e/m Env of any of embodiments 13-23.
26. A vector including an e/m Env of any of embodiments 13-23.
27. A host cell including a vector of embodiment 26.

Example 1

DG75 B cells that were transduced to stably express the gl-reverted (gl)VRC01, 12A21, and NIH45-46 B cell receptors (as indicated), were loaded with the Calcium binding indicator dye Fluo-4. B cells were then challenged with the indicated 426c.TM4ΔV1-3 gp140 trimer (FIG. 3, black lines) or the 426c.TM4ΔV1-3 fused to the C4b heptamerization domain (FIG. 3, boxed lines) at the indicated concentrations, and the fluorescent signal from the Fluo-4 dye was measured over time. The 426c.TM4ΔV1-3 fused to the C4b heptamerization domain induces a stronger Calcium flux response than the trimeric form of the Envelope.

Figure 4:
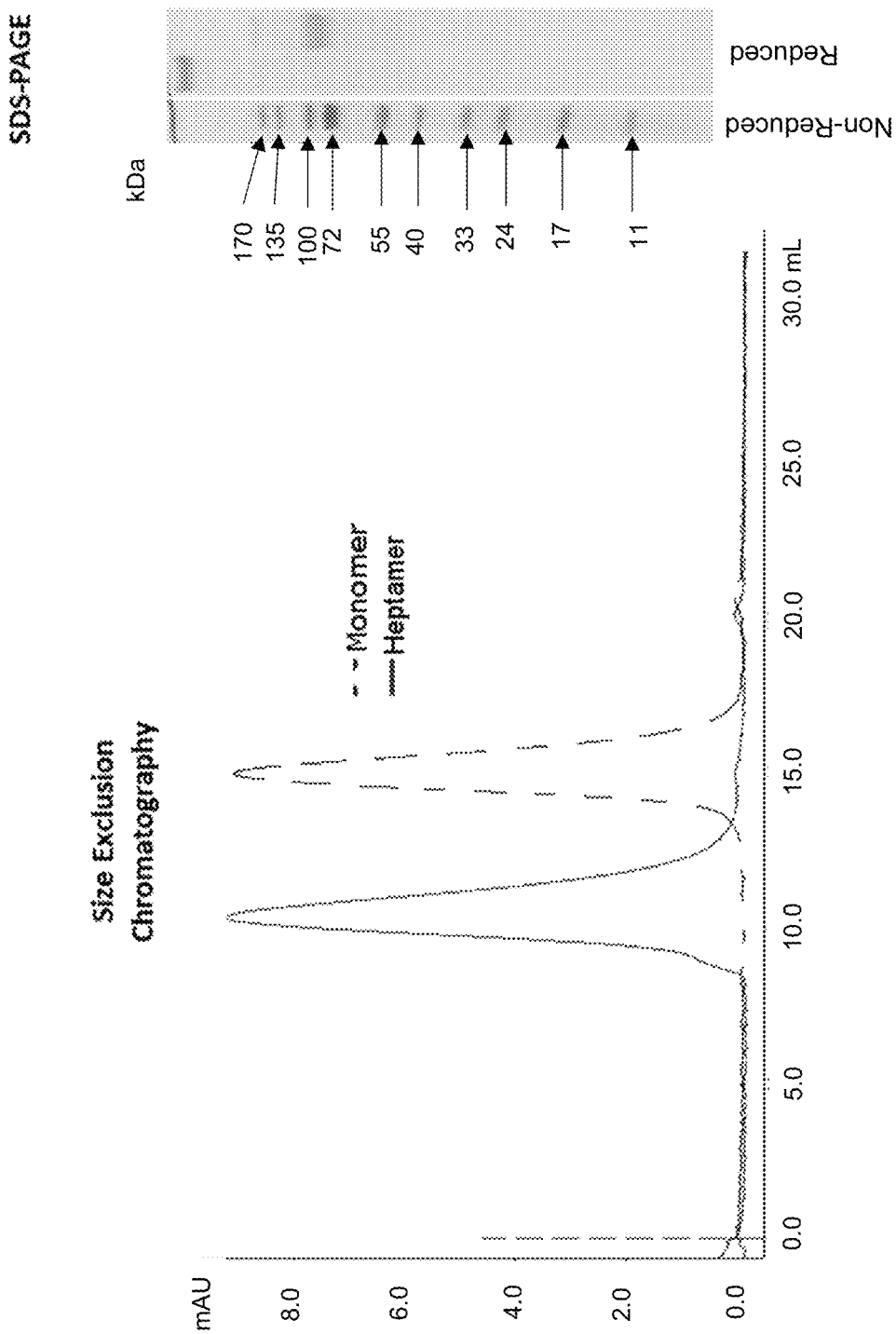
FIG. 4 shows biochemical characterization. 75 ug of the 426c.TM4ΔV1-3 core gp120 monomer (dashed chromatogram) or 75 ug of the 426c.TM4ΔV1-3 fused to the C4b heptamerization domain (solid chromatogram) were ran on an S200 10/300 size exclusion column (left panel). The 426c.TM4ΔV1-3 fused to the C4b heptamerization domain elutes sooner than the 426c.TM4ΔV1-3 gp120 monomer consistent with it being in a larger multimeric state. The 426c.TM4ΔV1-3 fused to the C4b heptamerization domain was subjected to SDS PAGE under reducing, and non-reducing conditions as indicated. The unreduced sample runs as a discrete high molecular weight band, consistent with disulphide linked C4b subunits. Under reducing conditions the e/m Env runs as a single band of the expected 85 kDa size.

75 ug of the 426c.TM4ΔV1-3 gp120 monomer (FIG. 4, dashed chromatogram) or 75 ug of the 426c.TM4ΔV1-3 fused to the C4b heptamerization domain (FIG. 4, solid chromatogram) were ran on an S200 10/300 size exclusion column (FIG. 4, left panel). The 426c.TM4ΔV1-3 fused to the C4b heptamerization domain elutes sooner than the 426c.TM4ΔV1-3 monomer consistent with it being in a larger multimeric state. The 426c.TM4ΔV1-3 fused to the C4b heptamerization domain was subjected to SDS PAGE under reducing, and non-reducing conditions as indicated. The unreduced sample runs as a discrete high molecular weight band, consistent with disulphide linked C4b subunits. Under reducing conditions the e/m Env runs as a single band of the expected 85 kDa size.

Example 2

METHODS. Cell lines. Recombinant HIV-1 Envelope and antibodies were expressed in Freestyle 293F cells (Life technologies) that were not tested for *mycoplasma* contamination.

Antibody production. Expression plasmids for the gl forms of VRC01, NIH45-46, 3BNC60 and 12A21 were previously described. Hoot, et al., Recombinant HIV envelope proteins fail to engage gl versions of anti-CD4bs bNAbs. PLoS pathogens 9, e1003106 (2013); Scheid, et al., Science 333, 1633-1637 (2011). This method was used to design plasmids expressing the gl forms of VRC-PG19, VRC-PG20, VRC-PG04 and VRC-CH31 based on the published sequences. Jardine, et al., Science 340, 711-716 (2013).

Plasmids expressing the Fab forms of these antibodies were produced by inserting a 6-His tag followed by a stop codon directly after the C1 region of the heavy chain expression plasmids (forward Fab mutagenesis primer, 5'-caaatcttgtgacaaaactcaccatcaccatcaccattgacagcacct-gaactcctgggggac-3' (SEQ ID NO: 125)).

slgGs were produced by co-transfecting the appropriate heavy and light chain plasmids at a 1:1 ratio into Freestyle 293F cells at a density of $10^6$ cells/ml in Freestyle 293 media (Life Technologies) using the 293Free transfection reagent (EMD Millipore). Antibody expression was carried out in Freestyle 293 media for 6 days with gentle shaking at 37° C. in the presence of 5% $CO_2$ after which cells and cellular debris were removed by centrifugation at 10,000×g followed by filtration through a 0.2 µM filter. Supernatants were then applied to Pierce Protein A Agarose (Thermo Scientific) followed by washing with PBS. Antibodies were eluted in 1 ml fractions with Pierce IgG Elution Buffer pH 2.0 (Thermo Scientific) into 1.5 ml centrifuge tubes containing 0.1 ml of 1M Tris-HCl pH 8.0. Fractions containing protein were pooled and exchanged into PBS using Zebra spin desalting columns (Thermo Scientific).

Fab fragments were produced in a similar manner. Following filtration the clarified supernatant was then passed over Ni-NTA resin (Qiagen, Valencia, Calif.), pre-equilbrated with Ni-NTA binding buffer, followed by extensive washing with Ni-NTA binding buffer supplemented with 10 mM imidazole, and then eluted with 250 mM imidazole, 0.3 M NaCl, 20 mM Tris, pH 8.0. Ni-NTA FAb fragments were further purified by size exclusion chromatography (SEC) using a 10/300 S200 column (GE healthcare) equilibrated in PBS.

Figure 6A:
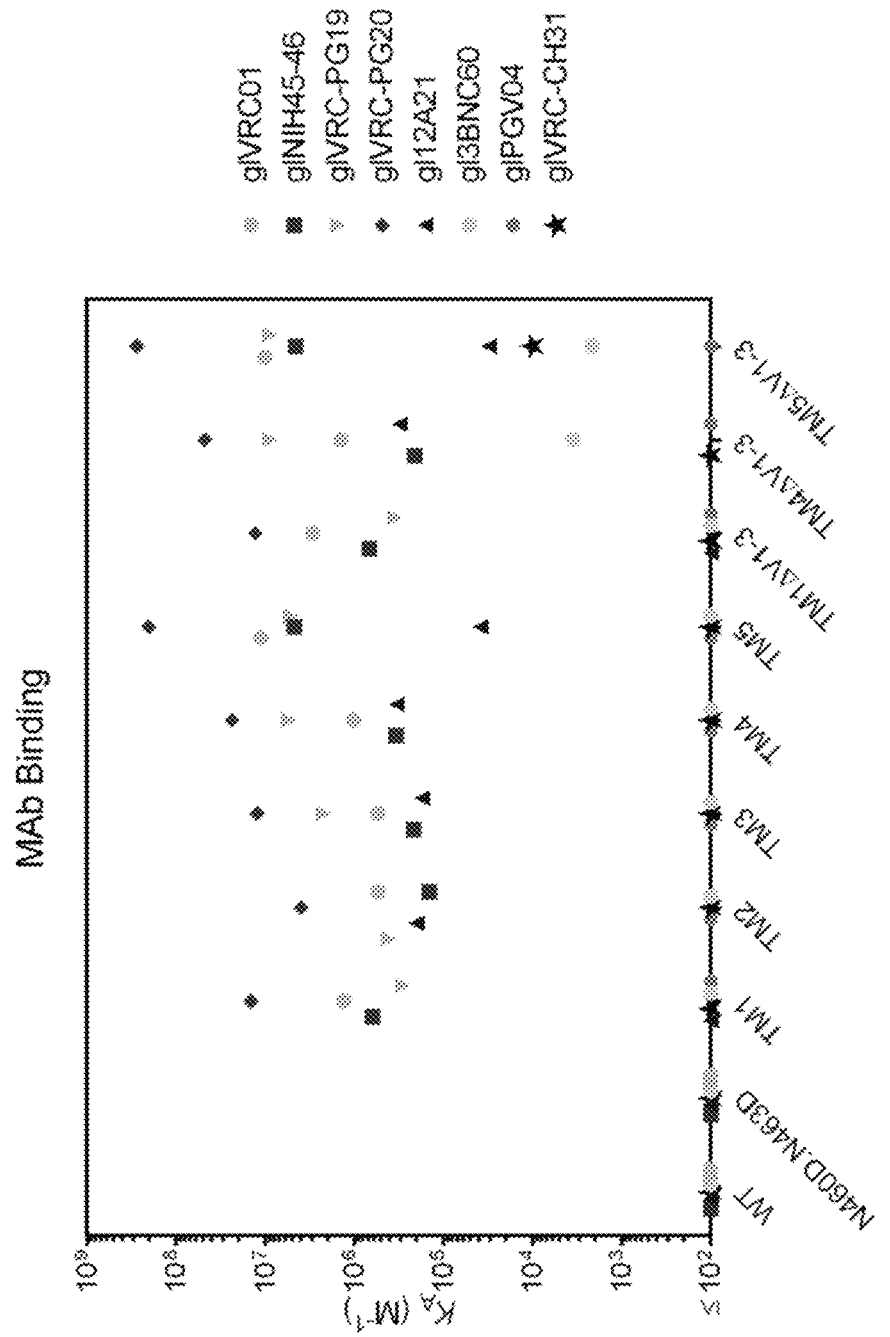
Figure 8:
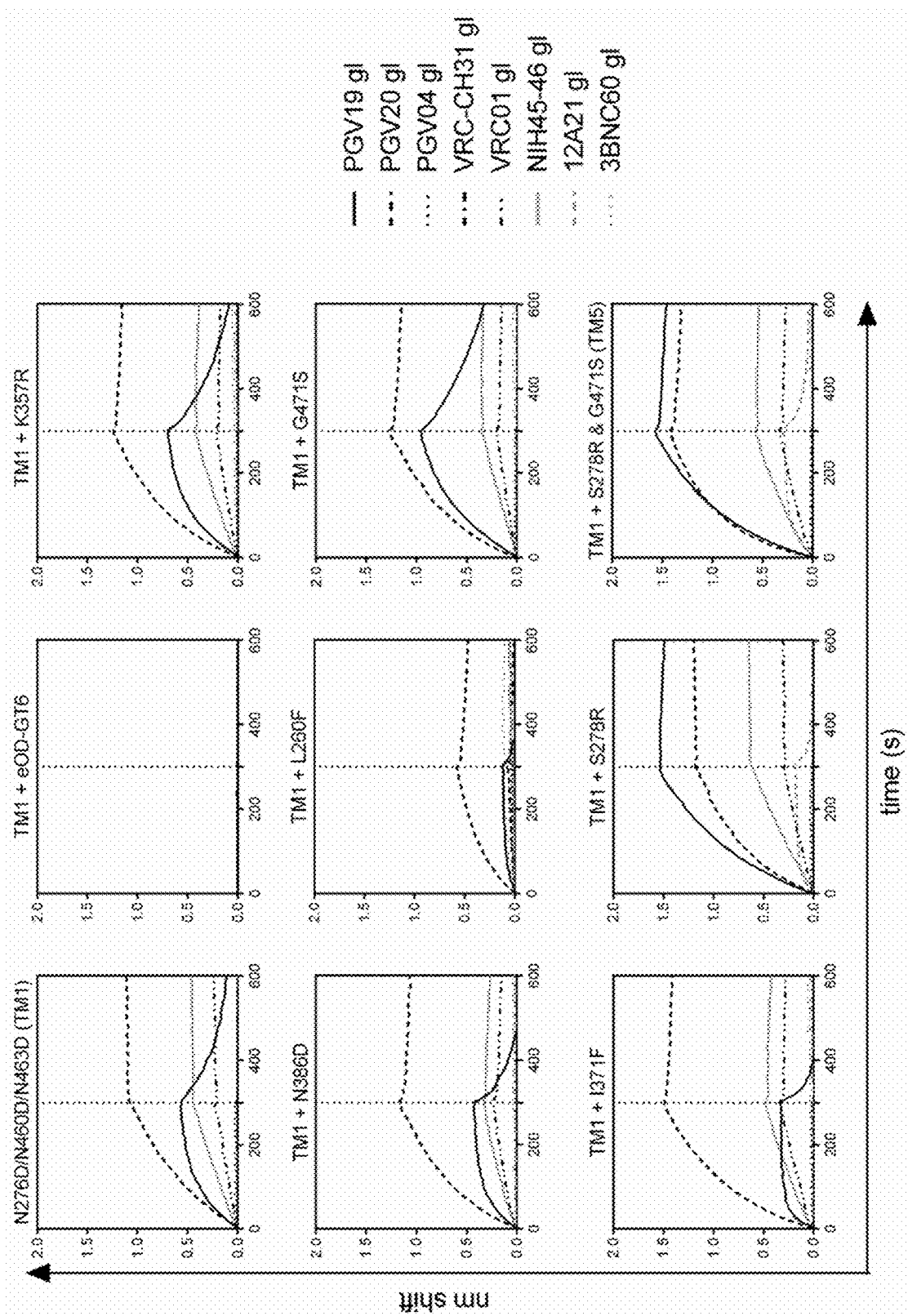
FIG. 8. Binding of glVRC01-class antibodies to 426c Env with mutations previously identified as improving antibody-recognition of the outer domain of gp120, eOD-GT6. The interaction of the indicated gl antibodies to gp120 variants of 426cTM1 with six additional mutations identified to improve glVRC01-class antibodies to eOD-GT611 were determined by BLI.
Figure 9:
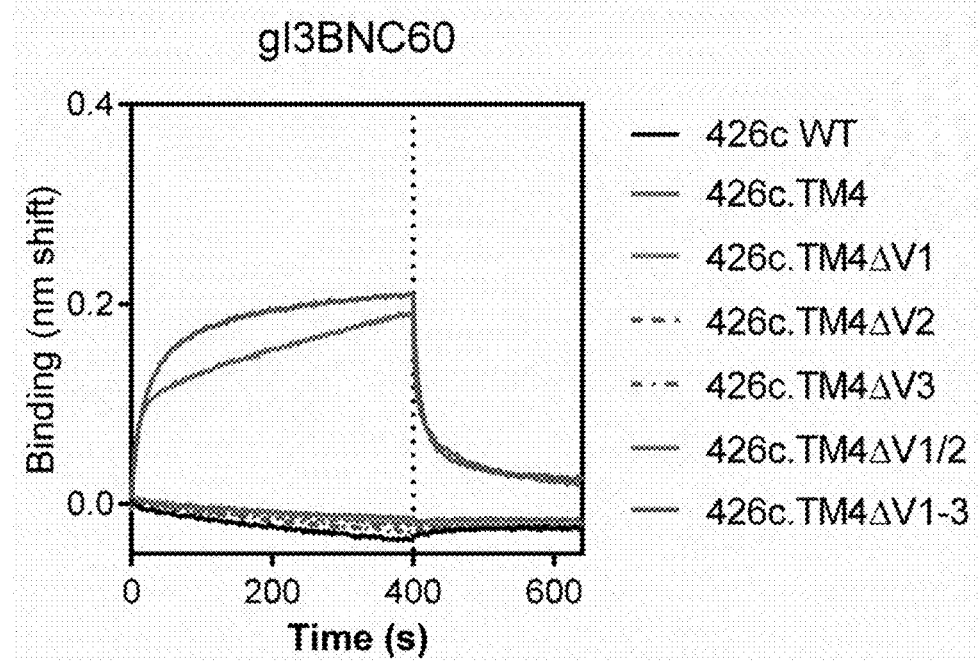
FIG. 9. Effect of Env variable loop deletions on the binding of gl3BNC60. Binding of gl3BNC60 to 426cTM4 gp120, or to 426cTM4 gp120 with the variable regions 1, 2 and 3 deleted individually (426cTM4ΔV1, 426cTM4ΔV2 and 426cTM4ΔV3, respectively), or in combination (426cTM4ΔV1/2 and 426cTM4ΔV1-3). BLI traces are representative of 2 independent replicates.

Recombinant Envelopes. All constructs are based on the clade C 426c gp140 (GenBank: KC79518.1) (McGuire, et al., J. Exp. Med. 210, 655-663 (2013)) or the 426c.NLGS.TMΔV1-3 (herein called 426c.TMΔV1-3) expressed from the pTT3 vector with or without a C-terminal Avi-Tag (McGuire, et al., Science 346, 1380-1383 (2014)) unless otherwise noted. Amino acid substitutions (summarized in FIG. 6B) were generated by site-directed mutagenesis using the Stratagene Quick Change II system (Agilent Technologies, Santa Clara, Calif.) with primers designed using Agilent's QuikChange Primer Design Program and synthesized by Integrated DNA Technologies (IDT, Coralville, Iowa). All mutations were confirmed by Sanger sequencing.

gp160 plasmids encoding 426c. N276D. N460D. N463D, 426c. S276A.T462A.T465A, 426c.S278R.N460D.N463D, Q168a2.N462D.N465D, Q461e2.N276D.N463D, Bal. N276D. N463D, 823c. N276D. N463D, and 706c.N276D.N463D were generated by introducing mutations into the parental gp160 plasmids (Genbank numbers, KC79518.1, AF407148.1, AF407156.1, DQ318210.1, KC769511.1, and KC769513.1, respectively) using Agilent's QuikChange Primer Design Program and synthesized by Integrated DNA Technologies (IDT, Coralville, Iowa). All mutations were confirmed by Sanger sequencing.

cDNA for 426cTM4ΔV1-3 amino acids 44-494 (HXB2 numbering) followed by a GSGGGGSG (SEQ ID NO: 126) and the previously described Helicobacter pylori bullfrog ferritin (Kanekiyo, et al., Cell 162, 1090-1100 (2015) was codon optimized for human, synthesized by IDT technologies, and cloned into the pTT3 expression vector to create pTT3-426cTM4ΔV1-3-Ferritin.

cDNA for 426cTM4ΔV1-3 amino acids 44-494 was PCR amplified from pTT3-426cTM4ΔV1-3-Ferritin and subcloned into the pCVL-UCOE0.7-SFFV-C4b-IRES-GFP parental vector encoding the C4b heptamerization motif of SEQ ID NO: 46 (Genbank: 416733). The resulting e/m Env contains SEQ ID NO: 5 as a linker, derived from the NotI cloning site combined with sequence from the previously crystallized construct (Hofmeyer, et al., J. of Mol. Biol. 425, 1302-1317 (2013), as well as a C-terminal thrombin-6X His tag.

His-tagged 426c gp120 was engineered by disrupting the 426c furin cleavage site (RNKR→RNKG) followed immediately by the addition of a 7×-polyhisitidine tag and stop codon (forward gp120-His mutagenesis primer, 5'-ggaacaagggcgctcatcatcaccaccatcaccattgataggtggggatcg-gagc-3' (SEQ ID NO: 127)).

Recombinant Env-expression and purification. Plasmids encoding His-tagged Env proteins were transfected into 293F cells at a density of $10^6$ cells/ml in Freestyle 293 media (Life Technologies) using the 293Free transfection reagent (EMD Millipore) according to the manufacturer's instructions. Expression was carried out in Freestyle 293 media for 6 days with gentle shaking at 37° C. in the presence of 5% $CO_2$ after which cells and cellular debris were removed by centrifugation at 10,000×g followed by filtration through a 0.2 µM filter. Clarified cell supernatant was passed over Ni-NTA resin (Qiagen), pre-equilbrated with Ni-NTA binding buffer (containing 5 mM imidizole), followed by extensive washing with Ni-NTA binding buffer (supplemented with 10 mM imidazole), and then eluted with 250 mM imidazole, 0.3 M NaCl, 20 mM Tris, pH 8.0. Purified gp120 proteins were then buffer exchanged into PBS using Zebra desalting columns (Thermo Scientific). Soluble trimeric gp140 Envs were expressed in 293F cells and purified as previously described. McGuire, et al., J. Exp. Med. 210, 655-663 (2013).

AVI-tagged Env variants were biotinylated in vitro using the In Vitro Biotin Ligase Kit (Avidity) according to the manufacturer's instructions, followed by SEC using a 10/300 S 200 column (GE healthcare) equilibrated in PBS to remove un-ligated biotin and BirA enzyme.

Multimerized Env. Dextramers were formed as follows. Purified biotinylated-avi tagged 426cTM4ΔV1-3 gp120 or gp140 was mixed with a biotinylated dextran (Life Technologies, Cat #D-7142) at a 3:1 ratio (Env:biotin), with the assumption that the modified dextran had 77 biotins molecules/multimer (lot dependent value). Streptavidin (New England Biolabs Cat #N70215) was then added to achieve a 3:1:1 Env to streptavidin to biotin ratio.

pTT3-426cTM4ΔV1-3-ferritin was transfected into 293E cells at a density of $10^6$ cells/ml in Freestyle 293 media (Life Technologies) using the 293Free transfection reagent (EMD Millipore) and half the amount of DNA recommended by the manufacturer. Expression was carried out in 293Freestyle media for 6 days with gentle shaking at 37° C. in the presence of 5% $CO_2$ after which cells and cellular debris were removed by centrifugation at 10,000×g followed by filtration through a 0.2 µM filter. Clarified supernatant was passed over a GNL agarose column (Vector laboratories) pre-equilibrated in GNL binding buffer (20 mM Tris, 100 mM NaCl, 1 mM EDTA, pH 7.4) followed by extensive washing and then eluted with GNL binding buffer containing 1M methylmannopyranoside. Ferritin nano-particles were further purified by SEC using a 16/60 S200 column (GE healthcare) equilibrated in PBS, followed by a second final SEC purification step on a 10/300 superose 6 column equilibrated in PBS (GE healthcare).

426cTM4ΔV1-3-C4b was expressed in 293 Freestyle cells (Invitrogen) using the Daedalus system. Briefly, recombinant lentivirus was produced by transient co-transfection of 293T using 25-kDa PEI with pCVL-UCOE0.7-SFFV-426cTM4ΔV1-3-C4b-IRES-GFP, and psPAX2 (Addgene #12260) and pMD2.G (Addgene #12259) packaging vectors. Transduction was carried out in 150 mL flasks containing 1×10$^7$ cells in 10 mL of expression media, then cultures were expanded to a 4 L terminal culture volume. Conditioned medium was harvested by centrifugation and recombinant protein was purified using Ni-NTA.

Biolayer Interferometry (BLI). BLI assays were performed on the Octet QKe or the Octet Red instrument (ForteBio, Inc, Menlo Park, Calif.) at 30° C. with shaking at 1,000 RPM. All measurements of Env-Ab binding were corrected by subtracting the signal obtained from simultaneous traces performed with the corresponding envelopes in the absence of antibody, using PBS only. Experiments to detect glAb-binding to Env were performed as follows: Initial screening for Ab-binding was determined by immobilizing His-tagged gp120 onto Ni-NTA biosensors (Fortebio) for 300 seconds, sensors were then incubated with BSA (1 mg/ml in PBS) for 1 minute, and the baseline signal (nm shift) was recorded for 1 minute in kinetics buffer (KB: 1×PBS, 0.01% BSA, 0.02% Tween 20, and 0.005% NaN$_3$). Sensors were then immersed into solutions of antibody (20 ug/ml in PBS) for 300 seconds, followed by immersion in KB for 300 seconds.

Kinetic analysis with FAbs was performed as follows: gp140s were biotinylated using EZ-Link NHS-PEG4-Biotin (Thermo Scientific) at a ratio of one biotin molecule/gp140 trimer (0.33 biotin molecules/monomer). Unligated biotin was removed using Zebra desalting columns (Thermo Scientific) according to the manufacturer's instructions. Biotinylated trimeric recombinant gp140s were immobilized on streptavidin biosensors (Forte Bio) at concentrations that yielded the same R$_{max}$ for all Envs tested (1-2 µM). The baseline signal was recorded for 1 min in KB, then the sensors were immersed into wells containing dilutions of purified recombinant FAbs (1-32 µM) for 4 min (association phase). Sensors were then immersed in kinetic buffer (KB) without Env for an additional 8 min (dissociation phase). Curve fitting was performed using a 1:1 binding model and the Data analysis software (Fortebio). Mean k$_{on}$ and k$_{off}$ and apparent K$_D$ values were determined by averaging all binding curves that matched the theoretical fit with an R$^2$ value of ≥0.95.

Generation and characterization of gl3BNC60 knock-in mice. HC-Knock-in mice were generated as previously described. Dosenovic, et al., Cell 161, 1505-1515 (2015); Pelanda, et al., Immunity 7, 765-775 (1997); Shih, et al., Nat. Immunol. 3, 399-406 (2002). LC knock-in mice were generated in a similar way using the VJ$_L$ sequence of the predicted gl version of human 3BNC60. Hoot, et al., Recombinant HIV envelope proteins fail to engage gl versions of anti-CD4bs bNAbs. PLoS pathogens 9, e1003106 (2013). A targeting vector with homologous regions flanking the J segments of the endogenous mouse kappa locus was generated. Homologous recombination results in deletion of endogenous J segments; which minimizes rearrangement of the WT locus. The HC and LC knock-in mice were generated independently and bred to homozygosity. They were then crossed with each other to generate double heterozygous and eventually double homozygous mice. Knock-in HC and LC genotype were verified by PCR using specific primers for the 3BNC60 gl HC or LC sequences as well as primers specific for the WT untargeted loci of IgH and IgK. Naive B cell development of the newly generated KI mice were characterized by flow cytometry. A single cell suspension of BM was stained to identify immature (IgM$^{-/low}$, IgD$^-$), and mature (IgM$^{+/int}$, IgD$^+$) B cell populations. Single cell suspensions of splenocytes were stained to identify marginal zone B cells (CD23-CD21+) and follicular B cells (CD23$^+$, CD21$^{lo/-}$) and to determine kappa and lambda usage of total B cells. The following antibodies were used; anti-mouse CD4 PE-CF594, anti-mouse CD8 PE-CF594, anti-mouse Ly-6G and Ly-6C PE-CF594 and anti-mouse Ig kappa BV421 (BD biosciences), anti-Hu/Mo B220 APC-eFlour 780, anti-mouse CD19 Pe-Cy7, anti-mouse IgM PerCP-eFluor 710, anti-mouse CD21/CD35 eFluor 450 (eBiosciences). Anti-mouse Ig lambda PE, and anti-mouse IgD Pacific Blue, anti-mouse CD23 PE (BioLegend). Live dead aqua stain was used to separate dead cells (Life Technologies).

B cell-sorting. Memory B cells of immunized knock-in mice were single cell sorted as previously described. Dosenovic, et al., Cell 161, 1505-1515 (2015). In brief, splenocytes were stained with anti-mouse CD4 PE-CF594, anti-mouse CD8 PE-CF594, anti-mouse Ly-6G and Ly-6C (Gr1) PE-CF594, anti-mouse IgG1 BV421 (BD biosciences), anti-Hu/Mo B220 FITC, anti-mouse CD38 A700, anti-mouse IgM PerCP-eFluor 710 (eBiosciences) and PE-Streptavidin conjugated 426c.TM4ΔV1-3 gp140-biotin and APC-Streptavidin conjugated 426c.TM4ΔV1-3.D368R.E370A-biotin (426c.TM4ΔV1-3 gp140-KO). Live dead aqua stain was used to separate dead cells (Life Technologies). The sorted cells were live cells, CD4−, CD8−, Gr-1−, B220+, CD38+, IgM−, IgG1+, 426c.TM4ΔV1-3 gp140+, 426c.TM4ΔV1-3 gp140-KO$^-$. The VDJ knock-in sequence was amplified by nested PCR using the following primer pairs; 1_3 BNC60_F_HK GGGATGGTCATGTAT-CATCCTTTTTCTAG (SEQ ID NO: 128) with 1mRG AGAAGGTGTGCACACCGCTGGAC (SEQ ID NO: 129) and 2_3 BNC60_F_HK GTAGCAACTGCAACCGGTGTACATTCT (SEQ ID NO: 130) with 2mRG GCTCAGGGAARTAGCCCTTGAC (SEQ ID NO: 131). The VJ knock-in sequence was amplified by nested PCR using the following primer pairs; SEQ ID NO: 128 with 1mRK ACTGAGGCACCTCCAGATGTT (SEQ ID NO: 132) and SEQ ID NO: 130 with 2mRK TGGGAAGATGGATACAGTT (SEQ ID NO: 133).

Immunizations. 6-8 weeks old female or male WT and gl3BNC60 knock-in mice were immunized with 10 µg of rEnv. 3-5 mice/group were used in each experiment. Immunizations of 426c gp140, gp120-dextramer and gp140-dextramer were performed with Imject Alum (Thermo Scientific). Immunizations with gp120-dextramer were also performed with Ribi (Sigma). Immunizations with gp120 were performed with Ribi. Serum was collected for analysis at two weeks after immunization. No randomization or blinding of the experiments were performed. All experiments were performed according to the protocols approved by the IACUC at Rockefeller University. In the case of immunizations with dextrameric Env, the dextrameric complexes were formed for 10-15 min before the addition of Alum or Ribi. All experiments were performed according to the protocols approved by the IACUC at Rockefeller University.

Serum ELISA. High binding 96-well plates (Corning Incorporated) were coated with 200 ng/well of 426c.TM4

ΔV1-3 and 426c.TM4 ΔV1-3 CD4-BS KO (Corning Incorporated) with 200 ng/well of protein. After incubation overnight (ON) at 4° C., plates were washed in wash buffer (3× in PBS with 0.05% TWEEN 20 (Sigma)) and blocked in blocking buffer (PBS with 2% milk). Serum samples were added to coated wells at the indicated dilutions and incubated for 1 hr at 37° C. Plates were washed and secondary antibody, HRP conjugated anti-mouse (Jackson Immuno Research), was added and incubated for 30 minutes at 37° C. Plates were washed again and then developed by adding ABTS solution (Life Technologies) and the absorbance was measured at 405 nm using a FLUOstar Omega microplate reader (BMG Labtech) which gives a maximum reading of 4.0.

Neutralization Assay. Serum IgG were tested against a panel of HIV-1 pseudoviruses using the TZM-bl neutralization assay as previously described. Li, et al., J. of Virol. 79, 10108-10125 (2005).

Capture ELISA: Plasmids expressing 426c.N276D.N460D.N463D, Q168a2.N462D.N465D, Q461e2.N276D.N463D, Bal. N276D. N463D, 823c.N276D.N463D, and 706c.N276D.N463D gp160 proteins were transfected into 293 cells using GeneJuice (Merck Millipore) according to the manufacturer's instructions. 72 h later, the cells were lysed with PBS containing 1% Triton X-100. Cell lysates were clarified by centrifugation, passed through a 0.2 µM filter, and then incubated in triplicate on ELISA plates coated with the anti-C-terminal D7324 anti-gp120 sheep antibody (Aalto Bioreagents). ELISA was performed with mature and gl NIH45-46 and VRC01 as previously described. Hoot, et al., Recombinant HIV envelope proteins fail to engage gl versions of anti-CD4bs bNAbs. PLoS pathogens 9, e1003106 (2013).

Figure 5A:
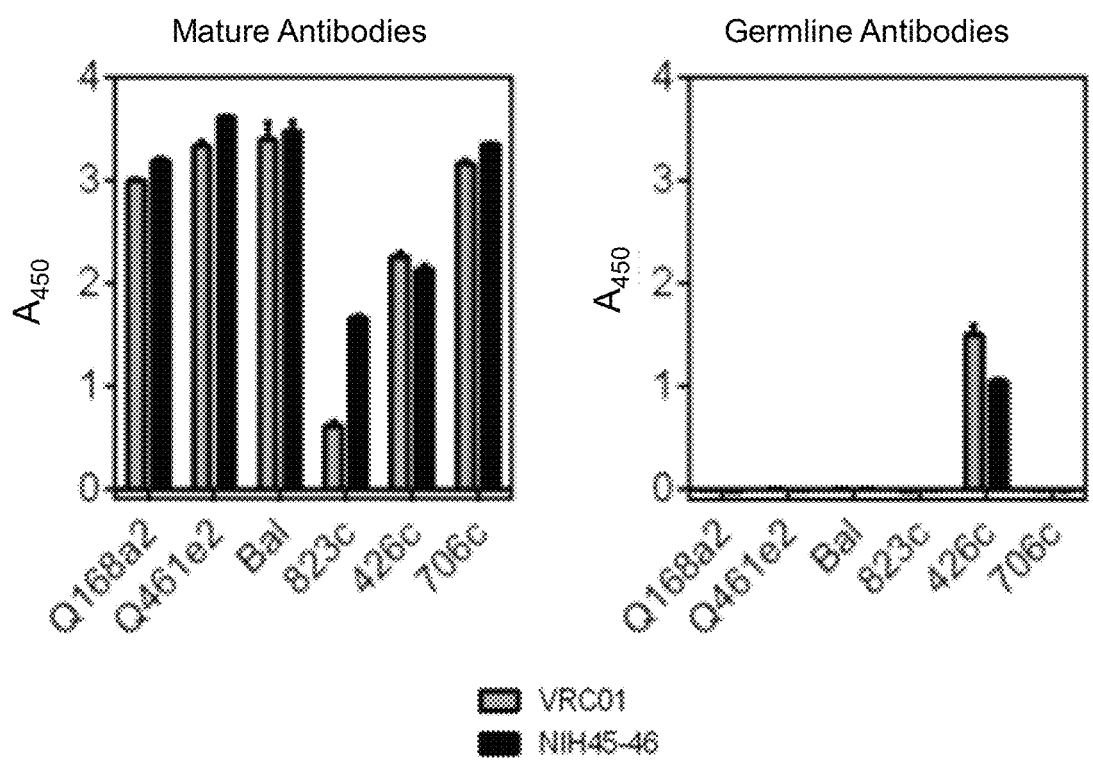
FIGS. 5A and 5B. Germline VRC01-class antibody-binding to 426c gp120 variants.
Figure 5B:
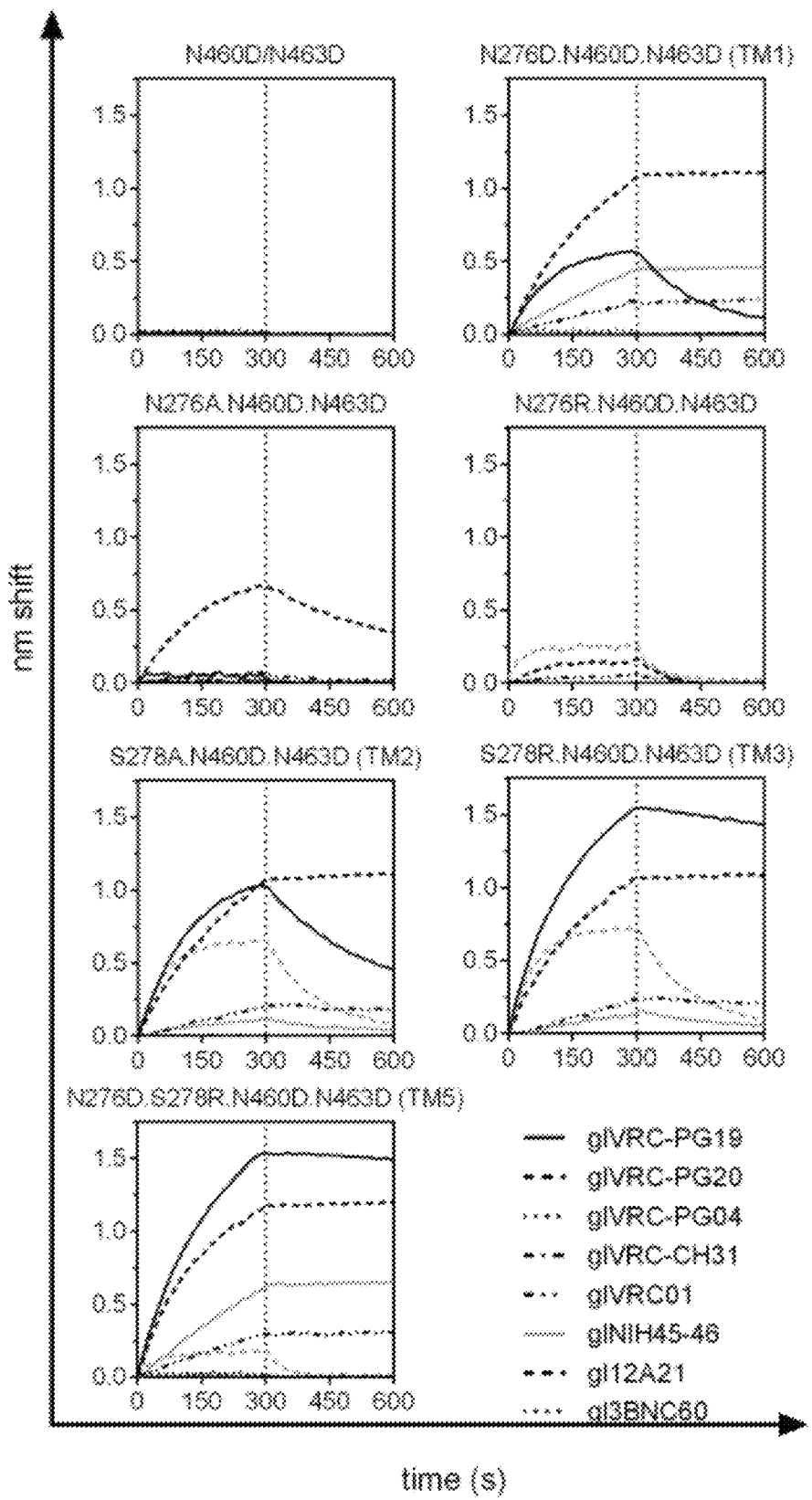

The disruption of the NLGS at position 276 (N276D) from the clade C recombinant Env 426c, results in glVRC01 and glNIH45-46 antibody-binding. McGuire, et al., J. Exp. Med. 210, 655-663 (2013). The parallel disruption of two NLGS in V5 (positions 460 and 463) improves this binding; although by themselves N460D and N463D are insufficient to confer glVRC01- or glNIH-45-46-binding. McGuire, et al., J. Exp. Med. 210, 655-663 (2013). The 426c Env lacking these three NLGS is referred to as a "triple mutant 1" (TM1) or "426c.NLGS.TM1Δ1-3" as compared to 426c.NLGS.TM4Δ1-3. The disruption of the 276 and V5 NLGS from other Envs does not result in glVRC01-binding (FIG. 5A) indicating that additional constraints are present on these Envs that prevent glVRC01-binding. Because of its ability to engage certain glVRC01-class BCRs in vitro, TM1 is a logical immunogen to target naïve B cells expressing glVRC01-class BCRs in vivo. Here it is reported that TM1 is also recognized by two additional, clonally-related, glVRC01-class antibodies, glVRC-PG19 and glVRC-PG20 (FIG. 5B, and FIG. 15). However, other gl-reverted members of the VRC01-class antibodies such as: 12A21, 3BNC60, VRC-CH31, or VRC-PGV04 do not bind TM1 (FIGS. 5A, 5B, 6A, 6B, and FIG. 15).

The reasons for the differential recognition of TM1 by the different glVRC01-class antibodies are not well understood. Information on this topic will help to better understand the features of Env that prevent the engagement of the various glVRC01-class BCRs in the context of HIV-1 infection and will facilitate the design of immunogens capable of activating a broader range of these receptors.

Although the VH domains of all known VRC01-class bNAbs are derived from the VH1-2*02 allele and a few J genes, their CDRH3 regions differ extensively in amino acid sequence and length. Zhou, et al., Structural Repertoire of HIV-1-Neutralizing Antibodies Targeting the CD4 Supersite in 14 Donors. Cell (2015); Scheid, et al., Science 333, 1633-1637 (2011); Wu, et al., Science 333, 1593-1602 (2011); Wu, et al., Cell 161, 470-485 (2015); Georgiev, et al., Science 340, 751-756 (2013). Therefore, one possible explanation for the differential recognition of TM1 by different members of the glVRC01-class antibodies may be due to the different CDRH3 regions expressed by these antibodies. It is also possible that the above-mentioned differences in TM1 recognition by the various glVRC01-class antibodies is linked to the different light chains (LCs) used by these antibodies. Relevant to the latter possibility is the observation that when the gl heavy chains (glHCs) of 3BNC60 and gl12A21 are paired with the gl light chains (glLC) of VRC01/NIH45-46, the chimeric antibodies bind TM1. McGuire, et al., J. Exp. Med. 210, 655-663 (2013).

These results suggest that the glLCs of 12A21 and 3BNC60 (derived from Vκ1-33 while those of VRC01/NIH45-46 are derived from Vκ3-11) are incompatible with TM1-binding. The N to D substitutions used to generate TM1, were initially selected to maintain structural similarity at positions 276, 460 and 463. However, they introduce negative charges at those positions; which potentially create unfavorable electrostatic interactions with the more negatively-charged CDRLs on the glLCs of 12A21 and 3BNC60 (as compared to the CDRL regions of the VRC01/NIH45-46 glLC; FIG. 7, SEQ ID NOs: 135-140). Different amino acids at position 276 were therefore introduced and their effect on glAb-binding was examined (FIG. 5B and FIG. 15). On the background of the 426c.N460D.N463D, which does not bind glVRC01-class antibodies (FIG. 5B), the substitution of N276 either by an alanine, which introduces a neutral charge, or by an arginine, which introduces a positive charge, results in a drastic reduction in binding of glVRC01, glNIH45-46, glVRC-PG19, and glVRC-PG20 relative to TM1. However, the N276R mutation conferred weak but detectable binding to gl12A21 (FIG. 5B). It was concluded that the nature of the amino acid at position 276 influences the interactions between 426c and glVRC01 class bNAbs. Specifically, a negative charge at position 276 may be favored over a neutral or positive charge by glVRC01, glNIH45-46, glVRC-PG19, and glVRC-PG20, but that the negative charge is incompatible with gl12A21-binding.

Alternatively, the NLGS at position 276 was disrupted by mutating S278. Interestingly, a S278A substitution (TM2) conferred gl12A21 binding, while it reduced binding of glNIH45-46, glVRC01, and glVRC-PG20, and improved binding of glVRC-PG19 compared to TM1 (although this Ab still had a relatively fast off rate) (FIG. 5B and FIG. 15). A S278R substitution (TM3) had a similar overall effect as the S278A substitution, but the binding of glVRC-PG20 and glVRC-PG19 was improved, the latter having a slower off rate than the one recorded with the S278A mutation compared to TM1 (FIG. 5B and FIG. 15). The combination of N276D and S278R conferred weak gl12A21-binding, but improved glNIH45-46-binding (FIG. 5B) compared to TM1. It was concluded that gl12A21 displays preferential binding to 426c variants with an N at position 276. In contrast, glVRC-PG19, glVRC01 and glNIH45-46 can accommodate either an N or D at that position. Thus, the absence of an NLGS at position 276 is important for glVRC01, glNIH45-46, glVRC-PG19/20 and gl12A21 binding, but the specific amino acid requirements at positions 276 and 278 differ among these antibodies. Binding of gl3BNC60, glVRC-CH31 and glVRC-PGV04 was not recorded to any of these modified Envs (FIGS. 5A, 5B, 6A, 6B, and FIG. 15).

In addition to the S278R modification discussed above, Jardine et al., identified a combination of five additional amino acid mutations (L260F, K357R, I371F, N386D, and G471S) which on the background of the engineered outer domain of eOD-base (which also contains the N276D and the N463D modifications) resulted in eOD-GT6 that bound glVRC01, glNIH45-46, glVRC-PG19/20 and gl12A21, and to gl3BNC60, glVRC-CH31 and glVRC-PG04. Jardine, et al., Science 340, 711-716 (2013).

eOD-GT6 is derived from HxB2 which is a CXCR4-tropic tier 1 virus while TM1 is a CCR5-tropic tier 2 virus. Furthermore, TM1 includes the outer and inner domains of gp120, while eOD-GT6 is designed to recapitulate only the outer domain structure of Env. Therefore it was assessed whether these additional mutations would improve binding of glVRC01 class Abs on the background of TM1 as they did on eOD-GT6. On the TM1 background the combination of these six mutations abrogated the binding of all glVRC01-class antibodies tested (FIG. 8 "TM1+eOD-GT6") as compared to TM1 (FIG. 8, top left panel)._When these mutations were introduced individually the K357R and N386D mutations displayed similar binding to that of TM1, while the L260F mutation was found to be detrimental (FIG. 8). The G471S mutation improved the binding of glVRC-PG19, and the I371F mutation improved the binding of glVRC-PG20 but reduced the binding of glVRC-PG19 (FIG. 8). The S278R mutation was discussed above. The S278R+G471S combination resulted in slightly improved binding to that observed with the S278R mutation (FIG. 8). In sum, binding of glVRC01, glNIH45-46, glVRC-PG19, glVRC-PG20 and gl12A21 was observed when the S278R or S278R+G471S mutations were introduced on the background of the N276D, N460D and N463D mutations ("TM5" FIG. 8). The affinity of glVRC01-class antibody binding to selected trimeric variants of the Envs mentioned above (FIG. 15) was measured. None of these mutations conferred binding to gl3BNC60, glVRC-PG04 or glVRC-CH31 (FIGS. 6A, 6B, and FIG. 15).

The lengths and glycosylation patterns of variable regions 1, 2 and 3 of gp120 (V1, V2, V3 respectively) influence the accessibility of diverse mature anti-CD4-BS antibodies. Deletion of the V1, V2 and V3 from TM1 gp140 improves the activation of B cells expressing the glNIH45-46 BCR. McGuire, et al., Science 346, 1380-1383 (2014). To investigate whether these regions restrict binding to glVRC01 class antibodies on various modified 426c constructs, versions of TM1, TM4 and TM5 lacking V1, V2 and V3 (ΔV1-3) were engineered. gl3BNC60-binding to TM4ΔV1-3 and TM5ΔV1-3 (FIG. 6A and FIG. 15) was observed while removal of the variable regions from TM5 conferred binding to glVRC-CH31. To define the role of the individual variable regions of Env in restricting the binding of the gl3BNC60 antibody, versions of TM4 lacking these regions individually, or in various combinations (FIG. 9) were engineered. Although the individual removal of V1, V2 or V3 did not result in detectable gl3BNC60-binding, the simultaneous removal of the V1 and V2 regions did result in such binding. The additional removal of V3 modestly improved gl3BNC60-binding. It was concluded that with the exception of glVRC-PG04, the removal of V1/V2 from TM4 improves and expands its binding capabilities to glVRC01-class Abs and that the V1/V2 region imposes an additional constraint to gl3BNC60-binding compared to the other glVRC01-class Abs examined. It was therefore concluded that despite the 'similar' structural features and similar recognition patterns of mutated VRC01-class bNAbs, (Zhou, et al., Structural Repertoire of HIV-1-Neutralizing Antibodies Targeting the CD4 Supersite in 14 Donors. Cell (2015); Diskin, et al., Increasing the Potency and Breadth of an HIV Antibody by Using Structure-Based Rational Design. Science (2011); Zhou, et al. Science 329, 811-817 (2010); Zhou, et al., Immunity 39, 245-258 (2013)) the gl antibodies display distinct requirements for Env-binding, suggesting that the gl forms of these antibodies have different angles of approach for the CD4-BS.

Mice, rats, rabbits and NHPs do not express a human VH1-2*02 ortholog and thus are not suitable to evaluate immunogens designed to stimulate glBCRs of VRC01-class Abs. Jardine, et al., Science 340, 711-716 (2013); West, et al., PNAS 109, E2083-2090 (2012); Tran, et al., PNAS 111, E738-747 (2014). To study the activation of naïve B cells expressing the predicted gl version of a VRC01-class Ab in vivo, knock-in mice homozygous for the VH and VL of gl3BNC60 (gl3BNC60-KI) were engineered. Because gl3BNC60 has the lowest binding affinity for TM4ΔV1-3 among the glVRC01-class antibodies tested (FIGS. 6A, 6B, and FIG. 15), it was reasoned that in vivo activation of B cells expressing the gl3BNC60 BCR should also translate into the activation of B cells expressing the other glVRC01-class BCRs that display stronger binding to this Env (i.e. glVRC01 or gl12A21).

In contrast to WT mice, gl3BNC60 KI mice showed very few $IgD^{+}IgM^{+}$ B cells in the bone marrow (FIG. 10A) a phenotype displayed by mice with autoreactive B cells, (Nemazee & Burki, Nat. 337, 562-566 (1989); Goodnow, et al., Nat. 334, 676-682 (1988)) such as those expressing the mutated forms of the HIV-1 neutralizing antibodies 2F5 or 4E10. Finton, et al., Autoreactivity and exceptional CDR plasticity (but not unusual polyspecificity) hinder elicitation of the anti-HIV antibody 4E10. PLoS pathogens 9, e1003639 (2013); Chen, et al., J. Immunol. 191, 1260-1275 (2013); Doyle-Cooper, et al., J. Immunol. 191, 3186-3191 (2013). Thus, despite the fact that soluble gl3BNC60 IgG is not polyreactive (Scheid, et al., Science 333, 1633-1637 (2011)), this BCR is unable to support normal levels of B cell development in knock mice. Although B cell development was altered in gl3BNC60 KI mice, B cells survive and populate the spleen. Splenic B cells in the knock in mouse were skewed towards a marginal zone phenotype ($CD21^{high}$, $CD23^{low}$), in contrast to the WT which were mostly follicular B cells ($CD21^{low}$, $CD23^{high}$) (FIG. 10B). Consistent with the idea that the knock in BCR is selected against, the majority of B cells in the spleen of the gl3BNC60 KI mice express an endogenous lambda light chain, rather than the exogenous kappa light chain (FIG. 11A). Thus, only a small fraction of the B cells in gl3BNC60 KI mice express the fully human gl3BNC60 BCR.

WT or gl3BNC60 KI mice were immunized with the soluble gp140 trimeric form (gp140) of TM4ΔV1-3 Env (FIGS. 10C, and 12A). Pre-immune serum IgG from the gl3BNC60 KI mice or the WT mice did not display reactivity to TM4ΔV1-3 Env. All three WT animals produced Ag-specific IgG after a single immunization, while two immunizations were required for Ag-specific IgG production by the gl3BNC60 KI mice and only two of three animals responded. The relative inefficiency by which soluble trimeric gp140 TM4ΔV1-3 induces Ab production in the KI mice, might be related to its fast off rate, or to B cell anergy associated with autoreactivity. Goodnow, et al., Nat. 334, 676-682 (1988); Cooke, et al., The J. of Exp. Med. 179, 425-438 (1994).

The ability of antigens with low binding affinities (due to fast off rates) to activate B cells can be improved by increasing their valency. Batista & Neuberger, Immunity 8, 751-759 (1998). Mutlimerizing an antigen can also overcome poor B cell responses related to anergy in a manner that allows these B cells to receive T cell help and to produce somatically hypermutated BCRs and antibodies displaying no, or limited autoreactivity. Cooke, et al., The J. of Exp. Med. 179, 425-438 (1994); Sabouri, et al., PNAS, 111, E2567-2575 (2014). To that end, the following multimerization approaches were tested with the TM4ΔV1-3 construct: (a) a dextran-based antigen-multimerization approach that can lead to up to 70 Env molecules per dextran molecule. This approach was previously used to stimulate B cells in knock-in mice expressing the gl 3BNC60 HC only (gl3BNC60 HC) (Dosenovic, et al., Cell 161, 1505-1515 (2015)); (b) addition of the multimerization domain of the human C4b-binding protein to the carboxy terminus of Env (this approach leads to the formation of ring-like structures expressing seven Env molecules) (Hofmeyer, et al., J. of Mol. Biol. 425, 1302-1317 (2013)); and (c) a ferritin-based approach, which leads to the formation of particles with 24 copies of Env. Kanekiyo, et al., Cell 162, 1090-1100 (2015).

Figure 10C:
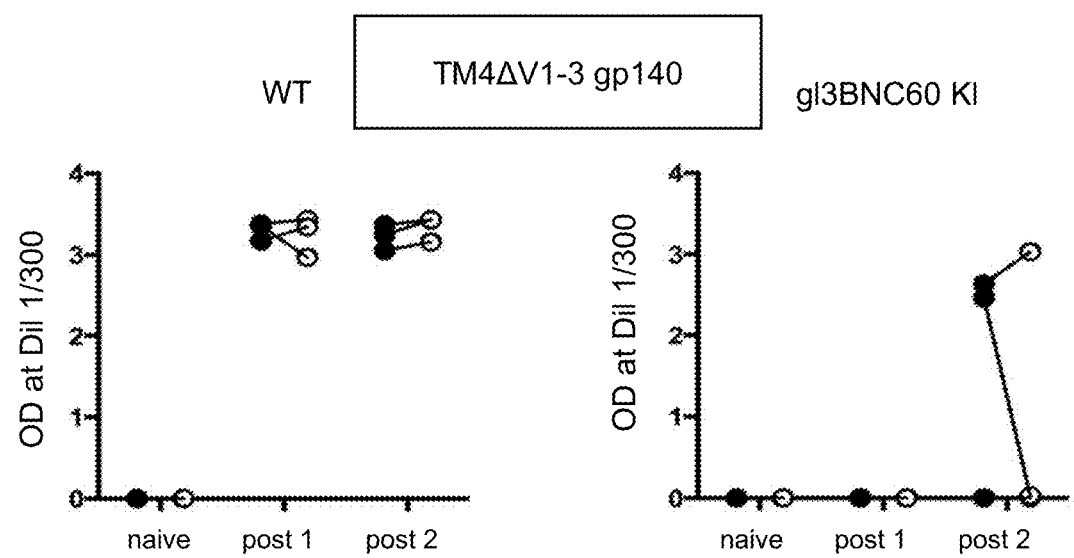
Figure 10H:
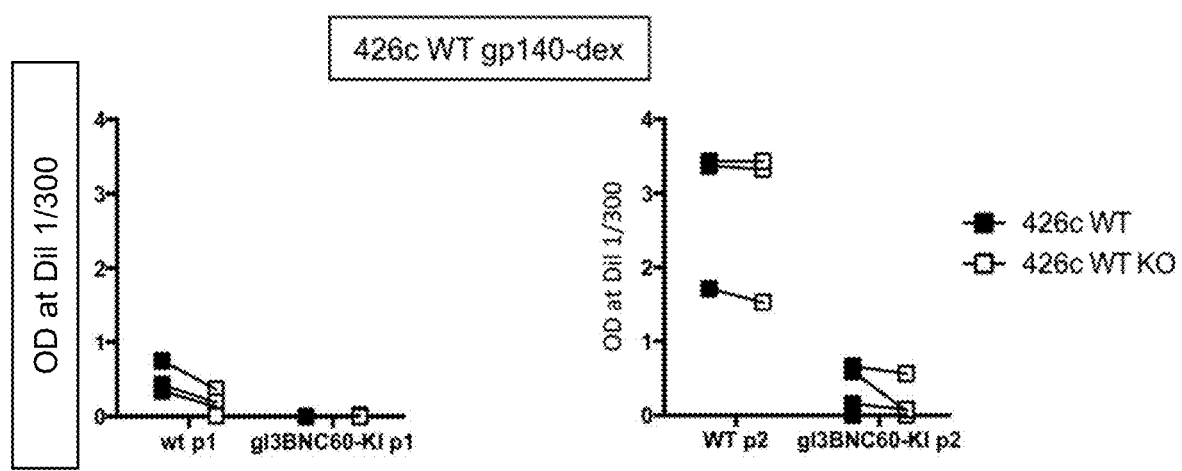
Figure 11A:
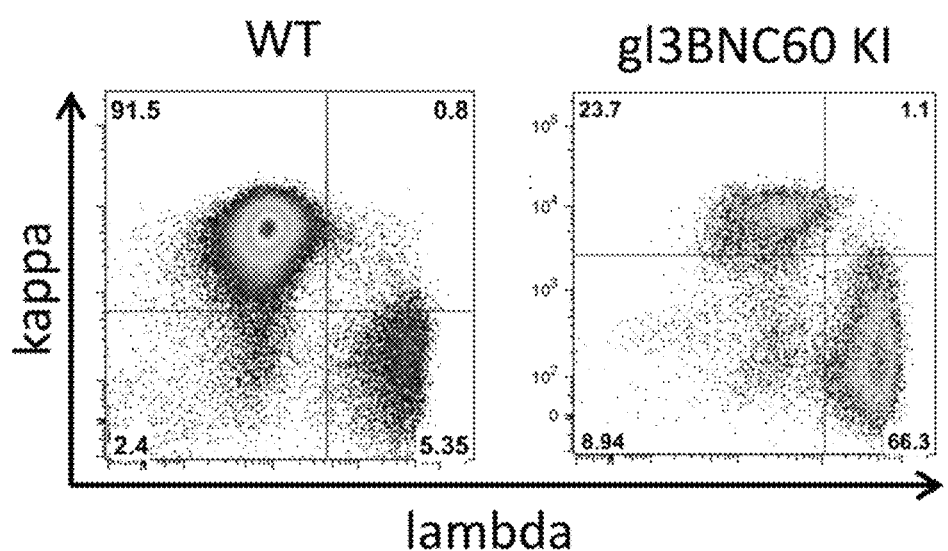
Figure 11B:
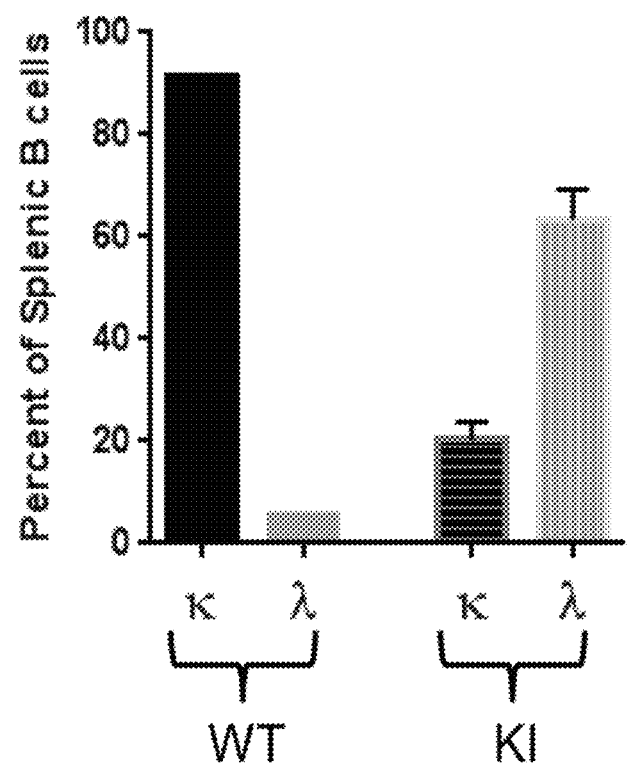
Figure 12A:
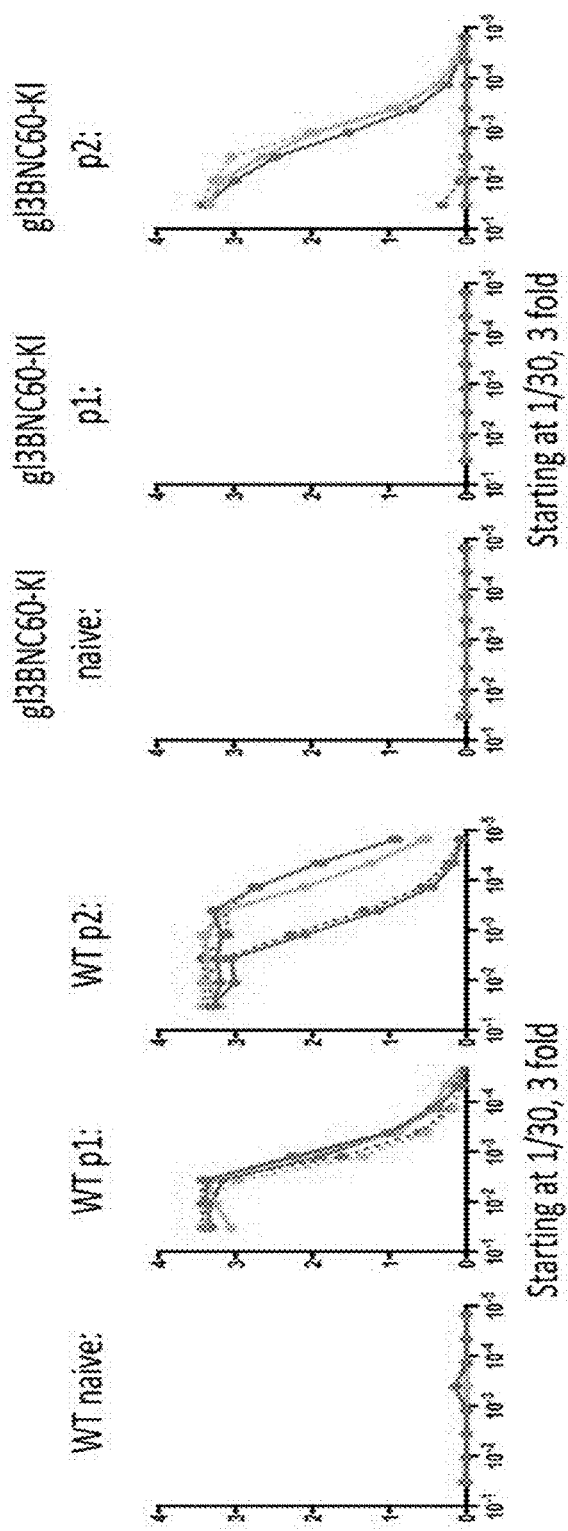
FIGS. 12A-12F. Antibody responses elicited in WT and knock-in gl3BNC60 mice after immunization.
Figure 12B:
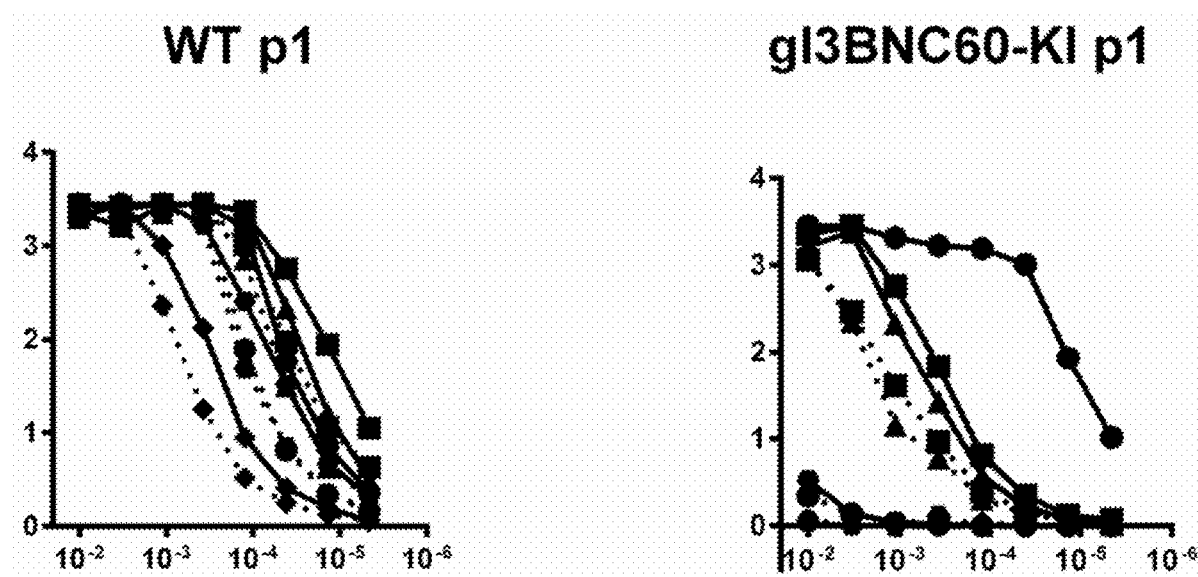
Figure 12C:
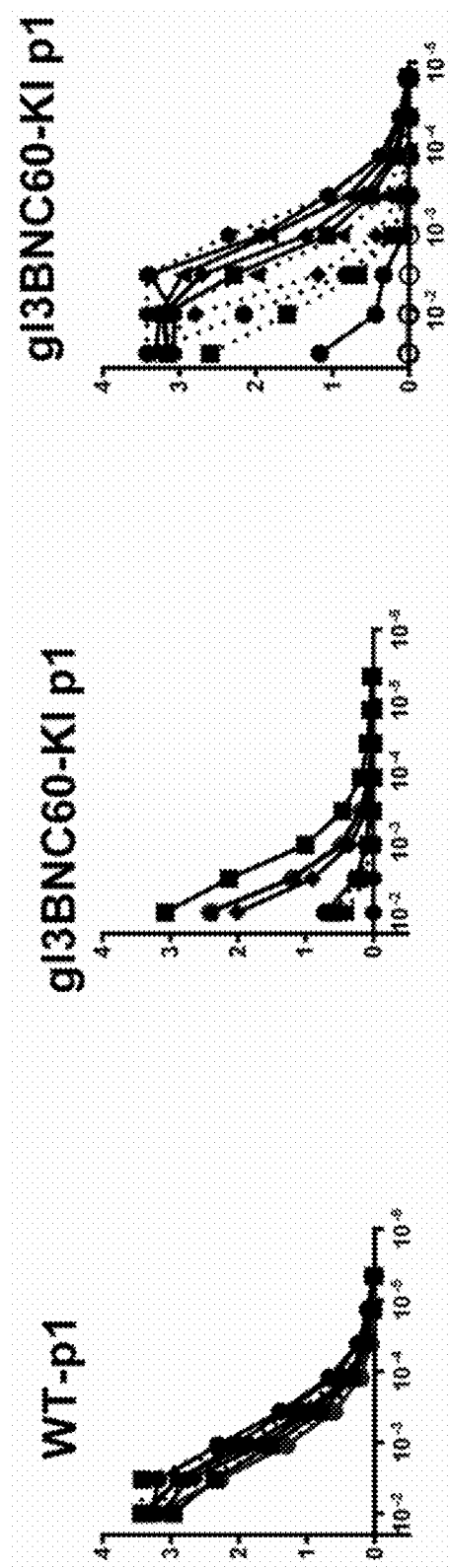
Figure 12D:
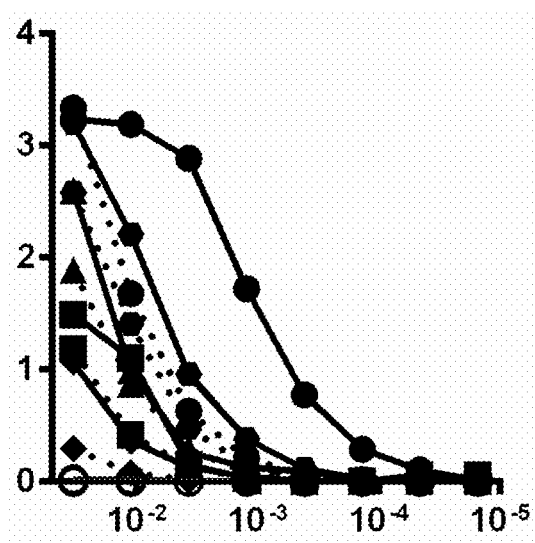
Figure 12E:
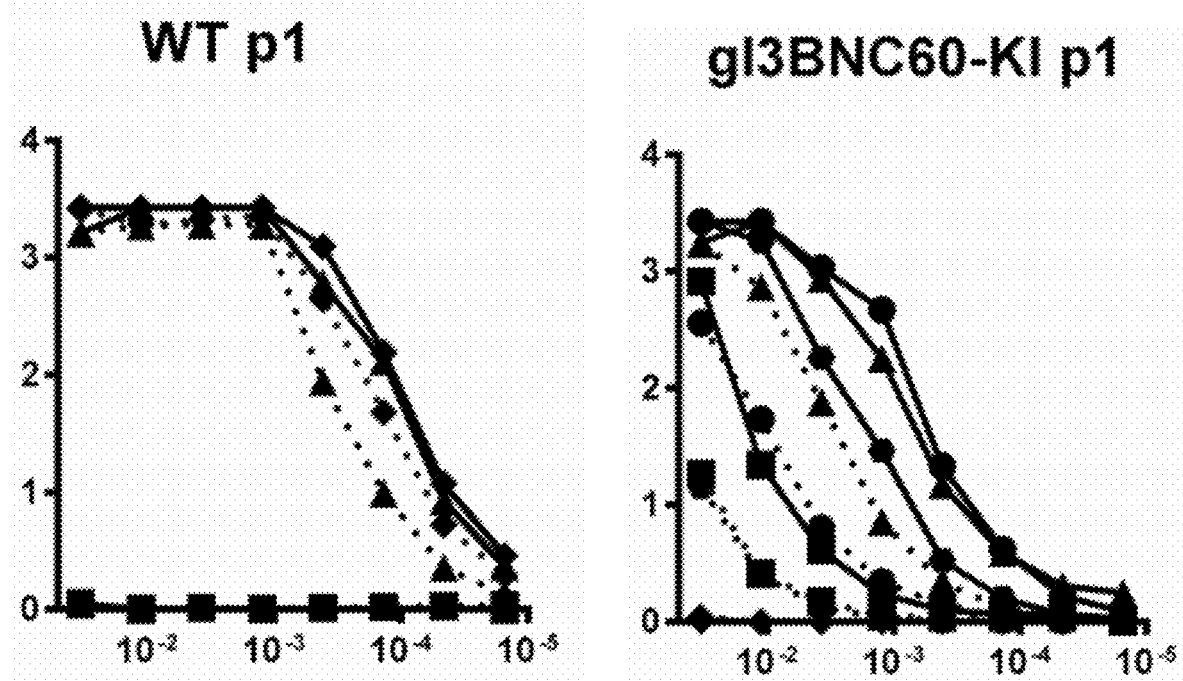
Figure 12F:
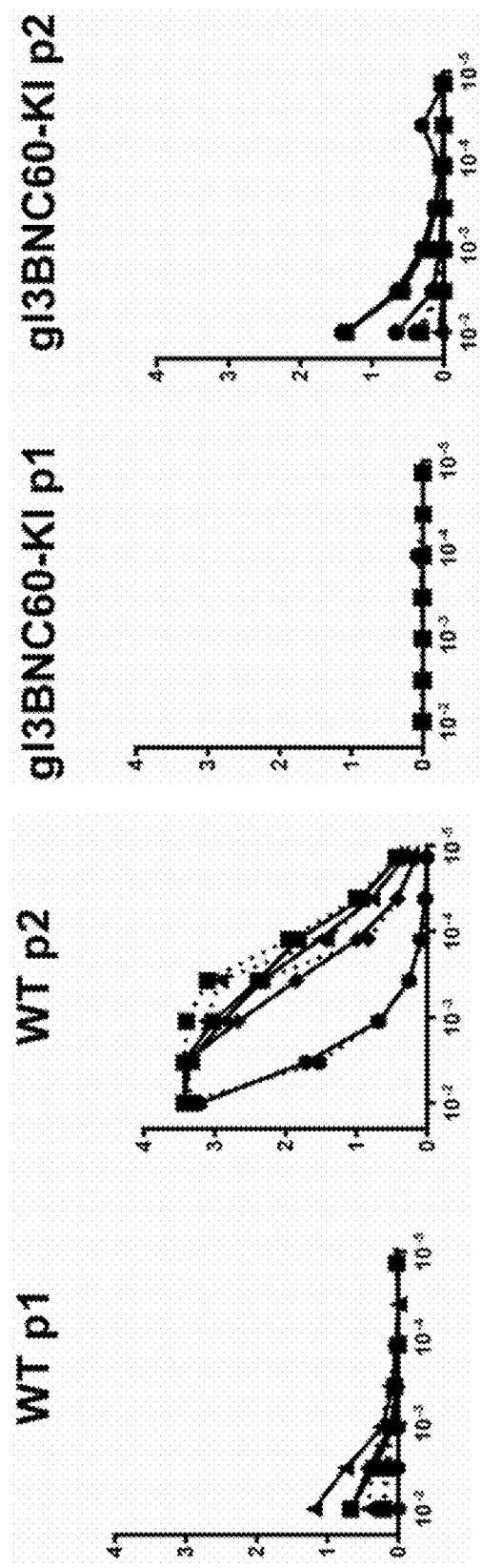
Figure 13A:
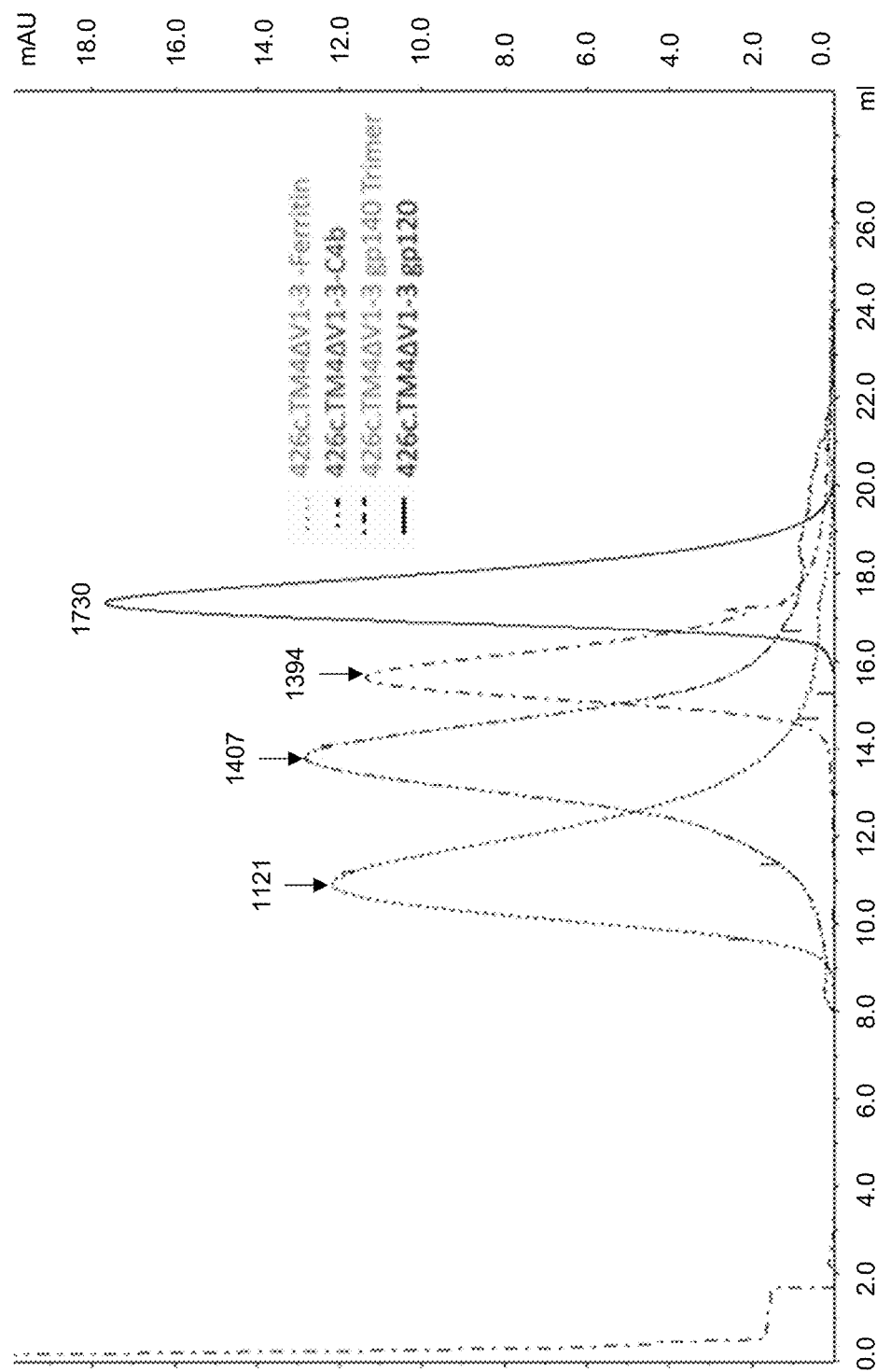
FIGS. 13A and 13B. Biochemical characterization of 426cTM4ΔV1-3 multimers.
Figure 13B:
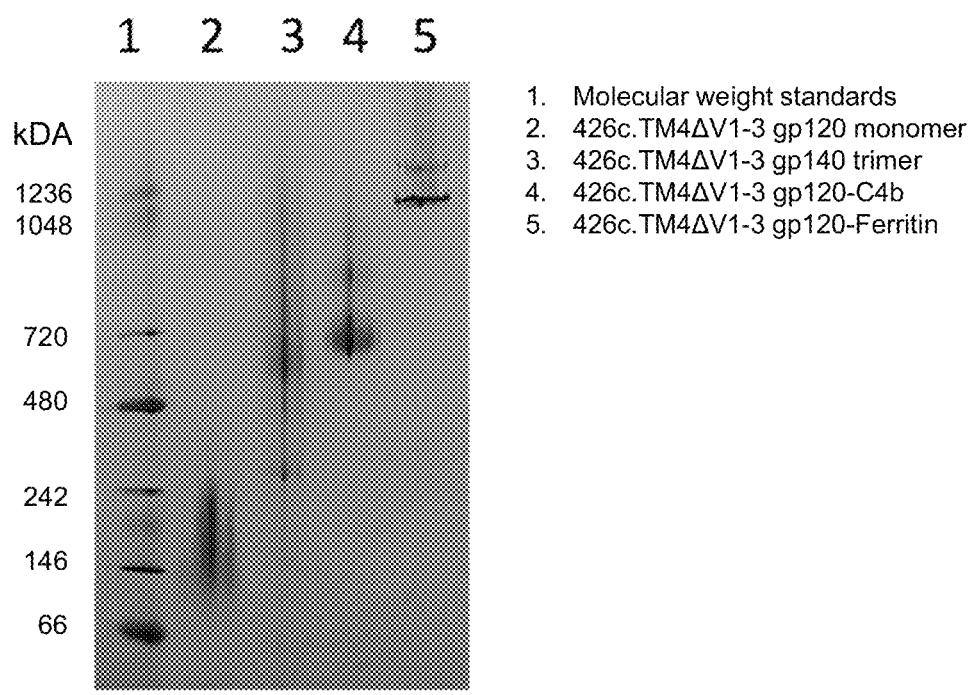

WT or gl3BNC60 KI mice were immunized with dextrameric gp140 (gp140-dex) (FIGS. 10D and 12B); dextrameric gp120 (gp120-dex) (FIGS. 10E and 12C); heptameric gp120 (gp120-C4b) (FIGS. 10F and 12D) and ferritin-gp120 (gp120-ferritin) (FIGS. 10G and 12E). The protein based multimerization approaches show differences in size by SEC (FIG. 13A) and BN-PAGE (FIG. 13B). A single immunization with the multimerized Env constructs was sufficient to elicit immunogen-specific antibody responses (filled circles) in the majority (21 out of 24) of gl3BNC60 KI animals (3/5 in gp140-dex, 9/10 in gp120-dex, 5/5 in gp120-C4b, and 4/5 in gp120-ferritin) (FIGS. 10D, 10E, 10F, 10G, 12B, 12C, 12D and 12E respectively). gl3BNC60 KI and WT mice were also immunized with dextrameric WT gp140 (FIGS. 10H and 12F). Three of four WT animals generated serum IgG responses to this immunogen (including CD4-BS antibodies) after a single immunization (FIGS. 10H, left panel and 12F). In contrast, none of the gl3BNC60 KI mice generated a detectable antibody response. A second immunization boosted the anti-Env antibodies in the WT mice and induced low responses in gl3BNC60 KI mice, but decreased the relative proportion of the CD4-BS directed antibodies in the WT response (FIGS. 10H, right panel and 12F). With the exception of one animal in the gp120-ferritin group (FIGS. 10G and 12E) the WT animals also responded after a single immunization (FIGS. 10D, 10E, 10F, 10G, 12B, 12C, 12D and 12E). It was concluded that (i) the 426c modifications that are necessary for the binding of gl3BNC60 antibody to TM4ΔV1-3 lead to the stimulation of naïve B cells expressing gl3BNC60 BCRs in v prise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in an e/m Env's ability to induce an immune response (e.g., B-cell activation as measured by $Ca^{2+}$ flux).

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. An engineered and multimerized (e/m) human immunodeficiency virus (HIV) envelope glycoprotein (Env) comprising: (i) mutations, using HXB2 numbering: N460D, N463D, S278R, and G471S; and (ii) removal of the V1 loop and the V2 loop wherein the e/m Env does not include a mutation at residue 276.

2. The e/m HIV Env of claim 1, further comprising mutations V65C and S115C.

3. The e/m HIV Env of claim 1, wherein removal of the V1 loop comprises removal of residues 131-152 and/or removal of the V2 loop comprises removal of residues 161-196.

4. The e/m HIV Env of claim 1, wherein removal of the V1 loop and removal of the V2 loop comprises removal of residues 123-196.

5. The e/m HIV Env of claim 1, further comprising removal and replacement of the V3 loop with a flexible linker.

6. The e/m HIV Env of claim 5, wherein the V3 loop comprises residues 296-331.

7. The e/m HIV Env of claim 5, wherein the flexible linker is selected from SEQ ID NOs: 3-13, or 126.

8. The e/m HIV Env of claim 1, further comprising an N-terminal truncation before residue 49, 48, 47, 46, 45, 44, 43, 42, 41, 40 or 39.

9. The e/m HIV Env of claim 1, further comprising a C-terminal truncation after residue 499, 498, 497, 496, 495, 494, 493, 492, 491, 490 or 389.

10. The e/m HIV Env of claim 1, further comprising a multimerization domain.

11. The e/m HIV Env of claim 10, wherein the multimerization domain is a C4b multimerization domain selected from SEQ ID NOs. 14-46 or a heptamerization domain selected from SEQ ID NOs. 47-49.

* * * * *

SEQUENCE LISTING

<160> NUMBER OF SEQ ID NOS: 148

<210> SEQ ID NO 1
<211> LENGTH: 847
<212> TYPE: PRT
<213> ORGANISM: Human immunodeficiency virus 1

<400> SEQUENCE: 1

```
Met Arg Val Lys Gly Ile Arg Lys Ser Tyr Gln Tyr Leu Trp Lys Gly
1               5                   10                  15

Gly Thr Leu Leu Leu Gly Ile Leu Met Ile Cys Ser Ala Val Glu Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu His Phe Asn Met Trp Lys
                85                  90                  95

Asn Asn Met Val Glu Gln Met Gln Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Lys Asp Val Asn Ala Thr Asn Thr Thr Asn Asp Ser Glu Gly
    130                 135                 140

Thr Met Glu Arg Gly Glu Ile Lys Asn Cys Ser Phe Asn Ile Thr Thr
145                 150                 155                 160

Ser Ile Arg Asp Glu Val Gln Lys Glu Tyr Ala Leu Phe Tyr Lys Leu
                165                 170                 175

Asp Val Val Pro Ile Asp Asn Asn Asn Thr Ser Tyr Arg Leu Ile Ser
            180                 185                 190

Cys Asp Thr Ser Val Ile Thr Gln Ala Cys Pro Lys Ile Ser Phe Glu
        195                 200                 205

Pro Ile Pro Ile His Tyr Cys Ala Pro Ala Gly Phe Ala Ile Leu Lys
    210                 215                 220

Cys Asn Asp Lys Thr Phe Asn Gly Lys Gly Pro Cys Lys Asn Val Ser
225                 230                 235                 240

Thr Val Gln Cys Thr His Gly Ile Arg Pro Val Val Ser Thr Gln Leu
                245                 250                 255

Leu Leu Asn Gly Ser Leu Ala Glu Glu Val Val Ile Arg Ser Asp
            260                 265                 270

Asn Phe Thr Asn Asn Ala Lys Thr Ile Ile Val Gln Leu Lys Glu Ser
        275                 280                 285

Val Glu Ile Asn Cys Thr Arg Pro Asn Asn Thr Arg Lys Ser Ile
    290                 295                 300

His Ile Gly Pro Gly Arg Ala Phe Tyr Thr Thr Gly Glu Ile Ile Gly
305                 310                 315                 320

Asp Ile Arg Gln Ala His Cys Asn Ile Ser Arg Ala Lys Trp Asn Asp
                325                 330                 335

Thr Leu Lys Gln Ile Val Ile Lys Leu Arg Glu Gln Phe Glu Asn Lys
            340                 345                 350

Thr Ile Val Phe Asn His Ser Ser Gly Gly Asp Pro Glu Ile Val Met
        355                 360                 365
```

```
His Ser Phe Asn Cys Gly Gly Glu Phe Phe Tyr Cys Asn Ser Thr Gln
    370                 375                 380

Leu Phe Asn Ser Thr Trp Asn Asn Thr Glu Gly Ser Asn Asn Thr
385                 390                 395                 400

Glu Gly Asn Thr Ile Thr Leu Pro Cys Arg Ile Lys Gln Ile Ile Asn
                405                 410                 415

Met Trp Gln Glu Val Gly Lys Ala Met Tyr Ala Pro Pro Ile Arg Gly
            420                 425                 430

Gln Ile Arg Cys Ser Ser Asn Ile Thr Gly Leu Leu Thr Arg Asp
                435                 440                 445

Gly Gly Ile Asn Glu Asn Gly Thr Glu Ile Phe Arg Pro Gly Gly Gly
    450                 455                 460

Asp Met Arg Asp Asn Trp Arg Ser Glu Leu Tyr Lys Tyr Lys Val Val
465                 470                 475                 480

Lys Ile Glu Pro Leu Gly Val Ala Pro Thr Lys Ala Lys Arg Arg Val
                485                 490                 495

Val Gln Arg Glu Lys Arg Ala Val Gly Ile Gly Ala Val Phe Leu Gly
                500                 505                 510

Phe Leu Gly Ala Ala Gly Ser Thr Met Gly Ala Ala Ser Met Thr Leu
            515                 520                 525

Thr Val Gln Ala Arg Leu Leu Leu Ser Gly Ile Val Gln Gln Asn
    530                 535                 540

Asn Leu Leu Arg Ala Ile Glu Ala Gln Gln Arg Met Leu Gln Leu Thr
545                 550                 555                 560

Val Trp Gly Ile Lys Gln Leu Gln Ala Arg Val Leu Ala Val Glu Arg
                565                 570                 575

Tyr Leu Gly Asp Gln Gln Leu Leu Gly Ile Trp Gly Cys Ser Gly Lys
                580                 585                 590

Leu Ile Cys Thr Thr Ala Val Pro Trp Asn Ala Ser Trp Ser Asn Lys
            595                 600                 605

Ser Leu Asp Arg Ile Trp Asn Asn Met Thr Trp Met Glu Trp Glu Arg
    610                 615                 620

Glu Ile Asp Asn Tyr Thr Ser Glu Ile Tyr Thr Leu Ile Glu Glu Ser
625                 630                 635                 640

Gln Asn Gln Gln Glu Lys Asn Glu Gln Glu Leu Leu Glu Leu Asp Lys
                645                 650                 655

Trp Ala Ser Leu Trp Asn Trp Phe Asp Ile Thr Lys Trp Leu Trp Tyr
                660                 665                 670

Ile Lys Ile Phe Ile Met Ile Val Gly Gly Leu Val Gly Leu Arg Leu
            675                 680                 685

Val Phe Thr Val Leu Ser Ile Val Asn Arg Val Arg Gln Gly Tyr Ser
    690                 695                 700

Pro Leu Ser Phe Gln Thr Leu Leu Pro Ala Pro Arg Gly Pro Asp Arg
705                 710                 715                 720

Pro Glu Gly Ile Glu Glu Glu Gly Gly Glu Arg Asp Arg Asp Arg Ser
                725                 730                 735

Gly Arg Leu Val Asn Gly Phe Leu Ala Leu Ile Trp Val Asp Leu Arg
                740                 745                 750

Ser Leu Cys Leu Phe Ser Tyr His Arg Leu Arg Asp Leu Leu Leu Thr
            755                 760                 765

Val Thr Arg Ile Val Glu Leu Leu Gly Arg Arg Gly Trp Glu Val Leu
    770                 775                 780

Lys Tyr Trp Trp Asn Leu Leu Gln Tyr Trp Ser Gln Glu Leu Lys Asn
```

```
                785                 790                 795                 800
Ser Ala Val Ser Leu Leu Asn Ala Thr Ala Ile Ala Val Ala Glu Gly
                    805                 810                 815

Thr Asp Arg Ile Ile Glu Ala Leu Gln Arg Thr Tyr Arg Ala Ile Leu
                    820                 825                 830

His Ile Pro Thr Arg Ile Arg Gln Gly Leu Glu Arg Ala Leu Leu
                    835                 840                 845

<210> SEQ ID NO 2
<211> LENGTH: 856
<212> TYPE: PRT
<213> ORGANISM: Simian-Human immunodeficiency virus

<400> SEQUENCE: 2

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
            35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Asn Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Thr
                180                 185                 190

Leu Thr Ser Cys Asn Thr Ser Val Ile Ser Gln Ala Cys Pro Lys Val
            195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
                260                 265                 270

Arg Ser Val Asn Phe Met Asp Asn Ala Lys Thr Ile Ile Val Gln Leu
            275                 280                 285

Asn Thr Ser Val Glu Ile Asn Cys Thr Arg Pro Ser Asn Asn Thr Ile
    290                 295                 300

Lys Arg Ile Arg Ile Gln Arg Gly Pro Gly Arg Ala Phe Val Thr Met
305                 310                 315                 320
```

```
Gly Lys Ile Gly Asp Met Arg Gln Ala His Cys Asn Ile Ser Arg Ala
            325                 330                 335
Lys Trp Asn Asn Thr Leu Lys Gln Ile Ala Ser Lys Leu Arg Glu Gln
        340                 345                 350
Phe Gly Asn Asn Lys Thr Ile Ile Phe Lys Gln Ser Ser Gly Gly Asp
        355                 360                 365
Pro Glu Ile Val Thr His Ser Phe Asn Cys Gly Gly Glu Phe Phe Tyr
370                 375                 380
Cys Asn Ser Thr Gln Leu Phe Asn Ser Thr Trp Phe Asn Ser Thr Trp
385                 390                 395                 400
Ser Thr Glu Gly Ser Asn Asn Thr Glu Gly Ser Asp Thr Ile Thr Leu
                405                 410                 415
Pro Cys Arg Ile Lys Gln Ile Ile Asn Met Trp Gln Lys Val Gly Lys
            420                 425                 430
Ala Met Tyr Ala Pro Pro Ile Ser Gly Gln Ile Arg Cys Ser Ser Asn
        435                 440                 445
Ile Thr Gly Leu Leu Leu Thr Arg Asp Gly Gly Lys Gly Asn Asn Glu
    450                 455                 460
Ser Glu Ile Phe Arg Pro Gly Gly Gly Asp Met Arg Asp Asn Trp Arg
465                 470                 475                 480
Ser Glu Leu Tyr Lys Tyr Lys Val Val Lys Ile Glu Pro Leu Gly Val
                485                 490                 495
Ala Pro Thr Lys Ala Lys Arg Arg Val Gln Arg Glu Lys Arg Ala
            500                 505                 510
Val Gly Ile Gly Ala Leu Phe Leu Gly Phe Leu Gly Ala Ala Gly Ser
        515                 520                 525
Thr Met Gly Ala Ala Ser Met Thr Leu Thr Val Gln Ala Arg Gln Leu
    530                 535                 540
Leu Ser Gly Ile Val Gln Gln Gln Asn Asn Leu Leu Arg Ala Ile Glu
545                 550                 555                 560
Ala Gln Gln His Leu Leu Gln Leu Thr Val Trp Gly Ile Lys Gln Leu
                565                 570                 575
Gln Ala Arg Ile Leu Ala Val Glu Arg Tyr Leu Lys Asp Gln Gln Leu
            580                 585                 590
Leu Gly Ile Trp Gly Cys Ser Gly Lys Leu Ile Cys Thr Thr Ala Val
        595                 600                 605
Pro Trp Asn Ala Ser Trp Ser Asn Lys Ser Leu Glu Gln Ile Trp Asn
    610                 615                 620
His Met Thr Trp Met Glu Trp Asp Arg Glu Ile Asn Asn Tyr Thr Ser
625                 630                 635                 640
Leu Ile His Ser Leu Ile Glu Glu Ser Gln Asn Gln Gln Glu Lys Asn
                645                 650                 655
Glu Gln Glu Leu Leu Glu Leu Asp Lys Trp Ala Ser Leu Trp Asn Trp
            660                 665                 670
Phe Asp Ile Thr Asn Trp Leu Trp Tyr Ile Lys Leu Phe Ile Met Ile
        675                 680                 685
Val Gly Gly Leu Val Gly Leu Arg Ile Val Phe Ala Val Leu Ser Ile
    690                 695                 700
Val Asn Arg Val Arg Gln Gly Tyr Ser Pro Leu Ser Phe Gln Thr His
705                 710                 715                 720
Leu Pro Thr Pro Arg Gly Pro Asp Arg Pro Glu Gly Ile Glu Glu
                725                 730                 735
Gly Gly Glu Arg Asp Arg Asp Arg Ser Ile Arg Leu Val Asn Gly Ser
```

-continued

```
                        740                 745                 750
Leu Ala Leu Ile Trp Asp Asp Leu Arg Ser Leu Cys Leu Phe Ser Tyr
            755                 760                 765
His Arg Leu Arg Asp Leu Leu Ile Val Thr Arg Ile Val Glu Leu
        770                 775                 780
Leu Gly Arg Arg Gly Trp Glu Ala Leu Lys Tyr Trp Trp Asn Leu Leu
785                 790                 795                 800
Gln Tyr Trp Ser Gln Glu Leu Lys Asn Ser Ala Val Ser Leu Leu Asn
                805                 810                 815
Ala Thr Ala Ile Ala Val Ala Glu Gly Thr Asp Arg Val Ile Glu Val
            820                 825                 830
Val Gln Gly Ala Cys Arg Ala Ile Arg His Ile Pro Arg Arg Ile Arg
        835                 840                 845
Gln Gly Leu Glu Arg Ile Leu Leu
    850                 855

<210> SEQ ID NO 3
<211> LENGTH: 6
<212> TYPE: PRT
<213> ORGANISM: Artificial Sequence
<220> FEATURE:
<223> OTHER INFORMATION: Gly-Ser linker

<400> SEQUENCE: 3

Gly Gly Ser Gly Ser Gly
1               5

<210> SEQ ID NO 4
<211> LENGTH: 18
<212> TYPE: PRT
<213> ORGANISM: Artificial Sequence
<220> FEATURE:
<223> OTHER INFORMATION: Gly-Ser linker

<400> SEQUENCE: 4

Gly Ser Thr Ser Gly Ser Gly Lys Pro Gly Ser Gly Glu Gly Ser Thr
1               5                   10                  15

Lys Gly

<210> SEQ ID NO 5
<211> LENGTH: 7
<212> TYPE: PRT
<213> ORGANISM: Artificial Sequence
<220> FEATURE:
<223> OTHER INFORMATION: Gly-Ser linker

<400> SEQUENCE: 5

Ser Gly Arg Ala His Ala Gly
1               5

<210> SEQ ID NO 6
<211> LENGTH: 10
<212> TYPE: PRT
<213> ORGANISM: Artificial Sequence
<220> FEATURE:
<223> OTHER INFORMATION: Gly linker (Gly)n, where n=1 to 10
<220> FEATURE:
<221> NAME/KEY: Xaa
<222> LOCATION: (1)..(10)
<223> OTHER INFORMATION: Xaa is Gly or absent

<400> SEQUENCE: 6

Xaa Xaa Xaa Xaa Xaa Xaa Xaa Xaa Xaa Xaa
```

```
<210> SEQ ID NO 7
<211> LENGTH: 10
<212> TYPE: PRT
<213> ORGANISM: Artificial Sequence
<220> FEATURE:
<223> OTHER INFORMATION: Ser linker (Ser)n, where n=1 to 10
<220> FEATURE:
<221> NAME/KEY: Xaa
<222> LOCATION: (1)..(10)
<223> OTHER INFORMATION: Xaa is Ser or absent

<400> SEQUENCE: 7

Xaa Xaa Xaa Xaa Xaa Xaa Xaa Xaa Xaa Xaa
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Ala linker (Ala)n, where n=1 to 10
<220> FEATURE:
<221> NAME/KEY: Xaa
<222> LOCATION: (1)..(10)
<223> OTHER INFORMATION: Xaa is Ala or absent

<400> SEQUENCE: 8

Xaa Xaa Xaa Xaa Xaa Xaa Xaa Xaa Xaa Xaa
1               5                   10

<210> SEQ ID NO 9
<211> LENGTH: 2
<212> TYPE: PRT
<213> ORGANISM: Artificial Sequence
<220> FEATURE:
<223> OTHER INFORMATION: Gly-Ser linker (Gly-Ser)n, where n=1 to 10

<400> SEQUENCE: 9

Gly Ser
1

<210> SEQ ID NO 10
<211> LENGTH: 4
<212> TYPE: PRT
<213> ORGANISM: Artificial Sequence
<220> FEATURE:
<223> OTHER INFORMATION: Gly-Ser linker (Gly-Ser-Ser-Gly)n, where n=1 to
      10

<400> SEQUENCE: 10

Gly Ser Ser Gly
1

<210> SEQ ID NO 11
<211> LENGTH: 3
<212> TYPE: PRT
<213> ORGANISM: Artificial Sequence
<220> FEATURE:
<223> OTHER INFORMATION: Gly-Ser linker (Gly-Ser-Gly)n, where n=1 to 10

<400> SEQUENCE: 11

Gly Ser Gly
1

<210> SEQ ID NO 12
<211> LENGTH: 3
```

```
<212> TYPE: PRT
<213> ORGANISM: Artificial Sequence
<220> FEATURE:
<223> OTHER INFORMATION: Gly-Ser linker (Gly-Ser-Ser)n, where n=1 to 10

<400> SEQUENCE: 12

Gly Ser Ser
1

<210> SEQ ID NO 13
<211> LENGTH: 2
<212> TYPE: PRT
<213> ORGANISM: Artificial Sequence
<220> FEATURE:
<223> OTHER INFORMATION: Gly-Ala linker (Gly-Ala)n, where n=1 to 10

<400> SEQUENCE: 13

Gly Ala
1

<210> SEQ ID NO 14
<211> LENGTH: 68
<212> TYPE: PRT
<213> ORGANISM: Artificial Sequence
<220> FEATURE:
<223> OTHER INFORMATION: C4b multimerization domain

<400> SEQUENCE: 14

Ser Gly Arg Ala His Ala Gly Trp Glu Thr Pro Glu Gly Cys Glu Gln
1               5                   10                  15

Val Leu Thr Gly Lys Arg Leu Met Gln Cys Leu Pro Asn Pro Glu Asp
            20                  25                  30

Val Lys Met Ala Leu Glu Val Tyr Lys Leu Ser Leu Glu Ile Glu Gln
        35                  40                  45

Leu Glu Leu Gln Arg Asp Ser Ala Arg Gln Ser Thr Leu Asp Lys Glu
    50                  55                  60

Leu Val Pro Arg
65

<210> SEQ ID NO 15
<211> LENGTH: 55
<212> TYPE: PRT
<213> ORGANISM: Artificial Sequence
<220> FEATURE:
<223> OTHER INFORMATION: C4b multimerization domain

<400> SEQUENCE: 15

Lys Lys Gln Gly Asp Ala Asp Val Cys Gly Glu Val Ala Tyr Ile Gln
1               5                   10                  15

Ser Val Val Ser Asp Cys His Val Pro Thr Ala Glu Leu Arg Thr Leu
            20                  25                  30

Leu Glu Ile Arg Lys Leu Phe Leu Glu Ile Gln Lys Leu Lys Val Glu
        35                  40                  45

Leu Gln Gly Leu Ser Lys Glu
    50                  55

<210> SEQ ID NO 16
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 16
```

```
Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
                20                  25                  30

Lys Leu Ser Leu Glu Ile Glu Gln Leu Glu Leu Gln Arg Asp Ser Ala
            35                  40                  45

Arg Gln Ser Thr Leu Asp Lys Glu Leu
    50                  55

<210> SEQ ID NO 17
<211> LENGTH: 58
<212> TYPE: PRT
<213> ORGANISM: Artificial Sequence
<220> FEATURE:
<223> OTHER INFORMATION: C4b multimerization domain

<400> SEQUENCE: 17

Trp Glu Thr Pro Glu Gly Cys Glu Gln Val Leu Thr Gly Lys Arg Leu
1               5                   10                  15

Met Gln Cys Leu Pro Asn Pro Glu Asp Val Lys Met Ala Leu Glu Val
                20                  25                  30

Tyr Lys Leu Ser Leu Glu Ile Glu Gln Leu Glu Leu Gln Arg Asp Ser
            35                  40                  45

Ala Arg Gln Ser Thr Leu Asp Lys Glu Leu
    50                  55

<210> SEQ ID NO 18
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 18

Cys Glu Gln Val Leu Thr Gly Lys Arg Leu Met Gln Cys Leu Pro Asn
1               5                   10                  15

Pro Glu Asp Val Lys Met Ala Leu Glu Val Tyr Lys Leu Ser Leu Glu
                20                  25                  30

Ile Glu Gln Leu Glu Leu Gln Arg Asp Ser Ala Arg Gln Ser Thr Leu
            35                  40                  45

Asp Lys Glu Leu
    50

<210> SEQ ID NO 19
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 19

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
                20                  25                  30

Lys Leu Ser Leu Glu Ile Glu Gln Leu Glu Leu Gln Arg Asp Ser Ala
            35                  40                  45

Arg Gln Tyr Thr Leu Asp Lys Glu Leu
    50                  55
```

```
<210> SEQ ID NO 20
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 20

Glu Thr Pro Glu Gly Cys Glu Gln Val Leu Ala Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Arg Ala
        35                  40                  45

Arg Gln Ser Thr Leu Asp Lys Glu Leu
    50                  55

<210> SEQ ID NO 21
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 21

Glu Thr Pro Glu Gly Cys Glu Gln Val Leu Ala Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Arg Ala
        35                  40                  45

Arg Gln Ser Thr Trp Asp Lys Glu Leu
    50                  55

<210> SEQ ID NO 22
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 22

Glu Val Pro Glu Gly Cys Glu Gln Val Gln Ala Gly Arg Arg Leu Met
1               5                   10                  15

Gln Cys Leu Ala Asp Pro Tyr Glu Val Lys Met Ala Leu Glu Val Tyr
            20                  25                  30

Lys Leu Ser Leu Glu Ile Glu Leu Leu Glu Leu Gln Arg Asp Lys Ala
        35                  40                  45

Arg Lys Ser Ser Val Leu Arg Gln Leu
    50                  55

<210> SEQ ID NO 23
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 23

Val Val Pro Glu Gly Cys Glu His Ile Leu Lys Gly Arg Lys Thr Met
1               5                   10                  15
```

```
Gln Cys Leu Pro Asn Pro Glu Asp Val Lys Met Ala Leu Glu Ile Tyr
            20                  25                  30

Lys Leu Ser Leu Asp Ile Glu Leu Leu Glu Leu Gln Arg Asp Arg Ala
        35                  40                  45

Lys Glu Ser Thr Val Gln Ser Pro Val
    50                  55
```

<210> SEQ ID NO 24
<211> LENGTH: 55
<212> TYPE: PRT
<213> ORGANISM: Artificial Sequence
<220> FEATURE:
<223> OTHER INFORMATION: C4b multimerization domain

<400> SEQUENCE: 24

```
Glu Val Pro Lys Asp Cys Glu His Val Phe Ala Gly Lys Lys Leu Met
1               5                   10                  15

Gln Cys Leu Pro Asn Ser Asn Asp Val Lys Met Ala Leu Glu Val Tyr
            20                  25                  30

Lys Leu Thr Leu Glu Ile Lys Gln Leu Gln Leu Gln Ile Asp Lys Ala
        35                  40                  45

Lys His Val Asp Arg Glu Leu
    50              55
```

<210> SEQ ID NO 25
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 25

```
Glu Tyr Pro Glu Asp Cys Glu Gln Val His Glu Gly Lys Lys Leu Met
1               5                   10                  15

Gln Cys Leu Pro Asn Leu Glu Glu Ile Lys Leu Ala Leu Glu Leu Tyr
            20                  25                  30

Lys Leu Ser Leu Glu Thr Lys Leu Leu Glu Leu Gln Ile Asp Lys Glu
        35                  40                  45

Lys Lys Ala Lys Ala Lys Tyr Ser Ile
    50                  55
```

<210> SEQ ID NO 26
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 26

```
Glu Tyr Pro Glu Asp Cys Glu Gln Val His Glu Gly Lys Lys Leu Met
1               5                   10                  15

Glu Cys Leu Pro Thr Leu Glu Glu Ile Lys Leu Ala Leu Ala Leu Tyr
            20                  25                  30

Lys Leu Ser Leu Glu Thr Asn Leu Leu Glu Leu Gln Ile Asp Lys Glu
        35                  40                  45

Lys Lys Ala Lys Ala Lys Tyr Ser Thr
    50                  55
```

<210> SEQ ID NO 27
<211> LENGTH: 57
<212> TYPE: PRT

<213> ORGANISM: Artificial Sequence
<220> FEATURE:
<223> OTHER INFORMATION: C4b multimerization domain

<400> SEQUENCE: 27

Glu Ile Ala Glu Gly Cys Glu Gln Val Leu Ala Gly Arg Lys Ile Met
1               5                   10                  15

Gln Cys Leu Pro Lys Pro Glu Asp Val Arg Thr Ala Leu Glu Leu Tyr
                20                  25                  30

Lys Leu Ser Leu Glu Ile Lys Gln Leu Glu Lys Lys Leu Glu Lys Glu
            35                  40                  45

Glu Lys Cys Thr Pro Glu Val Gln Glu
    50                  55

<210> SEQ ID NO 28
<211> LENGTH: 67
<212> TYPE: PRT
<213> ORGANISM: Artificial Sequence
<220> FEATURE:
<223> OTHER INFORMATION: C4b multimerization domain

<400> SEQUENCE: 28

Glu Tyr Pro Glu Gly Cys Glu Gln Val Val Thr Gly Arg Lys Leu Leu
1               5                   10                  15

Gln Cys Leu Ser Arg Pro Glu Glu Val Lys Leu Ala Leu Glu Val Tyr
                20                  25                  30

Lys Leu Ser Leu Glu Ile Glu Ile Leu Gln Thr Asn Lys Leu Lys Lys
            35                  40                  45

Glu Ala Phe Leu Leu Arg Glu Arg Glu Lys Asn Val Thr Cys Asp Phe
    50                  55                  60

Asn Pro Glu
65

<210> SEQ ID NO 29
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 29

Glu Tyr Pro Glu Gly Cys Glu Gln Val Val Thr Gly Arg Lys Leu Leu
1               5                   10                  15

Lys Cys Leu Ser Arg Pro Glu Glu Val Lys Leu Ala Leu Glu Val Tyr
                20                  25                  30

Lys Leu Ser Leu Glu Ile Ala Leu Leu Glu Leu Gln Ile Asp Lys Pro
            35                  40                  45

Lys Asp Ala Ser
    50

<210> SEQ ID NO 30
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 30

Glu Val Pro Glu Asn Cys Glu Gln Val Ile Val Gly Lys Lys Leu Met
1               5                   10                  15

Lys Cys Leu Ser Asn Pro Asp Glu Ala Gln Met Ala Leu Gln Leu Tyr

```
                    20                  25                  30

Lys Leu Ser Leu Glu Ala Glu Leu Leu Arg Leu Gln Ile Val Lys Ala
            35                  40                  45

Arg Gln Gly Ser
    50

<210> SEQ ID NO 31
<211> LENGTH: 54
<212> TYPE: PRT
<213> ORGANISM: Artificial Sequence
<220> FEATURE:
<223> OTHER INFORMATION: C4b multimerization domain

<400> SEQUENCE: 31

Glu Ala Ser Glu Asp Leu Lys Pro Ala Leu Thr Gly Asn Lys Thr Met
1               5                   10                  15

Gln Tyr Val Pro Asn Ser His Asp Val Lys Met Ala Leu Glu Ile Tyr
            20                  25                  30

Lys Leu Thr Leu Glu Val Glu Leu Leu Gln Leu Gln Ile Gln Lys Glu
        35                  40                  45

Lys His Thr Glu Ala His
    50

<210> SEQ ID NO 32
<211> LENGTH: 51
<212> TYPE: PRT
<213> ORGANISM: Artificial Sequence
<220> FEATURE:
<223> OTHER INFORMATION: C4b multimerization domain

<400> SEQUENCE: 32

Val Ser Ala Glu Val Cys Glu Ala Val Phe Lys Gly Gln Lys Leu Leu
1               5                   10                  15

Lys Cys Leu Pro Asn Ala Met Glu Val Lys Met Ala Leu Glu Val Tyr
            20                  25                  30

Lys Leu Ser Leu Glu Ile Glu Lys Leu Glu Gln Glu Lys Arg Lys Leu
        35                  40                  45

Glu Ile Ala
    50

<210> SEQ ID NO 33
<211> LENGTH: 66
<212> TYPE: PRT
<213> ORGANISM: Artificial Sequence
<220> FEATURE:
<223> OTHER INFORMATION: C4b multimerization domain

<400> SEQUENCE: 33

Glu Val Pro Glu Glu Cys Lys Gln Val Ala Ala Gly Arg Lys Leu Leu
1               5                   10                  15

Glu Cys Leu Pro Asn Pro Ser Asp Val Lys Met Ala Leu Glu Val Tyr
            20                  25                  30

Lys Leu Ser Leu Glu Ile Glu Gln Leu Glu Lys Glu Lys Tyr Val Lys
        35                  40                  45

Ile Gln Glu Lys Phe Ser Lys Lys Glu Met Lys Gln Leu Thr Ser Ala
    50                  55                  60

Leu His
65

<210> SEQ ID NO 34
```

<211> LENGTH: 59
<212> TYPE: PRT
<213> ORGANISM: Artificial Sequence
<220> FEATURE:
<223> OTHER INFORMATION: C4b multimerization domain

<400> SEQUENCE: 34

Glu Val Leu Glu Asp Cys Arg Ile Val Ser Arg Gly Ala Gln Leu Leu
1               5                   10                  15

His Cys Leu Ser Ser Pro Glu Asp Val His Arg Ala Leu Lys Val Tyr
            20                  25                  30

Lys Leu Phe Leu Glu Ile Glu Arg Leu Glu His Gln Lys Glu Lys Trp
        35                  40                  45

Ile Gln Leu His Arg Lys Pro Gln Ser Met Lys
    50                  55

<210> SEQ ID NO 35
<211> LENGTH: 63
<212> TYPE: PRT
<213> ORGANISM: Artificial Sequence
<220> FEATURE:
<223> OTHER INFORMATION: C4b multimerization domain

<400> SEQUENCE: 35

Glu Gly Pro Glu Asp Cys Glu Ile Val Asn Lys Gly Arg Gln Leu Leu
1               5                   10                  15

Gln Cys Leu Ser Ser Pro Glu Asp Val Gln Arg Ala Leu Glu Val Tyr
            20                  25                  30

Lys Leu Ser Leu Glu Ile Glu Arg Leu Glu Gln Gln Arg Glu Lys Arg
        35                  40                  45

Thr Ser Val His Arg Lys Ala His Tyr Thr Lys Val Asp Gly Pro
    50                  55                  60

<210> SEQ ID NO 36
<211> LENGTH: 67
<212> TYPE: PRT
<213> ORGANISM: Artificial Sequence
<220> FEATURE:
<223> OTHER INFORMATION: C4b multimerization domain

<400> SEQUENCE: 36

Glu Ala Pro Glu Gly Cys Glu Gln Val Leu Thr Gly Arg Lys Leu Met
1               5                   10                  15

Gln Cys Leu Pro Ser Pro Glu Asp Val Lys Val Ala Leu Glu Val Tyr
            20                  25                  30

Lys Leu Ser Leu Glu Ile Lys Gln Leu Glu Lys Glu Arg Asp Lys Leu
        35                  40                  45

Met Asn Thr His Gln Lys Phe Ser Glu Lys Glu Met Lys Asp Leu
    50                  55                  60

Phe Phe Pro
65

<210> SEQ ID NO 37
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 37

Glu Val Pro Glu Gly Cys Glu Gln Val Leu Thr Gly Lys Lys Leu Met
1               5                   10                  15

```
Gln Cys Leu Pro Asn Pro Glu Asp Val Lys Met Ala Leu Glu Val Tyr
            20                  25                  30

Lys Leu Ser Leu Glu Ile Glu Leu Glu Leu Gln Ile Asp Lys Ala
        35                  40                  45

Arg Gln Gly Ser
    50

<210> SEQ ID NO 38
<211> LENGTH: 47
<212> TYPE: PRT
<213> ORGANISM: Artificial Sequence
<220> FEATURE:
<223> OTHER INFORMATION: C4b multimerization domain

<400> SEQUENCE: 38

Gly Cys Glu Gln Val Leu Thr Gly Lys Arg Leu Met Gln Cys Leu Pro
1               5                   10                  15

Asn Pro Glu Asp Val Lys Met Ala Leu Glu Val Tyr Lys Leu Ser Leu
            20                  25                  30

Glu Ile Glu Gln Leu Glu Leu Gln Arg Asp Ser Ala Arg Gln Ser
        35                  40                  45

<210> SEQ ID NO 39
<211> LENGTH: 51
<212> TYPE: PRT
<213> ORGANISM: Artificial Sequence
<220> FEATURE:
<223> OTHER INFORMATION: C4b multimerization domain

<400> SEQUENCE: 39

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Glu Gln Leu Glu Leu Gln Arg Asp Ser Ala
        35                  40                  45

Arg Gln Ser
    50

<210> SEQ ID NO 40
<211> LENGTH: 53
<212> TYPE: PRT
<213> ORGANISM: Artificial Sequence
<220> FEATURE:
<223> OTHER INFORMATION: C4b multimerization domain

<400> SEQUENCE: 40

Gly Ser Glu Gln Val Leu Thr Gly Lys Arg Leu Met Gln Ser Leu Pro
1               5                   10                  15

Asn Pro Glu Asp Val Lys Met Ala Leu Glu Val Tyr Lys Leu Ser Leu
            20                  25                  30

Glu Ile Glu Gln Leu Glu Leu Gln Arg Asp Ser Ala Arg Gln Ser Thr
        35                  40                  45

Leu Asp Lys Glu Leu
    50

<210> SEQ ID NO 41
<211> LENGTH: 57
<212> TYPE: PRT
<213> ORGANISM: Artificial Sequence
<220> FEATURE:
```

<223> OTHER INFORMATION: C4b multimerization domain

<400> SEQUENCE: 41

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Ile Tyr
            20                  25                  30

Lys Leu Thr Leu Glu Ile Glu Gln Leu Glu Leu Gln Arg Asp Ser Ala
        35                  40                  45

Arg Gln Ser Thr Leu Asp Lys Glu Leu
    50                  55

<210> SEQ ID NO 42
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 42

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Ile Tyr
            20                  25                  30

Lys Leu Ser Leu Glu Ile Lys Gln Leu Glu Leu Gln Arg Asp Ser Ala
        35                  40                  45

Arg Gln Ser Thr Leu Asp Lys Glu Leu
    50                  55

<210> SEQ ID NO 43
<211> LENGTH: 50
<212> TYPE: PRT
<213> ORGANISM: Artificial Sequence
<220> FEATURE:
<223> OTHER INFORMATION: C4b multimerization domain

<400> SEQUENCE: 43

Glu Gly Cys Glu Gln Ile Leu Thr Gly Lys Arg Leu Met Gln Cys Leu
1               5                   10                  15

Pro Asp Pro Glu Asp Val Lys Met Ala Leu Glu Ile Tyr Lys Leu Ser
            20                  25                  30

Leu Glu Ile Lys Gln Leu Glu Leu Gln Arg Asp Arg Ala Arg Gln Ser
        35                  40                  45

Thr Leu
    50

<210> SEQ ID NO 44
<211> LENGTH: 57
<212> TYPE: PRT
<213> ORGANISM: Artificial Sequence
<220> FEATURE:
<223> OTHER INFORMATION: C4b multimerization domain

<400> SEQUENCE: 44

Glu Thr Pro Glu Gly Cys Glu Gln Val Leu Thr Gly Lys Arg Leu Met
1               5                   10                  15

Gln Cys Leu Pro Asn Pro Glu Asp Val Lys Met Ala Leu Glu Val Tyr
            20                  25                  30

Lys Leu Ser Leu Glu Ile Lys Gln Leu Glu Leu Gln Arg Asp Arg Ala
        35                  40                  45

```
Arg Gln Ser Thr Leu Asp Lys Glu Leu
    50                  55
```

<210> SEQ ID NO 45
<211> LENGTH: 52
<212> TYPE: PRT
<213> ORGANISM: Artificial Sequence
<220> FEATURE:
<223> OTHER INFORMATION: C4b multimerization domain

<400> SEQUENCE: 45

```
Glu Gly Cys Glu Gln Ile Leu Thr Gly Lys Arg Leu Met Gln Cys Leu
1               5                   10                  15

Pro Asn Pro Glu Asp Val Lys Met Ala Leu Glu Ile Tyr Lys Leu Ser
            20                  25                  30

Leu Glu Ile Glu Gln Leu Glu Leu Gln Arg Asp Arg Ala Arg Gln Ser
        35                  40                  45

Thr Leu Asp Lys
    50
```

<210> SEQ ID NO 46
<211> LENGTH: 61
<212> TYPE: PRT
<213> ORGANISM: Homo sapiens

<400> SEQUENCE: 46

```
Trp Glu Thr Pro Glu Gly Cys Glu Gln Val Leu Thr Gly Lys Arg Leu
1               5                   10                  15

Met Gln Cys Leu Pro Asn Pro Glu Asp Val Lys Met Ala Leu Glu Val
            20                  25                  30

Tyr Lys Leu Ser Leu Glu Ile Glu Gln Leu Glu Leu Gln Arg Asp Ser
        35                  40                  45

Ala Arg Gln Ser Thr Leu Asp Lys Glu Leu Val Pro Arg
    50                  55                  60
```

<210> SEQ ID NO 47
<211> LENGTH: 62
<212> TYPE: PRT
<213> ORGANISM: Homo sapiens

<400> SEQUENCE: 47

```
Ala His Ala Gly Trp Glu Thr Pro Glu Gly Cys Glu Gln Val Leu Thr
1               5                   10                  15

Gly Lys Arg Leu Met Gln Cys Leu Pro Asn Pro Glu Asp Val Lys Met
            20                  25                  30

Ala Leu Glu Val Tyr Lys Leu Ser Leu Glu Ile Glu Gln Leu Glu Leu
        35                  40                  45

Gln Arg Asp Ser Ala Arg Gln Ser Thr Leu Asp Lys Glu Leu
    50                  55                  60
```

<210> SEQ ID NO 48
<211> LENGTH: 56
<212> TYPE: PRT
<213> ORGANISM: Gallus gallus

<400> SEQUENCE: 48

```
Ser Lys Lys Gln Gly Asp Ala Asp Val Cys Gly Glu Val Ala Tyr Ile
1               5                   10                  15

Gln Ser Val Val Ser Asp Cys His Val Pro Thr Glu Asp Val Lys Thr
            20                  25                  30
```

```
Leu Leu Glu Ile Arg Lys Leu Phe Leu Glu Ile Gln Lys Leu Lys Val
        35                  40                  45

Glu Leu Gln Gly Leu Ser Lys Glu
    50                  55
```

<210> SEQ ID NO 49
<211> LENGTH: 56
<212> TYPE: PRT
<213> ORGANISM: Artificial Sequence
<220> FEATURE:
<223> OTHER INFORMATION: Heptamerization domain

<400> SEQUENCE: 49

```
Ser Lys Lys Gln Gly Asp Ala Asp Val Cys Gly Glu Val Ala Tyr Ile
1               5                   10                  15

Gln Ser Val Val Ser Asp Cys His Val Pro Thr Ala Glu Leu Arg Thr
            20                  25                  30

Leu Leu Glu Ile Arg Lys Leu Phe Leu Glu Ile Gln Lys Leu Lys Val
        35                  40                  45

Glu Leu Gln Gly Leu Ser Lys Glu
    50                  55
```

<210> SEQ ID NO 50
<211> LENGTH: 415
<212> TYPE: PRT
<213> ORGANISM: Artificial Sequence
<220> FEATURE:
<223> OTHER INFORMATION: e/m Env

<400> SEQUENCE: 50

```
Val Trp Lys Glu Ala Lys Thr Thr Leu Phe Cys Ala Ser Asp Ala Lys
1               5                   10                  15

Ala Tyr Glu Lys Glu Cys His Asn Val Trp Ala Thr His Ala Cys Val
            20                  25                  30

Pro Thr Asp Pro Asn Pro Gln Glu Val Val Leu Glu Asn Val Thr Glu
        35                  40                  45

Asn Phe Asn Met Trp Lys Asn Asp Met Val Asp Gln Met Gln Glu Asp
    50                  55                  60

Val Ile Ser Ile Trp Asp Gln Cys Leu Lys Pro Cys Val Lys Leu Thr
65                  70                  75                  80

Asn Thr Ser Thr Leu Thr Gln Ala Cys Pro Lys Val Thr Phe Asp Pro
            85                  90                  95

Ile Pro Ile His Tyr Cys Ala Pro Ala Gly Tyr Ala Ile Leu Lys Cys
        100                 105                 110

Asn Asn Lys Thr Phe Asn Gly Lys Gly Pro Cys Asn Asn Val Ser Thr
    115                 120                 125

Val Gln Cys Thr His Gly Ile Lys Pro Val Val Ser Thr Gln Leu Leu
130                 135                 140

Leu Asn Gly Ser Leu Ala Glu Glu Glu Ile Val Ile Arg Ser Lys Asn
145                 150                 155                 160

Leu Arg Asp Asn Ala Lys Ile Ile Ile Val Gln Leu Asn Lys Ser Val
                165                 170                 175

Glu Ile Val Cys Thr Arg Pro Asn Asn Gly Ser Gly Ser Gly Gly
            180                 185                 190

Asp Ile Arg Gln Ala Tyr Cys Asn Ile Ser Gly Arg Asn Trp Ser Glu
        195                 200                 205

Ala Val Asn Gln Val Lys Lys Lys Leu Lys Glu His Phe Pro His Lys
    210                 215                 220
```

```
Asn Ile Ser Phe Gln Ser Ser Gly Gly Asp Leu Glu Ile Thr Thr
225                 230                 235                 240

His Ser Phe Asn Cys Gly Gly Glu Phe Phe Tyr Cys Asn Thr Ser Gly
            245                 250                 255

Leu Phe Asn Asp Thr Ile Ser Asn Ala Thr Ile Met Leu Pro Cys Arg
        260                 265                 270

Ile Lys Gln Ile Ile Asn Met Trp Gln Glu Val Gly Lys Ala Ile Tyr
    275                 280                 285

Ala Pro Pro Ile Lys Gly Asn Ile Thr Cys Lys Ser Asp Ile Thr Gly
290                 295                 300

Leu Leu Leu Leu Arg Asp Gly Gly Asp Thr Thr Asp Asn Thr Glu Ile
305                 310                 315                 320

Phe Arg Pro Ser Gly Gly Asp Met Arg Asp Asn Trp Arg Ser Glu Leu
                325                 330                 335

Tyr Lys Tyr Lys Val Val Glu Ile Lys Pro Leu Ser Gly Arg Ala His
            340                 345                 350

Ala Gly Trp Glu Thr Pro Glu Gly Cys Glu Gln Val Leu Thr Gly Lys
        355                 360                 365

Arg Leu Met Gln Cys Leu Pro Asn Pro Glu Asp Val Lys Met Ala Leu
    370                 375                 380

Glu Val Tyr Lys Leu Ser Leu Glu Ile Glu Gln Leu Glu Leu Gln Arg
385                 390                 395                 400

Asp Ser Ala Arg Gln Ser Thr Leu Asp Lys Glu Leu Val Pro Arg
                405                 410                 415

<210> SEQ ID NO 51
<211> LENGTH: 528
<212> TYPE: PRT
<213> ORGANISM: Artificial Sequence
<220> FEATURE:
<223> OTHER INFORMATION: Ferritin fusion sequence

<400> SEQUENCE: 51

Val Trp Lys Glu Ala Lys Thr Thr Leu Phe Cys Ala Ser Asp Ala Lys
1               5                   10                  15

Ala Tyr Glu Lys Glu Cys His Asn Val Trp Ala Thr His Ala Cys Val
            20                  25                  30

Pro Thr Asp Pro Asn Pro Gln Glu Val Val Leu Glu Asn Val Thr Glu
        35                  40                  45

Asn Phe Asn Met Trp Lys Asn Asp Met Val Asp Gln Met Gln Glu Asp
    50                  55                  60

Val Ile Ser Ile Trp Asp Gln Cys Leu Lys Pro Cys Val Lys Leu Thr
65                  70                  75                  80

Asn Thr Ser Thr Leu Thr Gln Ala Cys Pro Lys Val Thr Phe Asp Pro
                85                  90                  95

Ile Pro Ile His Tyr Cys Ala Pro Ala Gly Tyr Ala Ile Leu Lys Cys
            100                 105                 110

Asn Asn Lys Thr Phe Asn Gly Lys Gly Pro Cys Asn Asn Val Ser Thr
        115                 120                 125

Val Gln Cys Thr His Gly Ile Lys Pro Val Val Ser Thr Gln Leu Leu
    130                 135                 140

Leu Asn Gly Ser Leu Ala Glu Glu Ile Val Ile Arg Ser Lys Asn
145                 150                 155                 160

Leu Arg Asp Asn Ala Lys Ile Ile Ile Val Gln Leu Asn Lys Ser Val
                165                 170                 175
```

Glu Ile Val Cys Thr Arg Pro Asn Asn Gly Ser Gly Ser Gly Gly
            180                 185                 190

Asp Ile Arg Gln Ala Tyr Cys Asn Ile Ser Gly Arg Asn Trp Ser Glu
            195                 200                 205

Ala Val Asn Gln Val Lys Lys Lys Leu Lys Glu His Phe Pro His Lys
210                 215                 220

Asn Ile Ser Phe Gln Ser Ser Ser Gly Gly Asp Leu Glu Ile Thr Thr
225                 230                 235                 240

His Ser Phe Asn Cys Gly Gly Glu Phe Phe Tyr Cys Asn Thr Ser Gly
                245                 250                 255

Leu Phe Asn Asp Thr Ile Ser Asn Ala Thr Ile Met Leu Pro Cys Arg
            260                 265                 270

Ile Lys Gln Ile Ile Asn Met Trp Gln Glu Val Gly Lys Ala Ile Tyr
            275                 280                 285

Ala Pro Pro Ile Lys Gly Asn Ile Thr Cys Lys Ser Asp Ile Thr Gly
            290                 295                 300

Leu Leu Leu Leu Arg Asp Gly Gly Asp Thr Thr Asp Asn Thr Glu Ile
305                 310                 315                 320

Phe Arg Pro Ser Gly Gly Asp Met Arg Asp Asn Trp Arg Ser Glu Leu
                325                 330                 335

Tyr Lys Tyr Lys Val Val Glu Ile Lys Pro Leu Gly Ser Gly Gly Ser
            340                 345                 350

Gly Glu Ser Gln Val Arg Gln Gln Phe Ser Lys Asp Ile Glu Lys Leu
            355                 360                 365

Leu Asn Glu Gln Val Asn Lys Glu Met Gln Ser Ser Asn Leu Tyr Met
370                 375                 380

Ser Met Ser Ser Trp Cys Tyr Thr His Ser Leu Asp Gly Ala Gly Leu
385                 390                 395                 400

Phe Leu Phe Asp His Ala Ala Glu Glu Tyr Glu His Ala Lys Lys Leu
                405                 410                 415

Ile Ile Phe Leu Asn Glu Asn Asn Val Pro Val Gln Leu Thr Ser Ile
            420                 425                 430

Ser Ala Pro Glu His Lys Phe Glu Gly Leu Thr Gln Ile Phe Gln Lys
            435                 440                 445

Ala Tyr Glu His Glu Gln His Ile Ser Glu Ser Ile Asn Asn Ile Val
            450                 455                 460

Asp His Ala Ile Lys Ser Lys Asp His Ala Thr Phe Asn Phe Leu Gln
465                 470                 475                 480

Trp Tyr Val Ala Glu Gln His Glu Glu Val Leu Phe Lys Asp Ile
                485                 490                 495

Leu Asp Lys Ile Glu Leu Ile Gly Asn Glu Asn His Gly Leu Tyr Leu
            500                 505                 510

Ala Asp Gln Tyr Val Lys Gly Ile Ala Lys Ser Arg Lys Ser Gly Ser
            515                 520                 525

<210> SEQ ID NO 52
<211> LENGTH: 347
<212> TYPE: PRT
<213> ORGANISM: Artificial Sequence
<220> FEATURE:
<223> OTHER INFORMATION: Engineered Env

<400> SEQUENCE: 52

Val Trp Lys Glu Ala Lys Thr Thr Leu Phe Cys Ala Ser Asp Ala Lys
1               5                   10                  15

```
Ala Tyr Glu Lys Glu Cys His Asn Val Trp Ala Thr His Ala Cys Val
         20                  25                  30

Pro Thr Asp Pro Asn Pro Gln Glu Val Val Leu Glu Asn Val Thr Glu
         35                  40                  45

Asn Phe Asn Met Trp Lys Asn Asp Met Val Asp Gln Met Gln Glu Asp
 50                  55                  60

Val Ile Ser Ile Trp Asp Gln Cys Leu Lys Pro Cys Val Lys Leu Thr
 65                  70                  75                  80

Asn Thr Ser Thr Leu Thr Gln Ala Cys Pro Lys Val Thr Phe Asp Pro
                 85                  90                  95

Ile Pro Ile His Tyr Cys Ala Pro Ala Gly Tyr Ala Ile Leu Lys Cys
            100                 105                 110

Asn Asn Lys Thr Phe Asn Gly Lys Gly Pro Cys Asn Asn Val Ser Thr
            115                 120                 125

Val Gln Cys Thr His Gly Ile Lys Pro Val Val Ser Thr Gln Leu Leu
130                 135                 140

Leu Asn Gly Ser Leu Ala Glu Glu Glu Ile Val Ile Arg Ser Lys Asn
145                 150                 155                 160

Leu Arg Asp Asn Ala Lys Ile Ile Ile Val Gln Leu Asn Lys Ser Val
                165                 170                 175

Glu Ile Val Cys Thr Arg Pro Asn Asn Gly Ser Gly Ser Gly Gly
            180                 185                 190

Asp Ile Arg Gln Ala Tyr Cys Asn Ile Ser Gly Arg Asn Trp Ser Glu
            195                 200                 205

Ala Val Asn Gln Val Lys Lys Lys Leu Lys Glu His Phe Pro His Lys
210                 215                 220

Asn Ile Ser Phe Gln Ser Ser Gly Gly Asp Leu Glu Ile Thr Thr
225                 230                 235                 240

His Ser Phe Asn Cys Gly Gly Glu Phe Phe Tyr Cys Asn Thr Ser Gly
                245                 250                 255

Leu Phe Asn Asp Thr Ile Ser Asn Ala Thr Ile Met Leu Pro Cys Arg
            260                 265                 270

Ile Lys Gln Ile Ile Asn Met Trp Gln Glu Val Gly Lys Ala Ile Tyr
            275                 280                 285

Ala Pro Pro Ile Lys Gly Asn Ile Thr Cys Lys Ser Asp Ile Thr Gly
290                 295                 300

Leu Leu Leu Leu Arg Asp Gly Gly Asp Thr Thr Asp Asn Thr Glu Ile
305                 310                 315                 320

Phe Arg Pro Ser Gly Gly Asp Met Arg Asp Asn Trp Arg Ser Glu Leu
                325                 330                 335

Tyr Lys Tyr Lys Val Val Glu Ile Lys Pro Leu
            340                 345
```

<210> SEQ ID NO 53
<211> LENGTH: 183
<212> TYPE: PRT
<213> ORGANISM: Artificial Sequence
<220> FEATURE:
<223> OTHER INFORMATION: Engineered Env

<400> SEQUENCE: 53

```
Arg Pro Val Val Ser Thr Gln Leu Leu Leu Asn Gly Ser Leu Ala Glu
1               5                   10                  15

Glu Glu Val Val Ile Arg Ser Val Asn Phe Thr Asp Asn Ala Lys Thr
            20                  25                  30
```

```
Ile Ile Val Gln Leu Asn Thr Ser Val Glu Ile Asn Cys Thr Gly Ala
         35                  40                  45

Gly His Cys Asn Ile Ser Arg Ala Lys Trp Asn Asn Thr Leu Lys Gln
 50                  55                  60

Ile Ala Ser Lys Leu Arg Glu Gln Phe Gly Asn Asn Lys Thr Ile Ile
 65                  70                  75                  80

Phe Lys Gln Ser Ser Gly Gly Asp Pro Glu Ile Val Thr His Ser Phe
                 85                  90                  95

Asn Cys Gly Gly Glu Phe Phe Tyr Cys Asp Ser Thr Gln Leu Phe Asn
                100                 105                 110

Ser Thr Trp Phe Asn Ser Thr Trp Ser Thr Glu Gly Ser Asn Asn Thr
                115                 120                 125

Glu Gly Ser Asp Thr Ile Thr Leu Pro Cys Arg Pro Ala Pro Pro Pro
        130                 135                 140

His Cys Ser Ser Asn Ile Thr Gly Leu Leu Leu Thr Arg Asp Gly Gly
145                 150                 155                 160

Asn Ser Asn Asn Glu Ser Glu Ile Phe Arg Pro Gly Gly Gly Asp Met
                165                 170                 175

Arg Asp Asn Trp Arg Ser Glu
        180

<210> SEQ ID NO 54
<211> LENGTH: 183
<212> TYPE: PRT
<213> ORGANISM: Artificial Sequence
<220> FEATURE:
<223> OTHER INFORMATION: Engineered Env

<400> SEQUENCE: 54

Arg Pro Val Val Ser Thr Gln Leu Leu Leu Asn Gly Ser Leu Ala Glu
1               5                   10                  15

Glu Glu Val Val Ile Arg Ser Val Asn Phe Thr Asp Asn Ala Lys Thr
                 20                  25                  30

Ile Ile Val Gln Leu Asn Thr Ser Val Glu Ile Asn Cys Thr Gly Ala
         35                  40                  45

Gly His Cys Asn Ile Ser Arg Ala Lys Trp Asn Asn Thr Leu Lys Gln
 50                  55                  60

Ile Ala Ser Lys Leu Arg Glu Gln Phe Gly Asn Asn Lys Thr Ile Ile
 65                  70                  75                  80

Phe Lys Gln Ser Ser Gly Gly Asp Pro Glu Ile Val Thr His Ser Phe
                 85                  90                  95

Asn Cys Gly Gly Glu Phe Phe Tyr Cys Asn Ser Thr Gln Leu Phe Asn
                100                 105                 110

Ser Thr Trp Phe Asn Ser Thr Trp Ser Thr Glu Gly Ser Asn Asn Thr
                115                 120                 125

Glu Gly Ser Asp Thr Ile Thr Leu Pro Cys Arg Pro Ala Pro Pro Pro
        130                 135                 140

His Cys Ser Ser Asn Ile Thr Gly Leu Leu Leu Thr Arg Asp Gly Gly
145                 150                 155                 160

Asn Ser Asn Asn Glu Ser Glu Ile Phe Arg Pro Gly Gly Gly Asp Met
                165                 170                 175

Arg Asp Asn Trp Arg Ser Glu
        180

<210> SEQ ID NO 55
```

```
<211> LENGTH: 175
<212> TYPE: PRT
<213> ORGANISM: Artificial Sequence
<220> FEATURE:
<223> OTHER INFORMATION: Engineered Env

<400> SEQUENCE: 55

Asp Thr Ile Thr Leu Pro Cys Arg Pro Ala Pro Pro His Cys Ser
1               5                  10                  15

Ser Asn Ile Thr Gly Leu Leu Leu Thr Arg Asp Gly Gly Asn Ser Asn
            20                  25                  30

Asn Glu Ser Glu Ile Phe Arg Pro Gly Gly Gly Asp Met Arg Asp Asn
        35                  40                  45

Trp Arg Ser Gly Leu Ser Gly Pro Val Val Ser Thr Gln Leu Leu
    50                  55                  60

Asn Gly Ser Leu Ala Glu Glu Val Val Ile Arg Ser Val Asn Phe
65                  70                  75                  80

Thr Asp Asn Ala Lys Thr Ile Ile Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asp
145                 150                 155                 160

Ser Thr Gln Leu Phe Asn Ser Thr Trp Phe Asn Ser Thr Trp Ser
                165                 170                 175

<210> SEQ ID NO 56
<211> LENGTH: 185
<212> TYPE: PRT
<213> ORGANISM: Artificial Sequence
<220> FEATURE:
<223> OTHER INFORMATION: Engineered Env

<400> SEQUENCE: 56

Gly Glu Phe Phe Tyr Cys Asp Ser Thr Gln Leu Phe Asn Ser Thr Trp
1               5                  10                  15

Phe Asn Ser Thr Trp Ser Thr Glu Gly Ser Asn Asn Thr Glu Gly Ser
            20                  25                  30

Asp Thr Ile Thr Leu Pro Cys Arg Pro Ala Pro Pro His Cys Ser
        35                  40                  45

Ser Asn Ile Thr Gly Leu Leu Leu Thr Arg Asp Gly Gly Asn Ser Asn
    50                  55                  60

Asn Glu Ser Glu Ile Phe Arg Pro Gly Gly Gly Asp Met Arg Asp Asn
65                  70                  75                  80

Trp Arg Ser Gly Leu Ser Gly Pro Val Val Ser Thr Gln Leu Leu
                85                  90                  95

Asn Gly Ser Leu Ala Glu Glu Val Val Ile Arg Ser Val Asn Phe
            100                 105                 110

Thr Asp Asn Ala Lys Thr Ile Ile Val Gln Leu Asn Thr Ser Val Glu
        115                 120                 125

Ile Asn Cys Thr Gly Ala Gly His Cys Asn Ile Ser Arg Ala Lys Trp
    130                 135                 140

Asn Asn Thr Leu Lys Gln Ile Ala Ser Lys Leu Arg Glu Gln Phe Gly
```

```
Asn Asn Lys Thr Ile Ile Phe Lys Gln Ser Ser Gly Gly Asp Pro Glu
            165                 170                 175

Ile Val Thr His Ser Phe Asn Cys Gly
            180                 185

<210> SEQ ID NO 57
<211> LENGTH: 175
<212> TYPE: PRT
<213> ORGANISM: Artificial Sequence
<220> FEATURE:
<223> OTHER INFORMATION: Engineered Env

<400> SEQUENCE: 57

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asp
145                 150                 155                 160

Ser Thr Gln Leu Phe Asn Ser Thr Trp Phe Asn Ser Thr Trp Ser
                165                 170                 175

<210> SEQ ID NO 58
<211> LENGTH: 175
<212> TYPE: PRT
<213> ORGANISM: Artificial Sequence
<220> FEATURE:
<223> OTHER INFORMATION: Engineered Env

<400> SEQUENCE: 58

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Cys Arg Ser Val Asn Phe
65                  70                  75                  80

Thr Asp Asn Ala Lys Ser Ile Cys Val Gln Leu Asn Thr Ser Val Glu
                85                  90                  95
```

```
Ile Asn Cys Thr Gly Ala Gly His Cys Asn Ile Ser Arg Ala Lys Trp
            100                 105                 110

Asn Asn Thr Leu Lys Gln Ile Ala Ser Cys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asp
145                 150                 155                 160

Ser Thr Gln Leu Phe Asn Ser Thr Trp Phe Asn Ser Thr Trp Ser
                165                 170                 175

<210> SEQ ID NO 59
<211> LENGTH: 168
<212> TYPE: PRT
<213> ORGANISM: Artificial Sequence
<220> FEATURE:
<223> OTHER INFORMATION: Engineered Env

<400> SEQUENCE: 59

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Ala Gly Met
        35                  40                  45

Pro Arg Cys Gly Gly Gly Ala Val Ser Thr Gln Leu Leu Leu Asn Gly
    50                  55                  60

Ser Leu Ala Glu Glu Glu Val Val Cys Arg Ser Val Asn Phe Thr Asp
65                  70                  75                  80

Asn Ala Lys Ser Ile Cys Val Gln Leu Asn Thr Ser Val Glu Ile Asn
                85                  90                  95

Cys Thr Gly Ala Gly His Cys Asn Ile Ser Arg Ala Lys Trp Asn Asn
            100                 105                 110

Thr Leu Lys Gln Ile Ala Ser Cys Leu Arg Glu Gln Phe Gly Asn Asn
        115                 120                 125

Lys Thr Ile Ile Phe Lys Gln Ser Ser Gly Gly Asp Pro Glu Ile Val
    130                 135                 140

Thr His Ser Phe Asn Cys Gly Gly Glu Phe Phe Tyr Cys Asp Ser Thr
145                 150                 155                 160

Gln Leu Phe Asn Ser Thr Trp Phe
                165

<210> SEQ ID NO 60
<211> LENGTH: 175
<212> TYPE: PRT
<213> ORGANISM: Artificial Sequence
<220> FEATURE:
<223> OTHER INFORMATION: Engineered Env

<400> SEQUENCE: 60

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asp Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
    50                  55                  60
```

```
Asn Gly Ser Leu Ala Glu Glu Val Val Ile Arg Ser Val Asp Phe
 65                  70                  75                  80

Thr Asp Asn Ala Lys Ser Ile Cys Val Gln Leu Asp Thr Ser Val Glu
                 85                  90                  95

Ile Asp Cys Thr Gly Ala Gly His Cys Asp Ile Ser Arg Ala Lys Trp
            100                 105                 110

Asp Asn Thr Leu Lys Gln Ile Ala Ser Lys Leu Arg Glu Gln Phe Gly
        115                 120                 125

Asn Asp Lys Thr Ile Ile Phe Lys Gln Ser Ser Gly Gly Asp Pro Glu
130                 135                 140

Ile Val Thr His Ser Phe Asn Cys Gly Gly Glu Phe Phe Tyr Cys Asp
145                 150                 155                 160

Ser Thr Gln Leu Phe Asp Ser Thr Trp Phe Asp Ser Thr Trp Ser
                165                 170                 175
```

<210> SEQ ID NO 61
<211> LENGTH: 185
<212> TYPE: PRT
<213> ORGANISM: Artificial Sequence
<220> FEATURE:
<223> OTHER INFORMATION: Engineered Env

<400> SEQUENCE: 61

```
Gly Glu Phe Phe Tyr Cys Asp Ser Thr Gln Leu Phe Asn Ser Thr Trp
  1               5                  10                  15

Phe Asn Ser Thr Trp Ser Thr Glu Gly Ser Asn Asn Thr Glu Gly Ser
                 20                  25                  30

Asp Thr Ile Thr Leu Pro Cys Arg Pro Ala Pro Pro His Cys Ser
            35                  40                  45

Ser Asn Ile Thr Gly Leu Ile Leu Thr Arg Asp Gly Gly Asn Ser Asn
         50                  55                  60

Asn Glu Ser Glu Ile Phe Arg Pro Gly Gly Gly Asp Met Arg Asp Ile
 65                  70                  75                  80

Ala Arg Cys Gln Ile Ala Gly Thr Val Val Ser Thr Gln Leu Leu Leu
                 85                  90                  95

Asn Gly Ser Leu Ala Glu Glu Val Val Ile Arg Ser Val Asn Phe
            100                 105                 110

Thr Asp Asn Ala Lys Ser Ile Cys Val Gln Leu Asn Thr Ser Val Glu
        115                 120                 125

Ile Asn Cys Thr Gly Ala Gly His Cys Asn Ile Ser Arg Ala Lys Trp
130                 135                 140

Asn Asn Thr Leu Lys Gln Ile Ala Ser Lys Leu Arg Glu Gln Phe Gly
145                 150                 155                 160

Asn Asn Lys Thr Ile Ile Phe Lys Gln Ser Ser Gly Gly Asp Pro Glu
                165                 170                 175

Ile Val Thr His Ser Phe Asn Cys Gly
            180                 185
```

<210> SEQ ID NO 62
<211> LENGTH: 185
<212> TYPE: PRT
<213> ORGANISM: Artificial Sequence
<220> FEATURE:
<223> OTHER INFORMATION: Engineered Env

<400> SEQUENCE: 62

Gly Glu Phe Phe Tyr Cys Asp Ser Thr Gln Leu Phe Asn Ser Thr Trp

```
            1               5                   10                  15
        Phe Asn Ser Thr Trp Ser Thr Glu Gly Ser Asn Asn Thr Glu Gly Ser
                    20                  25                  30
        Asp Thr Ile Thr Leu Pro Cys Arg Pro Ala Pro Pro His Cys Ser
                    35                  40                  45
        Ser Asn Ile Thr Gly Leu Ile Leu Thr Arg Asp Gly Gly Asn Ser Asn
                    50                  55                  60
        Asn Glu Ser Glu Ile Phe Arg Pro Gly Gly Asp Met Arg Cys Gly
        65                  70                  75                  80
        Ala Arg Ser Gly Ile Ala Gly Thr Val Val Ser Thr Gln Leu Leu Leu
                            85                  90                  95
        Asn Gly Ser Leu Ala Glu Glu Val Val Ile Arg Ser Val Asn Phe
                        100                 105                 110
        Thr Asp Asn Ala Lys Cys Ile Ile Val Gln Leu Asn Thr Ser Val Glu
                        115                 120                 125
        Ile Asn Cys Thr Gly Ala Gly His Cys Asn Ile Ser Arg Ala Lys Trp
                    130                 135                 140
        Asn Asn Thr Leu Lys Gln Ile Ala Ser Lys Leu Arg Glu Gln Phe Gly
        145                 150                 155                 160
        Asn Asn Lys Thr Ile Ile Phe Lys Gln Ser Ser Gly Gly Asp Pro Glu
                        165                 170                 175
        Ile Val Thr His Ser Phe Asn Cys Gly
                        180                 185

<210> SEQ ID NO 63
<211> LENGTH: 185
<212> TYPE: PRT
<213> ORGANISM: Artificial Sequence
<220> FEATURE:
<223> OTHER INFORMATION: Engineered Env

<400> SEQUENCE: 63

Gly Glu Phe Phe Tyr Cys Asp Ser Thr Gln Leu Phe Asn Ser Thr Trp
        1               5                   10                  15
        Phe Asn Ser Thr Trp Ser Thr Glu Gly Ser Asn Asn Thr Glu Gly Ser
                    20                  25                  30
        Asp Thr Ile Thr Leu Pro Cys Arg Pro Ala Pro Pro His Cys Ser
                    35                  40                  45
        Ser Asn Ile Thr Gly Leu Ile Leu Thr Arg Asp Gly Gly Asn Ser Asn
                    50                  55                  60
        Asn Glu Ser Glu Ile Phe Arg Pro Gly Gly Asp Met Arg Asp Ile
        65                  70                  75                  80
        Ala Arg Cys Gln Ile Ala Gly Thr Val Val Ser Thr Gln Leu Leu Leu
                            85                  90                  95
        Asn Gly Ser Leu Ala Glu Glu Val Val Cys Arg Ser Val Asn Phe
                        100                 105                 110
        Thr Asp Asn Ala Lys Ser Ile Cys Val Gln Leu Asn Thr Ser Val Glu
                        115                 120                 125
        Ile Asn Cys Thr Gly Ala Gly His Cys Asn Ile Ser Arg Ala Lys Trp
                    130                 135                 140
        Asn Asn Thr Leu Lys Gln Ile Ala Ser Cys Leu Arg Glu Gln Phe Gly
        145                 150                 155                 160
        Asn Asn Lys Thr Ile Ile Phe Lys Gln Ser Ser Gly Gly Asp Pro Glu
                        165                 170                 175
        Ile Val Thr His Ser Phe Asn Cys Gly
```

180                 185

<210> SEQ ID NO 64
<211> LENGTH: 175
<212> TYPE: PRT
<213> ORGANISM: Artificial Sequence
<220> FEATURE:
<223> OTHER INFORMATION: Engineered Env

<400> SEQUENCE: 64

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 65
<211> LENGTH: 175
<212> TYPE: PRT
<213> ORGANISM: Artificial Sequence
<220> FEATURE:
<223> OTHER INFORMATION: Engineered Env

<400> SEQUENCE: 65

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
            130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 66
<211> LENGTH: 175
<212> TYPE: PRT
<213> ORGANISM: Artificial Sequence
<220> FEATURE:
<223> OTHER INFORMATION: Engineered Env

<400> SEQUENCE: 66

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asp Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
            130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 67
<211> LENGTH: 175
<212> TYPE: PRT
<213> ORGANISM: Artificial Sequence
<220> FEATURE:
<223> OTHER INFORMATION: Engineered Env

<400> SEQUENCE: 67

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Phe Leu
50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
        130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 68
<211> LENGTH: 175
<212> TYPE: PRT
<213> ORGANISM: Artificial Sequence
<220> FEATURE:
<223> OTHER INFORMATION: Engineered Env

<400> SEQUENCE: 68

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
        130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 69
<211> LENGTH: 175
<212> TYPE: PRT
<213> ORGANISM: Artificial Sequence
<220> FEATURE:
<223> OTHER INFORMATION: Engineered Env

<400> SEQUENCE: 69

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asp Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Phe Leu 50                  55                  60
Asn Gly Ser Leu Ala Glu Glu Val Val Ile Arg Ser Val Asp Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Asn Lys Thr Ile Ile Phe Lys Gln Ser Ser Gly Gly Asp Pro Glu
                130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 70
<211> LENGTH: 175
<212> TYPE: PRT
<213> ORGANISM: Artificial Sequence
<220> FEATURE:
<223> OTHER INFORMATION: Engineered Env

<400> SEQUENCE: 70

Asp Thr Ile Thr Leu Pro Cys Arg Pro Ala Pro Pro His Cys Ser
 1               5                  10                  15

Ser Asn Ile Thr Gly Leu Ile Leu Thr Arg Asp Gly Gly Asn Ser Asn
                 20                  25                  30

Asn Glu Ser Glu Ile Phe Arg Pro Gly Gly Gly Asp Met Arg Asp Asn
                 35                  40                  45

Ala Arg Cys Gln Ile Ala Gly Thr Val Val Ser Thr Gln Leu Leu Leu
                 50                  55                  60

Asn Gly Ser Leu Ala Glu Glu Val Val Ile Arg Ser Val Asn Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Asn Lys Thr Ile Ile Phe Lys Gln Ser Ser Gly Gly Asp Pro Glu
                130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 71
<211> LENGTH: 174
<212> TYPE: PRT
<213> ORGANISM: Artificial Sequence
<220> FEATURE:
<223> OTHER INFORMATION: Engineered Env

<400> SEQUENCE: 71

Asp Thr Ile Thr Leu Pro Cys Arg Pro Ala Pro Pro His Cys Ser
 1               5                  10                  15

```
Ser Asn Ile Thr Gly Leu Ile Leu Thr Arg Asp Gly Gly Asn Ser Asn
         20                  25                  30

Asn Glu Ser Glu Ile Phe Arg Pro Gly Gly Gly Asp Met Arg Asp Ile
         35                  40                  45

Ala Arg Cys Gln Ile Ala Gly Thr Val Val Ser Thr Gln Leu Leu Leu
 50                  55                  60

Asn Gly Ser Leu Ala Glu Glu Val Val Ile Arg Ser Val Asn Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Lys Thr Ile Ile Phe Lys Gln Ser Ser Gly Gly Asp Pro Glu Ile
                130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr Trp Ser
                165                 170
```

<210> SEQ ID NO 72
<211> LENGTH: 175
<212> TYPE: PRT
<213> ORGANISM: Artificial Sequence
<220> FEATURE:
<223> OTHER INFORMATION: Engineered Env

<400> SEQUENCE: 72

```
Asp Thr Ile Thr Leu Pro Cys Arg Pro Ala Pro Pro His Cys Ser
 1               5                  10                  15

Ser Asn Ile Thr Gly Leu Ile Leu Thr Arg Asp Gly Gly Asn Ser Asn
         20                  25                  30

Asn Glu Ser Glu Ile Phe Arg Pro Gly Gly Gly Asp Met Arg Asp Ile
         35                  40                  45

Ala Arg Cys Gln Ile Ala Gly Thr Val Val Ser Thr Gln Leu Leu Leu
 50                  55                  60

Asn Gly Ser Leu Ala Glu Glu Val Val Ile Arg Ser Val Asn Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Asn Lys Thr Ile Ile Phe Lys Gln Ser Ser Gly Gly Asp Pro Glu
                130                 135                 140

Ile Val Thr His Ser Phe Asn Cys Gly Gly Glu Phe Phe Tyr Cys Asn
145                 150                 155                 160

Thr Thr Gln Leu Phe Asn Ser Thr Trp Phe Asn Ser Thr Trp Ser
                165                 170                 175
```

<210> SEQ ID NO 73
<211> LENGTH: 175
<212> TYPE: PRT
<213> ORGANISM: Artificial Sequence
<220> FEATURE:

<223> OTHER INFORMATION: Engineered Env

<400> SEQUENCE: 73

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Ile Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
        130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 74
<211> LENGTH: 175
<212> TYPE: PRT
<213> ORGANISM: Artificial Sequence
<220> FEATURE:
<223> OTHER INFORMATION: Engineered Env

<400> SEQUENCE: 74

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Gln Leu Phe Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Asn Lys Thr Ile Ile Phe Lys Gln Ser Ser Gly Gly Asp Pro Glu
        130                 135                 140

Ile Val Thr His Trp Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 75
<211> LENGTH: 175
<212> TYPE: PRT
<213> ORGANISM: Artificial Sequence
<220> FEATURE:
<223> OTHER INFORMATION: Engineered Env

<400> SEQUENCE: 75

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Gln Leu Phe Leu
    50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Trp Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175
```

<210> SEQ ID NO 76
<211> LENGTH: 175
<212> TYPE: PRT
<213> ORGANISM: Artificial Sequence
<220> FEATURE:
<223> OTHER INFORMATION: Engineered Env

<400> SEQUENCE: 76

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Asn Ser Asn
                20                  25                  30

Asp Glu Ser Glu Ile Phe Arg Pro Gly Gly Gly Asp Met Arg Asp Ile
            35                  40                  45

Ala Arg Cys Gln Ile Ala Gly Thr Val Val Ser Gln Leu Phe Leu
    50                  55                  60

Asn Gly Ser Leu Ala Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
```

Ile Val Thr His Trp Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 77
<211> LENGTH: 174
<212> TYPE: PRT
<213> ORGANISM: Artificial Sequence
<220> FEATURE:
<223> OTHER INFORMATION: Engineered Env

<400> SEQUENCE: 77

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Thr Ser Asp
                20                  25                  30

Asp Lys Thr Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Glu Val Val Ile Arg Ser Glu Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Lys Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp Ser
                165                 170

<210> SEQ ID NO 78
<211> LENGTH: 174
<212> TYPE: PRT
<213> ORGANISM: Artificial Sequence
<220> FEATURE:
<223> OTHER INFORMATION: Engineered Env

<400> SEQUENCE: 78

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Ile Ser Asp
                20                  25                  30

Asp Lys Thr Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Glu Val Val Ile Arg Ser Glu Asp Phe
65                  70                  75                  80

Arg Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Lys Thr Ile Ile Phe Ser Gln Ser Leu Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp Ser
                165                 170

<210> SEQ ID NO 79
<211> LENGTH: 174
<212> TYPE: PRT
<213> ORGANISM: Artificial Sequence
<220> FEATURE:
<223> OTHER INFORMATION: Engineered Env

<400> SEQUENCE: 79

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Ile Ser Asp
            20                  25                  30

Asp Lys Thr Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Glu Asn Phe
65                  70                  75                  80

Thr Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Lys Thr Ile Ile Phe Ser Gln Ser Leu Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp Ser
                165                 170

<210> SEQ ID NO 80
<211> LENGTH: 173
<212> TYPE: PRT
<213> ORGANISM: Artificial Sequence
<220> FEATURE:
<223> OTHER INFORMATION: Engineered Env

<400> SEQUENCE: 80

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Ile Ser Asp
            20                  25                  30

Asp Lys Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Glu Asp Phe
65                  70                  75                  80

Arg Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Lys Thr Ile Ile Phe Ser Gln Ser Leu Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 81
<211> LENGTH: 173
<212> TYPE: PRT
<213> ORGANISM: Artificial Sequence
<220> FEATURE:
<223> OTHER INFORMATION: Engineered Env

<400> SEQUENCE: 81

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Ile Ser Asp
                20                  25                  30

Asp Lys Thr Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Glu Asp Phe
65                  70                  75                  80

Arg Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Leu Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 82
<211> LENGTH: 173
<212> TYPE: PRT
<213> ORGANISM: Artificial Sequence
<220> FEATURE:
<223> OTHER INFORMATION: Engineered Env

<400> SEQUENCE: 82

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Gly Ile Ser Asp

```
                    20                  25                  30
Asp Asp Thr Glu Ile Phe Arg Pro Ser Gly Gly Asp Met Arg Asp Ile
                35                  40                  45
Ala Arg Cys Gln Ile Ala Gly Thr Val Val Ser Thr Gln Leu Phe Leu
         50                  55                  60
Asn Gly Ser Leu Ala Glu Glu Val Val Ile Arg Ser Glu Asp Phe
 65                  70                  75                  80
Arg Asp Asn Ser Lys Ser Ile Cys Val Gln Leu Asn Thr Ser Val Glu
                 85                  90                  95
Ile Asn Cys Thr Gly Ala Gly His Cys Asn Ile Ser Arg Ala Lys Trp
                100                 105                 110
Asn Asn Thr Leu Lys Gln Ile Ala Ser Lys Leu Arg Glu Gln Phe Gly
             115                 120                 125
Asn Arg Thr Ile Ile Phe Ser Gln Ser Leu Gly Gly Asp Pro Glu Phe
             130                 135                 140
Val Thr His Ser Phe Asn Cys Gly Gly Glu Phe Phe Tyr Cys Asp Ser
145                 150                 155                 160
Thr Gln Leu Phe Asp Ser Thr Trp Phe Asp Ser Thr Trp
             165                 170

<210> SEQ ID NO 83
<211> LENGTH: 173
<212> TYPE: PRT
<213> ORGANISM: Artificial Sequence
<220> FEATURE:
<223> OTHER INFORMATION: Engineered Env

<400> SEQUENCE: 83

Asp Thr Ile Thr Leu Pro Cys Arg Pro Ala Pro Pro His Cys Ser
 1               5                  10                  15
Ser Asn Ile Thr Gly Leu Ile Leu Thr Arg Ala Gly Gly Ile Ser Asp
                 20                  25                  30
Asp Asn Thr Glu Ile Phe Arg Pro Ser Gly Gly Asp Met Arg Asp Ile
                 35                  40                  45
Ala Arg Cys Gln Ile Ala Gly Thr Val Val Ser Thr Gln Leu Phe Leu
         50                  55                  60
Asn Gly Ser Leu Ala Glu Glu Val Val Ile Arg Ser Glu Asp Phe
 65                  70                  75                  80
Arg Asp Asn Ser Lys Ser Ile Cys Val Gln Leu Asn Thr Ser Val Glu
                 85                  90                  95
Ile Asn Cys Thr Gly Ala Gly His Cys Asn Ile Ser Arg Ala Lys Trp
                100                 105                 110
Asn Asn Thr Leu Lys Gln Ile Ala Ser Lys Leu Arg Glu Gln Phe Gly
             115                 120                 125
Asn Arg Thr Ile Ile Phe Ser Gln Ser Leu Gly Gly Asp Pro Glu Phe
             130                 135                 140
Val Thr His Ser Phe Asn Cys Gly Gly Glu Phe Phe Tyr Cys Asp Ser
145                 150                 155                 160
Thr Gln Leu Phe Asp Ser Thr Trp Phe Asp Ser Thr Trp
             165                 170

<210> SEQ ID NO 84
<211> LENGTH: 173
<212> TYPE: PRT
<213> ORGANISM: Artificial Sequence
<220> FEATURE:
<223> OTHER INFORMATION: Engineered Env
```

<400> SEQUENCE: 84

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Ile Ser Asp
            20                  25                  30

Asp Asn Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Glu Asp Phe
65                  70                  75                  80

Arg Asp Asn Ser Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Leu Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 85
<211> LENGTH: 173
<212> TYPE: PRT
<213> ORGANISM: Artificial Sequence
<220> FEATURE:
<223> OTHER INFORMATION: Engineered Env

<400> SEQUENCE: 85

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Val Ser Asp
            20                  25                  30

Asp Asp Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

```
<210> SEQ ID NO 86
<211> LENGTH: 173
<212> TYPE: PRT
<213> ORGANISM: Artificial Sequence
<220> FEATURE:
<223> OTHER INFORMATION: Engineered Env

<400> SEQUENCE: 86

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Val Ser Asp
                20                  25                  30

Asp Asp Thr Glu Ile Phe Arg Pro Ala Gly Gly Asp Met Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr Trp
                165                 170

<210> SEQ ID NO 87
<211> LENGTH: 170
<212> TYPE: PRT
<213> ORGANISM: Artificial Sequence
<220> FEATURE:
<223> OTHER INFORMATION: Engineered Env

<400> SEQUENCE: 87

Asp Thr Ile Thr Leu Pro Cys Arg Pro Ala Pro Pro His Cys Ser
1               5                   10                  15

Ser Asn Ile Thr Gly Leu Ile Leu Thr Arg Gly Gly Val Ser Asp
                20                  25                  30

Asp Asp Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Ser Gln Ser Ser Gly Gly Asp Pro Glu Phe
    130                 135                 140
```

Val Thr His Ser Phe Asn Cys Gly Gly Glu Phe Phe Tyr Cys Asp Ser
145                 150                 155                 160

Thr Gln Leu Phe Asp Ser Thr Trp Phe Asp
                165                 170

<210> SEQ ID NO 88
<211> LENGTH: 172
<212> TYPE: PRT
<213> ORGANISM: Artificial Sequence
<220> FEATURE:
<223> OTHER INFORMATION: Engineered Env

<400> SEQUENCE: 88

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Val Ser Asn
                20                  25                  30

Asp Glu Thr Glu Ile Phe Arg Pro Ser Gly Gly Asp Met Arg Asp Ile
                35                  40                  45

Ala Arg Cys Gln Ile Ala Gly Thr Val Val Ser Thr Gln Leu Phe Leu
            50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 89
<211> LENGTH: 172
<212> TYPE: PRT
<213> ORGANISM: Artificial Sequence
<220> FEATURE:
<223> OTHER INFORMATION: Engineered Env

<400> SEQUENCE: 89

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asp Glu Thr Glu Ile Phe Arg Pro Ser Gly Gly Asp Met Arg Asp Ile
                35                  40                  45

Ala Arg Cys Gln Ile Ala Gly Thr Val Val Ser Thr Gln Leu Phe Leu
            50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp

Asn Asn Thr Leu Lys Gln Ile Ala Ser Lys Leu Arg Glu Gln Phe Gly
            115                 120                 125

Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 90
<211> LENGTH: 172
<212> TYPE: PRT
<213> ORGANISM: Artificial Sequence
<220> FEATURE:
<223> OTHER INFORMATION: Engineered Env

<400> SEQUENCE: 90

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30

Asp Glu Ser Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
            115                 120                 125

Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 91
<211> LENGTH: 172
<212> TYPE: PRT
<213> ORGANISM: Artificial Sequence
<220> FEATURE:
<223> OTHER INFORMATION: Engineered Env

<400> SEQUENCE: 91

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30

Asp Glu Thr Glu Ile Phe Arg Pro Gly Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 92
<211> LENGTH: 172
<212> TYPE: PRT
<213> ORGANISM: Artificial Sequence
<220> FEATURE:
<223> OTHER INFORMATION: Engineered Env

<400> SEQUENCE: 92

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
                20                  25                  30

Asp Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Leu Leu
        50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 93
<211> LENGTH: 172
<212> TYPE: PRT
<213> ORGANISM: Artificial Sequence
<220> FEATURE:
<223> OTHER INFORMATION: Engineered Env

<400> SEQUENCE: 93

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
                20                  25                  30

Asp Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
 50                  55                  60

Asn Gly Ser Leu Ala Glu Glu Val Val Ile Arg Ser Val Asp Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Arg Thr Ile Ile Phe Lys Gln Ser Ser Gly Gly Asp Pro Glu Phe
                130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 94
<211> LENGTH: 172
<212> TYPE: PRT
<213> ORGANISM: Artificial Sequence
<220> FEATURE:
<223> OTHER INFORMATION: Engineered Env

<400> SEQUENCE: 94

Asp Thr Ile Thr Leu Pro Cys Arg Pro Ala Pro Pro His Cys Ser
 1               5                  10                  15

Ser Asn Ile Thr Gly Leu Ile Leu Thr Arg Asp Gly Gly Val Ser Asn
                 20                  25                  30

Asp Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
 50                  55                  60

Asn Gly Ser Leu Ala Glu Glu Val Val Ile Arg Ser Val Asp Phe
 65                  70                  75                  80

Arg Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
                115                 120                 125

Asn Lys Thr Ile Ile Phe Lys Gln Ser Ser Gly Gly Asp Pro Glu Phe
                130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170

<210> SEQ ID NO 95
<211> LENGTH: 172
<212> TYPE: PRT
<213> ORGANISM: Artificial Sequence
<220> FEATURE:
<223> OTHER INFORMATION: Engineered Env

<400> SEQUENCE: 95

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Val Ser Asn
            20                  25                  30

Asp Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Ile
    130                 135                 140

Val Thr His Ser Phe Asn Cys Gly Gly Glu Phe Phe Tyr Cys Asp Ser
145                 150                 155                 160

Thr Gln Leu Phe Asn Ser Thr Trp Phe Asn Ser Thr
                165                 170
```

<210> SEQ ID NO 96
<211> LENGTH: 172
<212> TYPE: PRT
<213> ORGANISM: Artificial Sequence
<220> FEATURE:
<223> OTHER INFORMATION: Engineered Env

<400> SEQUENCE: 96

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Val Ser Asn
            20                  25                  30

Asp Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asp Thr Ser Val Glu
                85                  90                  95

Ile Asp Cys Thr Gly Ala Gly His Cys Asp Ile Ser Arg Ala Lys Trp
            100                 105                 110

Asp Asn Thr Leu Lys Gln Ile Ala Ser Lys Leu Arg Glu Gln Phe Gly
        115                 120                 125

Asp Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asp Ser
145                 150                 155                 160

Thr Gln Leu Phe Asp Ser Thr Trp Phe Asp Ser Thr
                165                 170
```

```
<210> SEQ ID NO 97
<211> LENGTH: 172
<212> TYPE: PRT
<213> ORGANISM: Artificial Sequence
<220> FEATURE:
<223> OTHER INFORMATION: Engineered Env

<400> SEQUENCE: 97

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
                20                  25                  30

Asn Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
        50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 98
<211> LENGTH: 172
<212> TYPE: PRT
<213> ORGANISM: Artificial Sequence
<220> FEATURE:
<223> OTHER INFORMATION: Engineered Env

<400> SEQUENCE: 98

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asn Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
        50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140
```

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 99
<211> LENGTH: 172
<212> TYPE: PRT
<213> ORGANISM: Artificial Sequence
<220> FEATURE:
<223> OTHER INFORMATION: Engineered Env

<400> SEQUENCE: 99

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
                20                  25                  30

Asn Glu Thr Glu Ile Phe Arg Pro Gly Gly Gly Asp Met Arg Asp Ile
            35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 100
<211> LENGTH: 172
<212> TYPE: PRT
<213> ORGANISM: Artificial Sequence
<220> FEATURE:
<223> OTHER INFORMATION: Engineered Env

<400> SEQUENCE: 100

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
                20                  25                  30

Asn Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

```
Asn Asn Thr Leu Lys Gln Ile Ala Ser Lys Leu Arg Glu Gln Phe Gly
            115                 120                 125

Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
            165                 170

<210> SEQ ID NO 101
<211> LENGTH: 172
<212> TYPE: PRT
<213> ORGANISM: Artificial Sequence
<220> FEATURE:
<223> OTHER INFORMATION: Engineered Env

<400> SEQUENCE: 101

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30

Asn Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Glu Val Val Ile Arg Ser Val Asp Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
            115                 120                 125

Asn Arg Thr Ile Ile Phe Lys Gln Ser Ser Gly Gly Asp Pro Glu Phe
        130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
            165                 170

<210> SEQ ID NO 102
<211> LENGTH: 172
<212> TYPE: PRT
<213> ORGANISM: Artificial Sequence
<220> FEATURE:
<223> OTHER INFORMATION: Engineered Env

<400> SEQUENCE: 102

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30

Asn Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Glu Val Val Ile Arg Ser Val Asp Phe
```

```
            65                  70                  75                  80
Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Lys Thr Ile Ile Phe Lys Gln Ser Gly Gly Asp Pro Glu Phe
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 103
<211> LENGTH: 172
<212> TYPE: PRT
<213> ORGANISM: Artificial Sequence
<220> FEATURE:
<223> OTHER INFORMATION: Engineered Env

<400> SEQUENCE: 103

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30

Asn Glu Thr Glu Ile Phe Arg Pro Ser Gly Gly Asp Met Arg Asp Ile
        35                  40                  45

Ala Arg Cys Gln Ile Ala Gly Thr Val Val Ser Thr Gln Leu Phe Leu
    50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Arg Thr Ile Ile Phe Lys Gln Ser Ser Gly Gly Asp Pro Glu Ile
    130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 104
<211> LENGTH: 172
<212> TYPE: PRT
<213> ORGANISM: Artificial Sequence
<220> FEATURE:
<223> OTHER INFORMATION: Engineered Env

<400> SEQUENCE: 104

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Val Ser Asn
            20                  25                  30
```

Asn Glu Thr Glu Ile Phe Arg Pro Ser Gly Gly Asp Met Arg Asp Ile
            35                  40                  45

Ala Arg Cys Gln Ile Ala Gly Thr Val Val Ser Thr Gln Leu Phe Leu
 50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Lys Gln Ser Gly Gly Asp Pro Glu Phe
            130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 105
<211> LENGTH: 172
<212> TYPE: PRT
<213> ORGANISM: Artificial Sequence
<220> FEATURE:
<223> OTHER INFORMATION: Engineered Env

<400> SEQUENCE: 105

Asp Thr Ile Thr Leu Pro Cys Arg Pro Ala Pro Pro His Cys Ser
1               5                   10                  15

Ser Asn Ile Thr Gly Leu Ile Leu Thr Arg Ala Gly Gly Val Ser Asp
                20                  25                  30

Asn Asn Thr Glu Ile Phe Phe Pro Ser Gly Gly Asp Met Arg Asp Ile
            35                  40                  45

Ala Arg Cys Gln Ile Ala Gly Thr Val Val Ser Thr Gln Leu Phe Leu
 50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Ser Gln Ser Thr Gly Gly Asp Pro Glu Phe
            130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 106
<211> LENGTH: 173
<212> TYPE: PRT
<213> ORGANISM: Artificial Sequence
<220> FEATURE:
<223> OTHER INFORMATION: Engineered Env

<400> SEQUENCE: 106

Asp Thr Ile Thr Leu Pro Cys Arg Pro Ala Pro Pro His Cys Ser
1               5                   10                  15

Ser Asn Ile Thr Gly Leu Ile Leu Gly Arg Ala Gly Ala Ser Asp
            20                  25                  30

Asp Asn Thr Glu Ile Phe Tyr Pro Ser Gly Asp Met Arg Asp Ile
            35                  40                  45

Ala Arg Cys Gln Ile Ala Gly Thr Val Val Ser Thr Gln Leu Phe Leu
50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Ser Gln Ser Thr Gly Gly Asp Pro Glu Ile
            130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr Trp
                165                 170

<210> SEQ ID NO 107
<211> LENGTH: 172
<212> TYPE: PRT
<213> ORGANISM: Artificial Sequence
<220> FEATURE:
<223> OTHER INFORMATION: Engineered Env

<400> SEQUENCE: 107

Asp Thr Ile Thr Leu Pro Cys Arg Pro Ala Pro Pro His Cys Ser
1               5                   10                  15

Ser Asn Ile Thr Gly Leu Ile Leu Thr Arg Ala Gly Gly Val Ser Asn
            20                  25                  30

Asn Glu Thr Glu Ile Phe Phe Pro Ser Gly Gly Asp Met Arg Asp Ile
            35                  40                  45

Ala Arg Cys Gln Ile Ala Gly Thr Val Val Ser Thr Gln Leu Phe Leu
50                  55                  60

Asn Gly Ser Leu Ala Glu Glu Val Val Ile Arg Ser Val Asp Phe
65                  70                  75                  80

Arg Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Gln Phe Gly
            115                 120                 125

Asn Arg Thr Ile Ile Phe Lys Gln Ser Ser Gly Gly Asp Pro Glu Phe
            130                 135                 140

Val Thr His Ser Phe Asn Cys Gly Gly Glu Phe Phe Tyr Cys Asn Ser
145                 150                 155                 160

Thr Gln Leu Phe Asn Ser Thr Trp Phe Asn Ser Thr
                165                 170

<210> SEQ ID NO 108

<211> LENGTH: 355
<212> TYPE: PRT
<213> ORGANISM: Artificial Sequence
<220> FEATURE:
<223> OTHER INFORMATION: Engineered Env

<400> SEQUENCE: 108

```
Val Trp Lys Glu Ala Thr Thr Thr Leu Phe Cys Ala Ser Asp Ala Lys
1               5                   10                  15
Ala Tyr Asp Thr Glu Val His Asn Val Trp Ala Thr His Ala Cys Val
            20                  25                  30
Pro Thr Asp Pro Asn Pro Gln Glu Val Glu Leu Glu Asn Val Thr Glu
        35                  40                  45
Asn Phe Asn Met Trp Lys Asn Met Val Glu Gln Met His Glu Asp
    50                  55                  60
Ile Ile Ser Leu Trp Asp Gln Ser Leu Lys Pro Cys Val Lys Leu Thr
65                  70                  75                  80
Gly Gly Ser Val Ile Thr Gln Ala Cys Pro Lys Ile Ser Phe Glu Pro
                85                  90                  95
Ile Pro Ile His Tyr Cys Ala Pro Ala Gly Phe Ala Ile Leu Lys Cys
            100                 105                 110
Lys Asp Lys Lys Phe Asn Gly Lys Gly Pro Cys Ser Asn Val Ser Thr
        115                 120                 125
Val Gln Cys Thr His Gly Ile Arg Pro Val Val Ser Thr Gln Leu Leu
130                 135                 140
Leu Asn Gly Ser Leu Ala Glu Glu Val Val Ile Arg Ser Glu Asn
145                 150                 155                 160
Phe Ala Asp Asn Ala Lys Thr Ile Ile Val Gln Leu Asn Glu Ser Val
                165                 170                 175
Glu Ile Asn Cys Thr Arg Pro Asn Asn Gly Ser Gly Ser Gly Gly
            180                 185                 190
Asp Ile Arg Gln Ala His Cys Asn Leu Ser Arg Ala Lys Trp Asn Asp
        195                 200                 205
Thr Leu Asn Lys Ile Val Ile Lys Leu Arg Glu Gln Phe Gly Asn Lys
210                 215                 220
Thr Ile Val Phe Lys His Ser Ser Gly Gly Asp Pro Glu Ile Val Thr
225                 230                 235                 240
His Ser Phe Asn Cys Gly Gly Glu Phe Phe Tyr Cys Asn Ser Thr Gln
                245                 250                 255
Leu Phe Asn Ser Thr Trp Asn Val Thr Glu Glu Ser Asn Asn Thr Val
            260                 265                 270
Glu Asn Asn Thr Ile Thr Leu Pro Cys Arg Ile Lys Gln Ile Ile Asn
        275                 280                 285
Met Trp Gln Lys Val Gly Arg Ala Met Tyr Ala Pro Pro Ile Arg Gly
290                 295                 300
Gln Ile Arg Cys Ser Ser Asn Ile Thr Gly Leu Leu Leu Thr Arg Asp
305                 310                 315                 320
Gly Gly Pro Glu Asp Asn Lys Thr Glu Val Phe Arg Pro Gly Gly Gly
                325                 330                 335
Asp Met Arg Asp Asn Trp Arg Ser Glu Leu Tyr Lys Tyr Lys Val Val
            340                 345                 350
Lys Ile Glu
        355
```

<210> SEQ ID NO 109

<211> LENGTH: 299
<212> TYPE: PRT
<213> ORGANISM: Artificial Sequence
<220> FEATURE:
<223> OTHER INFORMATION: Engineered Env

<400> SEQUENCE: 109

```
Val Trp Lys Asp Ala Thr Thr Thr Leu Phe Cys Ala Ser Asp Ala Lys
1               5                   10                  15

Ala His Glu Thr Glu Val His Asn Val Trp Ala Thr His Ala Cys Val
            20                  25                  30

Pro Thr Asp Pro Asn Pro Gln Glu Val Glu Leu Lys Asn Val Thr Glu
        35                  40                  45

Asn Phe Asn Met Trp Lys Asn Met Val Glu Gln Met His Glu Asp
    50                  55                  60

Ile Ile Ser Leu Trp Asp Gln Ser Leu Lys Pro Cys Val Lys Leu Thr
65                  70                  75                  80

Gly Gly Ser Val Ile Thr Gln Ala Cys Pro Lys Val Ser Phe Glu Pro
                85                  90                  95

Ile Pro Ile His Tyr Cys Ala Pro Ala Gly Phe Ala Ile Leu Lys Cys
            100                 105                 110

Lys Asp Lys Lys Phe Asn Gly Lys Gly Pro Cys Ser Asn Val Ser Thr
        115                 120                 125

Val Gln Cys Thr His Gly Ile Arg Pro Val Val Ser Thr Gln Leu Leu
    130                 135                 140

Leu Asn Gly Ser Leu Ala Glu Glu Val Val Ile Arg Ser Glu Asp
145                 150                 155                 160

Phe Arg Asn Asn Ala Lys Ile Ile Val Gln Leu Asn Glu Ser Val
                165                 170                 175

Glu Ile Asn Cys Thr Gly Ala Gly His Cys Asn Leu Ser Arg Ala Lys
            180                 185                 190

Trp Asn Asp Thr Leu Asn Lys Ile Val Ile Lys Leu Arg Glu Gln Phe
        195                 200                 205

Gly Asn Lys Thr Ile Val Phe Lys His Ser Ser Gly Gly Asp Pro Glu
    210                 215                 220

Ile Val Thr His Ser Phe Asn Cys Gly Gly Glu Phe Phe Tyr Cys Asn
225                 230                 235                 240

Ser Thr Gln Leu Phe Asn Ser Thr Trp Asn Val Thr Glu Glu Ser Asn
                245                 250                 255

Asn Thr Val Glu Asn Asn Thr Ile Thr Leu Pro Cys Arg Ile Lys Gln
            260                 265                 270

Ile Ile Asn Met Trp Gln Glu Val Gly Arg Ala Met Tyr Ala Pro Pro
        275                 280                 285

Ile Arg Gly Gln Ile Arg Cys Ser Ser Asn Ile
    290                 295
```

<210> SEQ ID NO 110
<211> LENGTH: 175
<212> TYPE: PRT
<213> ORGANISM: Artificial Sequence
<220> FEATURE:
<223> OTHER INFORMATION: Engineered Env

<400> SEQUENCE: 110

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
```

```
                    20                  25                  30
Asn Glu Ser Glu Ile Phe Arg Pro Gly Gly Gly Asp Met Arg Asp Ile
                35                  40                  45
Ala Asn Cys Ser Ile Ala Gly Thr Val Val Ser Thr Gln Leu Leu Leu
            50                  55                  60
Asn Gly Ser Leu Ala Glu Glu Val Val Ile Arg Ser Val Asn Phe
65                  70                  75                  80
Thr Asp Asn Ala Lys Ser Ile Cys Val Gln Leu Asn Thr Ser Val Glu
                85                  90                  95
Ile Asn Cys Thr Gly Ala Gly His Cys Asn Ile Ser Arg Ala Lys Trp
                100                 105                 110
Asn Asn Thr Leu Lys Gln Ile Ala Ser Lys Leu Arg Glu Gln Phe Gly
            115                 120                 125
Asn Asn Lys Thr Ile Ile Phe Lys Gln Ser Ser Gly Gly Asp Pro Glu
            130                 135                 140
Ile Val Thr His Ser Phe Asn Cys Gly Gly Glu Phe Phe Tyr Cys Asn
145                 150                 155                 160
Ser Thr Gln Leu Phe Asn Ser Thr Trp Phe Asn Ser Thr Trp Ser
                165                 170                 175
```

<210> SEQ ID NO 111
<211> LENGTH: 175
<212> TYPE: PRT
<213> ORGANISM: Artificial Sequence
<220> FEATURE:
<223> OTHER INFORMATION: Engineered Env

<400> SEQUENCE: 111

```
Asp Thr Ile Thr Leu Pro Cys Arg Pro Ala Pro Pro His Cys Ser
1               5                   10                  15
Ser Asn Ile Thr Gly Leu Ile Leu Thr Arg Asp Gly Gly Asn Ser Asn
                20                  25                  30
Asn Glu Ser Glu Ile Phe Arg Pro Gly Gly Gly Asp Met Arg Asp Ile
                35                  40                  45
Ala Arg Cys Gln Asn Ala Ser Thr Val Val Ser Thr Gln Leu Leu Leu
            50                  55                  60
Asn Gly Ser Leu Ala Glu Glu Val Val Ile Arg Ser Val Asn Phe
65                  70                  75                  80
Thr Asp Asn Ala Lys Ser Ile Cys Val Gln Leu Asn Thr Ser Val Glu
                85                  90                  95
Ile Asn Cys Thr Gly Ala Gly His Cys Asn Ile Ser Arg Ala Lys Trp
                100                 105                 110
Asn Asn Thr Leu Lys Gln Ile Ala Ser Lys Leu Arg Glu Gln Phe Gly
            115                 120                 125
Asn Asn Lys Thr Ile Ile Phe Lys Gln Ser Ser Gly Gly Asp Pro Glu
            130                 135                 140
Ile Val Thr His Ser Phe Asn Cys Gly Gly Glu Phe Phe Tyr Cys Asn
145                 150                 155                 160
Ser Thr Gln Leu Phe Asn Ser Thr Trp Phe Asn Ser Thr Trp Ser
                165                 170                 175
```

<210> SEQ ID NO 112
<211> LENGTH: 175
<212> TYPE: PRT
<213> ORGANISM: Artificial Sequence
<220> FEATURE:
<223> OTHER INFORMATION: Engineered Env

<400> SEQUENCE: 112

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Asn Val Thr Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175
```

<210> SEQ ID NO 113
<211> LENGTH: 175
<212> TYPE: PRT
<213> ORGANISM: Artificial Sequence
<220> FEATURE:
<223> OTHER INFORMATION: Engineered Env

<400> SEQUENCE: 113

```
Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
            20                  25                  30

Asn Glu Ser Glu Ile Phe Arg Pro Gly Gly Gly Asp Met Arg Asp Ile
        35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Asn Phe Ser
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175
```

<210> SEQ ID NO 114
<211> LENGTH: 175
<212> TYPE: PRT
<213> ORGANISM: Artificial Sequence
<220> FEATURE:
<223> OTHER INFORMATION: Engineered Env

<400> SEQUENCE: 114

```
Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
    50                  55                  60

Asn Gly Ser Leu Ala Glu Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175
```

<210> SEQ ID NO 115
<211> LENGTH: 175
<212> TYPE: PRT
<213> ORGANISM: Artificial Sequence
<220> FEATURE:
<223> OTHER INFORMATION: Engineered Env

<400> SEQUENCE: 115

```
Asp Thr Ile Thr Leu Pro Cys Arg Asn Ala Thr Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
    50                  55                  60

Asn Gly Ser Leu Ala Glu Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140
```

Ile Val Thr His Ser Phe Asn Cys Gly Gly Glu Phe Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 116
<211> LENGTH: 175
<212> TYPE: PRT
<213> ORGANISM: Artificial Sequence
<220> FEATURE:
<223> OTHER INFORMATION: Engineered Env

<400> SEQUENCE: 116

Asp Thr Ile Thr Leu Pro Cys Arg Pro Ala Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Ile Ala Gly Thr Val Val Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp
            100                 105                 110

Asn Asn Thr Leu Lys Gln Ile Ala Ser Lys Leu Arg Glu Gln Phe Gly
        115                 120                 125

Asn Asn Lys Thr Ile Ile Phe Lys Gln Ser Ser Gly Gly Asp Pro Glu
    130                 135                 140

Ile Val Thr His Ser Phe Asn Cys Gly Asn Glu Thr Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 117
<211> LENGTH: 175
<212> TYPE: PRT
<213> ORGANISM: Artificial Sequence
<220> FEATURE:
<223> OTHER INFORMATION: Engineered Env

<400> SEQUENCE: 117

Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Gly Asp Met Arg Asp Ile
            35                  40                  45

Ala Arg Cys Gln Asn Ala Ser Thr Val Val Ser Thr Gln Leu Leu Leu
    50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
                85                  90                  95

Ile Asn Cys Thr Gly Ala Gly His Cys Asn Ile Ser Arg Ala Lys Trp

```
                    100                 105                 110
Asn Asn Thr Leu Lys Gln Ile Ala Ser Lys Leu Arg Glu Gln Phe Gly
            115                 120                 125
Asn Asn Lys Thr Ile Ile Phe Lys Gln Ser Ser Gly Gly Asp Pro Glu
            130                 135                 140
Ile Val Thr His Ser Phe Asn Cys Gly Asn Glu Thr Phe Tyr Cys Asn
145                 150                 155                 160
Ser Thr Gln Leu Phe Asn Ser Thr Trp Phe Asn Ser Thr Trp Ser
            165                 170                 175

<210> SEQ ID NO 118
<211> LENGTH: 175
<212> TYPE: PRT
<213> ORGANISM: Artificial Sequence
<220> FEATURE:
<223> OTHER INFORMATION: Engineered Env

<400> SEQUENCE: 118

Asp Thr Ile Thr Leu Pro Cys Asn Pro Ser Pro Pro His Cys Ser
1               5                   10                  15
Ser Asn Ile Thr Gly Leu Ile Leu Thr Arg Asp Gly Gly Asn Ser Asn
            20                  25                  30
Asn Glu Ser Glu Ile Phe Arg Pro Gly Gly Gly Asp Met Arg Asp Ile
        35                  40                  45
Ala Asn Cys Ser Ile Ala Gly Thr Val Val Ser Thr Gln Leu Leu Leu
    50                  55                  60
Asn Gly Ser Leu Ala Glu Glu Val Val Ile Arg Ser Val Asn Phe
65                  70                  75                  80
Thr Asp Asn Ala Lys Ser Ile Cys Val Gln Leu Asn Thr Ser Val Glu
                85                  90                  95
Ile Asn Cys Thr Gly Ala Gly His Cys Asn Ile Ser Arg Ala Lys Trp
                100                 105                 110
Asn Asn Thr Leu Lys Gln Ile Ala Ser Lys Leu Arg Glu Gln Phe Gly
            115                 120                 125
Asn Asn Lys Thr Ile Ile Phe Lys Gln Ser Ser Gly Gly Asp Pro Glu
            130                 135                 140
Ile Val Thr His Ser Phe Asn Cys Gly Asn Glu Thr Phe Tyr Cys Asn
145                 150                 155                 160
Ser Thr Gln Leu Phe Asn Ser Thr Trp Phe Asn Ser Thr Trp Ser
            165                 170                 175

<210> SEQ ID NO 119
<211> LENGTH: 175
<212> TYPE: PRT
<213> ORGANISM: Artificial Sequence
<220> FEATURE:
<223> OTHER INFORMATION: Engineered Env

<400> SEQUENCE: 119

Asp Thr Ile Thr Leu Pro Cys Asn Pro Ser Pro Pro His Cys Ser
1               5                   10                  15
Ser Asn Ile Thr Gly Leu Ile Leu Thr Arg Asp Gly Gly Asn Ser Asn
            20                  25                  30
Asn Glu Ser Glu Ile Phe Arg Pro Gly Gly Gly Asp Met Arg Asp Ile
        35                  40                  45
Ala Asn Cys Ser Ile Ala Gly Asn Val Thr Ser Thr Gln Leu Leu Leu
    50                  55                  60
```

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
            85                  90                  95

Ile Asn Cys Thr Gly Ala Gly His Cys Asn Ile Ser Arg Ala Lys Trp
        100                 105                 110

Asn Asn Thr Leu Lys Gln Ile Ala Ser Lys Leu Arg Glu Gln Phe Gly
    115                 120                 125

Asn Asn Lys Thr Ile Ile Phe Lys Gln Ser Ser Gly Gly Asp Pro Glu
130                 135                 140

Ile Val Thr His Ser Phe Asn Cys Gly Asn Glu Thr Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 120
<211> LENGTH: 175
<212> TYPE: PRT
<213> ORGANISM: Artificial Sequence
<220> FEATURE:
<223> OTHER INFORMATION: Engineered Env

<400> SEQUENCE: 120

Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Gly Asn Ser Asn
                20                  25                  30

Asn Glu Ser Glu Ile Phe Arg Pro Gly Gly Asp Met Arg Asp Ile
            35                  40                  45

Ala Asn Cys Ser Ile Ala Gly Thr Val Val Ser Thr Gln Leu Leu Leu
        50                  55                  60

Asn Gly Ser Leu Ala Glu Glu Val Val Ile Arg Ser Val Asn Phe
65                  70                  75                  80

Thr Asp Asn Ala Lys Ser Ile Cys Val Gln Leu Asn Thr Ser Val Glu
            85                  90                  95

Ile Asn Cys Thr Gly Ala Gly His Cys Asn Ile Ser Arg Ala Lys Trp
        100                 105                 110

Asn Asn Thr Leu Lys Gln Ile Ala Ser Lys Leu Arg Glu Asn Phe Ser
    115                 120                 125

Asn Asn Lys Thr Ile Ile Phe Lys Gln Ser Ser Gly Gly Asp Pro Glu
130                 135                 140

Ile Val Thr His Ser Phe Asn Cys Gly Asn Glu Thr Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 121
<211> LENGTH: 175
<212> TYPE: PRT
<213> ORGANISM: Artificial Sequence
<220> FEATURE:
<223> OTHER INFORMATION: Engineered Env

<400> SEQUENCE: 121

Asp Thr Ile Thr Leu Pro Cys Asn Pro Ser Pro Pro His Cys Ser
1               5                   10                  15

Ser Asn Ile Thr Gly Leu Ile Leu Thr Arg Asp Gly Gly Asn Ser Asn
                20                  25                  30

```
Asn Glu Ser Glu Ile Phe Arg Pro Gly Gly Gly Asp Met Arg Asp Ile
         35                  40                  45

Ala Asn Cys Ser Ile Ala Gly Asn Val Thr Ser Thr Gln Leu Leu Leu
 50                  55                  60

Asn Gly Ser Leu Ala Glu Glu Val Val Ile Arg Ser Val Asn Phe
 65                  70                  75                  80

Thr Asp Asn Ala Lys Ser Ile Cys Val Gln Leu Asn Thr Ser Val Glu
                 85                  90                  95

Ile Asn Cys Thr Gly Ala Gly His Cys Asn Ile Ser Arg Ala Lys Trp
                100                 105                 110

Asn Asn Thr Leu Lys Gln Ile Ala Ser Lys Leu Arg Glu Asn Phe Ser
                115                 120                 125

Asn Asn Lys Thr Ile Ile Phe Lys Gln Ser Ser Gly Gly Asp Pro Glu
                130                 135                 140

Ile Val Thr His Ser Phe Asn Cys Gly Asn Glu Thr Phe Tyr Cys Asn
145                 150                 155                 160

Ser Thr Gln Leu Phe Asn Ser Thr Trp Phe Asn Ser Thr Trp Ser
                165                 170                 175

<210> SEQ ID NO 122
<211> LENGTH: 4
<212> TYPE: PRT
<213> ORGANISM: Artificial Sequence
<220> FEATURE:
<223> OTHER INFORMATION: Linker (Ac-Cys-Gly-Gly-Gly) with N-terminal
      acetylation on the Cys residue
<220> FEATURE:
<221> NAME/KEY: MOD_RES
<222> LOCATION: (1)..(1)
<223> OTHER INFORMATION: ACETYLATION

<400> SEQUENCE: 122

Cys Gly Gly Gly
1

<210> SEQ ID NO 123
<211> LENGTH: 8
<212> TYPE: PRT
<213> ORGANISM: Artificial Sequence
<220> FEATURE:
<223> OTHER INFORMATION: Poly-His-Gly Tag

<400> SEQUENCE: 123

Gly Ser His His His His His His
1               5

<210> SEQ ID NO 124
<211> LENGTH: 9
<212> TYPE: PRT
<213> ORGANISM: Artificial Sequence
<220> FEATURE:
<223> OTHER INFORMATION: Poly-His-Gly Tag

<400> SEQUENCE: 124

Gly Thr Lys His His His His His His
1               5

<210> SEQ ID NO 125
<211> LENGTH: 64
<212> TYPE: DNA
<213> ORGANISM: Artificial Sequence
<220> FEATURE:
<223> OTHER INFORMATION: Fab mutagenesis primer
```

<400> SEQUENCE: 125
caaatcttgt gacaaaactc accatcacca tcaccattga cagcacctga actcctgggg    60
ggac    64

<210> SEQ ID NO 126
<211> LENGTH: 8
<212> TYPE: PRT
<213> ORGANISM: Artificial Sequence
<220> FEATURE:
<223> OTHER INFORMATION: Gly-Ser Linker

<400> SEQUENCE: 126

Gly Ser Gly Gly Gly Gly Ser Gly
1               5

<210> SEQ ID NO 127
<211> LENGTH: 55
<212> TYPE: DNA
<213> ORGANISM: Artificial Sequence
<220> FEATURE:
<223> OTHER INFORMATION: gp120-His mutagenesis primer

<400> SEQUENCE: 127
ggaacaaggg cgctcatcat caccaccatc accattgata ggtggggatc ggagc    55

<210> SEQ ID NO 128
<211> LENGTH: 29
<212> TYPE: DNA
<213> ORGANISM: Artificial Sequence
<220> FEATURE:
<223> OTHER INFORMATION: VDJ knock-in amplifier primer

<400> SEQUENCE: 128
gggatggtca tgtatcatcc tttttctag    29

<210> SEQ ID NO 129
<211> LENGTH: 23
<212> TYPE: DNA
<213> ORGANISM: Artificial Sequence
<220> FEATURE:
<223> OTHER INFORMATION: VDJ knock-in amplifier primer

<400> SEQUENCE: 129
agaaggtgtg cacaccgctg gac    23

<210> SEQ ID NO 130
<211> LENGTH: 27
<212> TYPE: DNA
<213> ORGANISM: Artificial Sequence
<220> FEATURE:
<223> OTHER INFORMATION: VDJ knock-in amplifier primer

<400> SEQUENCE: 130
gtagcaactg caaccggtgt acattct    27

<210> SEQ ID NO 131
<211> LENGTH: 22
<212> TYPE: DNA
<213> ORGANISM: Artificial Sequence
<220> FEATURE:
<223> OTHER INFORMATION: VDJ knock-in amplifier primer

<400> SEQUENCE: 131
gctcagggaa rtagcccttg ac    22

<210> SEQ ID NO 132
<211> LENGTH: 21
<212> TYPE: DNA
<213> ORGANISM: Artificial Sequence
<220> FEATURE:
<223> OTHER INFORMATION: VJ knock-in amplifier primer

<400> SEQUENCE: 132
actgaggcac ctccagatgt t                                              21

<210> SEQ ID NO 133
<211> LENGTH: 19
<212> TYPE: DNA
<213> ORGANISM: Artificial Sequence
<220> FEATURE:
<223> OTHER INFORMATION: VJ knock-in amplifier primer

<400> SEQUENCE: 133
tgggaagatg gatacagtt                                                 19

<210> SEQ ID NO 134
<211> LENGTH: 447
<212> TYPE: PRT
<213> ORGANISM: Artificial Sequence
<220> FEATURE:
<223> OTHER INFORMATION: Fig. 2 - The engineered and multimerized
      Envelope (e/m Env) of FIG. 1 with additional supporting sequences

<400> SEQUENCE: 134

Met Asp Ala Met Lys Arg Gly Leu Cys Cys Val Leu Leu Leu Cys Gly
1               5                   10                  15

Ala Val Phe Val Ser Pro Ser Ala Ser Val Trp Lys Glu Ala Lys Thr
            20                  25                  30

Thr Leu Phe Cys Ala Ser Asp Ala Lys Ala Tyr Glu Lys Glu Cys His
        35                  40                  45

Asn Val Trp Ala Thr His Ala Cys Val Pro Thr Asp Pro Asn Pro Gln
    50                  55                  60

Glu Val Val Leu Glu Asn Val Thr Glu Asn Phe Asn Met Trp Lys Asn
65                  70                  75                  80

Asp Met Val Asp Gln Met Gln Glu Asp Val Ile Ser Ile Trp Asp Gln
                85                  90                  95

Cys Leu Lys Pro Cys Val Lys Leu Thr Asn Thr Ser Thr Leu Thr Gln
            100                 105                 110

Ala Cys Pro Lys Val Thr Phe Asp Pro Ile Pro Ile His Tyr Cys Ala
        115                 120                 125

Pro Ala Gly Tyr Ala Ile Leu Lys Cys Asn Asn Lys Thr Phe Asn Gly
    130                 135                 140

Lys Gly Pro Cys Asn Asn Val Ser Thr Val Gln Cys Thr His Gly Ile
145                 150                 155                 160

Lys Pro Val Val Ser Thr Gln Leu Leu Leu Asn Gly Ser Leu Ala Glu
                165                 170                 175

Glu Glu Ile Val Ile Arg Ser Lys Asn Leu Arg Asp Asn Ala Lys Ile
            180                 185                 190

Ile Ile Val Gln Leu Asn Lys Ser Val Glu Ile Val Cys Thr Arg Pro
        195                 200                 205

Asn Asn Gly Gly Ser Gly Ser Gly Gly Asp Ile Arg Gln Ala Tyr Cys
    210                 215                 220

Asn Ile Ser Gly Arg Asn Trp Ser Glu Ala Val Asn Gln Val Lys Lys

```
            225                 230                 235                 240
Lys Leu Lys Glu His Phe Pro His Lys Asn Ile Ser Phe Gln Ser Ser
                245                 250                 255

Ser Gly Gly Asp Leu Glu Ile Thr Thr His Ser Phe Asn Cys Gly Gly
            260                 265                 270

Glu Phe Phe Tyr Cys Asn Thr Ser Gly Leu Phe Asn Asp Thr Ile Ser
        275                 280                 285

Asn Ala Thr Ile Met Leu Pro Cys Arg Ile Lys Gln Ile Ile Asn Met
    290                 295                 300

Trp Gln Glu Val Gly Lys Ala Ile Tyr Ala Pro Pro Ile Lys Gly Asn
305                 310                 315                 320

Ile Thr Cys Lys Ser Asp Ile Thr Gly Leu Leu Leu Arg Asp Gly
                325                 330                 335

Gly Asp Thr Thr Asp Asn Thr Glu Ile Phe Arg Pro Ser Gly Gly Asp
            340                 345                 350

Met Arg Asp Asn Trp Arg Ser Glu Leu Tyr Lys Tyr Lys Val Val Glu
        355                 360                 365

Ile Lys Pro Leu Ser Gly Arg Ala His Ala Gly Trp Glu Thr Pro Glu
    370                 375                 380

Gly Cys Glu Gln Val Leu Thr Gly Lys Arg Leu Met Gln Cys Leu Pro
385                 390                 395                 400

Asn Pro Glu Asp Val Lys Met Ala Leu Glu Val Tyr Lys Leu Ser Leu
                405                 410                 415

Glu Ile Glu Gln Leu Glu Leu Gln Arg Asp Ser Ala Arg Gln Ser Thr
            420                 425                 430

Leu Asp Lys Glu Leu Val Pro Arg Gly Ser His His His His His
        435                 440                 445
```

<210> SEQ ID NO 135
<211> LENGTH: 103
<212> TYPE: PRT
<213> ORGANISM: Artificial Sequence
<220> FEATURE:
<223> OTHER INFORMATION: Fig. 7 - glVRC/NIH

<400> SEQUENCE: 135

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Tyr Glu Phe Phe Gly Gln
                85                  90                  95

Gly Thr Lys Leu Glu Ile Lys
            100
```

<210> SEQ ID NO 136
<211> LENGTH: 103
<212> TYPE: PRT
<213> ORGANISM: Artificial Sequence
<220> FEATURE:
<223> OTHER INFORMATION: Fig. 7 - gl12A21

-continued

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Ala Val Leu Glu Phe Phe Gly Pro
                85                  90                  95

Gly Thr Lys Val Asp Ile Lys
            100

<210> SEQ ID NO 137
<211> LENGTH: 103
<212> TYPE: PRT
<213> ORGANISM: Artificial Sequence
<220> FEATURE:
<223> OTHER INFORMATION: Fig. 7 - g13BNC60

<400> SEQUENCE: 137

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Phe Ile Gly Pro
                85                  90                  95

Gly Thr Lys Val Asp Ile Lys
            100

<210> SEQ ID NO 138
<211> LENGTH: 103
<212> TYPE: PRT
<213> ORGANISM: Artificial Sequence
<220> FEATURE:
<223> OTHER INFORMATION: Fig. 7 - g1VRC-CH31

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Tyr Cys Gln Gln Tyr Glu Thr Phe Gly Gln
                85                  90                  95

Gly Thr Lys Leu Glu Ile Lys
            100

<210> SEQ ID NO 139
<211> LENGTH: 104
<212> TYPE: PRT
<213> ORGANISM: Artificial Sequence
<220> FEATURE:
<223> OTHER INFORMATION: Fig. 7 - glPGV04

<400> SEQUENCE: 139

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Leu Glu Phe Phe Gly
                85                  90                  95

Gln Gly Thr Arg Leu Glu Ile Lys
            100

<210> SEQ ID NO 140
<211> LENGTH: 104
<212> TYPE: PRT
<213> ORGANISM: Artificial Sequence
<220> FEATURE:
<223> OTHER INFORMATION: Fig. 7 - glPGV19/20

<400> SEQUENCE: 140

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Lys Ser Gly Asn Thr Ala Ser Leu Thr Ile Ser Gly Leu Gln
65                  70                  75                  80

Ala Glu Asp Glu Ala Asp Tyr Tyr Cys Ser Ser Tyr Glu Phe Phe Gly
                85                  90                  95

Gly Gly Thr Lys Val Phe Val Leu
            100

<210> SEQ ID NO 141
<211> LENGTH: 119
<212> TYPE: PRT
<213> ORGANISM: Artificial Sequence
<220> FEATURE:
<223> OTHER INFORMATION: Fig. 14 - g13BNC60 (Heavy Chain)

<400> SEQUENCE: 141
```

-continued

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Arg Ser Asp Phe Trp Asp Phe Asp Leu Trp Gly Arg Gly
            100                 105                 110

Thr Leu Val Thr Val Ser Ser
        115

<210> SEQ ID NO 142
<211> LENGTH: 119
<212> TYPE: PRT
<213> ORGANISM: Artificial Sequence
<220> FEATURE:
<223> OTHER INFORMATION: Fig. 14 - Heavy Chain Seq 1

<400> SEQUENCE: 142

Gln Val Gln Leu Val Gln Ser Gly Ala Glu Val Lys Lys Pro Gly Ala
1               5                   10                  15

Ser Val Lys Val Ser Cys Lys Ala Ser Gly His Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg Glu Arg Ser Asp Phe Trp Asp Phe Asp Leu Trp Gly Arg Gly
            100                 105                 110

Thr Leu Val Thr Val Ser Ser
        115

<210> SEQ ID NO 143
<211> LENGTH: 119
<212> TYPE: PRT
<213> ORGANISM: Artificial Sequence
<220> FEATURE:
<223> OTHER INFORMATION: Fig. 14 - Heavy Chain Seq 2

<400> SEQUENCE: 143

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Gln Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Arg Ser Asp Phe Trp Asp Phe Asp Leu Trp Gly Arg Gly
            100                 105                 110

Thr Leu Val Thr Val Ser Ser
            115

<210> SEQ ID NO 144
<211> LENGTH: 104
<212> TYPE: PRT
<213> ORGANISM: Artificial Sequence
<220> FEATURE:
<223> OTHER INFORMATION: Fig. 14 - Light Chain Seq 1

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Asn Gln Pro
65                  70                  75                  80

Glu Asp Ile Ala Thr Tyr Tyr Cys Gln Gln Tyr Glu Phe Ile Gly Pro
                85                  90                  95

Gly Thr Lys Val Asp Ile Lys Arg
            100

<210> SEQ ID NO 145
<211> LENGTH: 104
<212> TYPE: PRT
<213> ORGANISM: Artificial Sequence
<220> FEATURE:
<223> OTHER INFORMATION: Fig. 14 - Light Chain Seq 2

<400> SEQUENCE: 145

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Phe Gln Gln Lys Pro Gly Lys Ala Pro Lys Leu Leu Ile
        35                  40                  45

Leu Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Gly Leu Gln Pro
65                  70                  75                  80

Glu Asp Ile Ala Thr Tyr Tyr Cys Gln Gln Tyr Glu Phe Ile Gly Pro
                85                  90                  95

Gly Thr Lys Val Asp Ile Lys Arg
            100

<210> SEQ ID NO 146
<211> LENGTH: 104
<212> TYPE: PRT

<213> ORGANISM: Artificial Sequence
<220> FEATURE:
<223> OTHER INFORMATION: Fig. 14 - Light Chain Seq 3

<400> SEQUENCE: 146

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Cys Phe Gln His Lys Ser Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Ala Thr Ser Ser Ile Ser Ser Leu Gln Pro
65                  70                  75                  80

Glu Asp Ile Phe Thr Tyr Tyr Cys Gln Gln Tyr Glu Phe Ile Gly Pro
                85                  90                  95

Gly Thr Lys Val Asp Ile Lys Arg
            100

<210> SEQ ID NO 147
<211> LENGTH: 104
<212> TYPE: PRT
<213> ORGANISM: Artificial Sequence
<220> FEATURE:
<223> OTHER INFORMATION: Fig. 14 - g13BNC60 - (Light Chain)

<400> SEQUENCE: 147

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Glu Phe Ile Gly Pro
                85                  90                  95

Gly Thr Lys Val Asp Ile Lys Arg
            100

<210> SEQ ID NO 148
<211> LENGTH: 423
<212> TYPE: PRT
<213> ORGANISM: Artificial Sequence
<220> FEATURE:
<223> OTHER INFORMATION: FIG. 1 e/m Env sequence

<400> SEQUENCE: 148

Val Trp Lys Glu Ala Lys Thr Thr Leu Phe Cys Ala Ser Asp Ala Lys
1               5                   10                  15

Ala Tyr Glu Lys Glu Cys His Asn Val Trp Ala Thr His Ala Cys Val
            20                  25                  30

Pro Thr Asp Pro Asn Pro Gln Glu Val Val Leu Glu Asn Val Thr Glu
        35                  40                  45

Asn Phe Asn Met Trp Lys Asn Asp Met Val Asp Gln Met Gln Glu Asp
    50                  55                  60

```
Val Ile Ser Ile Trp Asp Gln Cys Leu Lys Pro Cys Val Lys Leu Thr
65                  70                  75                  80

Asn Thr Ser Thr Leu Thr Gln Ala Cys Pro Lys Val Thr Phe Asp Pro
                85                  90                  95

Ile Pro Ile His Tyr Cys Ala Pro Ala Gly Tyr Ala Ile Leu Lys Cys
            100                 105                 110

Asn Asn Lys Thr Phe Asn Gly Lys Gly Pro Cys Asn Asn Val Ser Thr
        115                 120                 125

Val Gln Cys Thr His Gly Ile Lys Pro Val Val Ser Thr Gln Leu Leu
    130                 135                 140

Leu Asn Gly Ser Leu Ala Glu Glu Glu Ile Val Ile Arg Ser Lys Asn
145                 150                 155                 160

Leu Arg Asp Asn Ala Lys Ile Ile Ile Val Gln Leu Asn Lys Ser Val
                165                 170                 175

Glu Ile Val Cys Thr Arg Pro Asn Asn Gly Gly Ser Gly Ser Gly Gly
            180                 185                 190

Asp Ile Arg Gln Ala Tyr Cys Asn Ile Ser Gly Arg Asn Trp Ser Glu
        195                 200                 205

Ala Val Asn Gln Val Lys Lys Lys Leu Lys Glu His Phe Pro His Lys
    210                 215                 220

Asn Ile Ser Phe Gln Ser Ser Ser Gly Gly Asp Leu Glu Ile Thr Thr
225                 230                 235                 240

His Ser Phe Asn Cys Gly Gly Glu Phe Phe Tyr Cys Asn Thr Ser Gly
                245                 250                 255

Leu Phe Asn Asp Thr Ile Ser Asn Ala Thr Ile Met Leu Pro Cys Arg
            260                 265                 270

Ile Lys Gln Ile Ile Asn Met Trp Gln Glu Val Gly Lys Ala Ile Tyr
        275                 280                 285

Ala Pro Pro Ile Lys Gly Asn Ile Thr Cys Lys Ser Asp Ile Thr Gly
    290                 295                 300

Leu Leu Leu Leu Arg Asp Gly Gly Asp Thr Thr Asp Asn Thr Glu Ile
305                 310                 315                 320

Phe Arg Pro Ser Gly Gly Asp Met Arg Asp Asn Trp Arg Ser Glu Leu
                325                 330                 335

Tyr Lys Tyr Lys Val Val Glu Ile Lys Pro Leu Ser Gly Arg Ala His
            340                 345                 350

Ala Gly Trp Glu Thr Pro Glu Gly Cys Glu Gln Val Leu Thr Gly Lys
        355                 360                 365

Arg Leu Met Gln Cys Leu Pro Asn Pro Glu Asp Val Lys Met Ala Leu
    370                 375                 380

Glu Val Tyr Lys Leu Ser Leu Glu Ile Glu Gln Leu Glu Leu Gln Arg
385                 390                 395                 400

Asp Ser Ala Arg Gln Ser Thr Leu Asp Lys Glu Leu Val Pro Arg Gly
                405                 410                 415

Ser His His His His His
            420
```